(12) United States Patent
Naccari et al.

(10) Patent No.: US 8,114,986 B2
(45) Date of Patent: Feb. 14, 2012

(54) ANALOGOUS COMPOUNDS OF 6-THIOGUANOSINE TRIPHOSPHATE, THEIR USE IN MEDICAL FIELDS AND PROCESSES FOR THEIR PREPARATION

(75) Inventors: Giancarlo Naccari, Monza (IT); Sergio Baroni, Villa d'Adda (IT)

(73) Assignee: Giuliani International Limited, Dublin (IE)

( * ) Notice: Subject to any disclaimer, the term of this patent is extended or adjusted under 35 U.S.C. 154(b) by 654 days.

(21) Appl. No.: 11/989,054

(22) PCT Filed: Jul. 24, 2006

(86) PCT No.: PCT/IE2006/000077
§ 371 (c)(1),
(2), (4) Date: Jun. 6, 2008

(87) PCT Pub. No.: WO2007/010515
PCT Pub. Date: Jan. 25, 2007

(65) Prior Publication Data
US 2010/0323980 A9        Dec. 23, 2010

(30) Foreign Application Priority Data

Jul. 22, 2005  (IT) ............................ RM2005A0391
Jun. 14, 2006  (IE) ..................................... 2006/0448

(51) Int. Cl.
*C07H 19/22* (2006.01)
(52) U.S. Cl. ................. 536/27.13; 536/27.1; 536/27.14; 536/27.2; 536/27.21
(58) Field of Classification Search .................. None
See application file for complete search history.

(56) References Cited

U.S. PATENT DOCUMENTS

| | | | |
|---|---|---|---|
| 3,956,277 A | 5/1976 | Elion et al. | |
| 5,733,915 A | 3/1998 | Sandborn | |
| 5,801,159 A | 9/1998 | Miller et al. | |
| 6,355,623 B2 | 3/2002 | Seidman et al. | |
| 6,881,725 B2 | 4/2005 | Yerxa et al. | |
| 7,018,985 B1 | 3/2006 | Boyer et al. | |
| 7,084,128 B2 | 8/2006 | Yerxa et al. | |
| 7,109,181 B2 | 9/2006 | Cowlen et al. | |
| 2002/0058635 A1 | 5/2002 | Averett | |
| 2004/0208862 A1 | 10/2004 | Brady-Kalnay et al. | |
| 2005/0142103 A1 | 6/2005 | Williams et al. | |
| 2005/0215513 A1 | 9/2005 | Boojamra et al. | |
| 2005/0220709 A1 | 10/2005 | Neurath et al. | |
| 2006/0079478 A1 | 4/2006 | Boojamra et al. | |
| 2007/0196822 A1 | 8/2007 | Thomas et al. | |

FOREIGN PATENT DOCUMENTS
WO      WO 95/32984 A1    12/1995

OTHER PUBLICATIONS

Patel et al. Bioorganic & Medicinal Chemistry Letters (1995), vol. 5, pp. 507-512.*
Parker et al. Cancer Research (1994), vol. 54, pp. 1742-1745.*
Weiss et al. Cancer Research (1974), vol. 34, pp. 581-587.*
Boise, L.H., et al., "Receptors that Regulate T-Cell Susceptibility to Apoptotic Cell Death," *Annals New York Academy of Sciences*, 1995; 766: 70-80.
Tiede, I., et al,. "CD28-Dependent Rac1 Activation is the Molecular Target of Azathioprine in Primary Human CD4+ T Lymphocytes," *J. Clinical Investigation*, 2003; 111(8): 1133-1145.
Maltzman, J.S., et al,. "Azathioprine: Old Drug, New Actions," *J. Clinical Investigation*, 2003; 111(8): 1122-1124.
Boise, L.H., et al,."CD28 Costimulation Can Promote T Cell Survival by Enhancing the Expression of Bcl-$x_L$," *Immunity*, 1995; 3: 87-98.
Khoshnan, A., et al., "The NF-κB Cascade is Important in Bcl-$X_L$ Expression and for the Anti-Apoptotic Effects of CD28 Receptor in Primary Human CD4+ T Lymphocytes," *J. Immunol.*, 2000; 165: 1743-1754.

(Continued)

*Primary Examiner* — Patrick Lewis
(74) *Attorney, Agent, or Firm* — Goodwin Procter LLP

(57) ABSTRACT

The invention relates to analogous compounds of 6-thioguanosine triphosphate of general formula (I). A compound of the general formula (I); wherein the dashed bond in the sugar moiety can be either single or double and wherein R1, R2, R3, R4 or R5, equal or different between each other, have general formula -(Int)$_m$-Ter, wherein m is between 0 and 12 and Int and Ter are Internal and Terminal building blocks, wherein Int is selected from the group consisting of formula (II); and Ter is selected from the group consisting of formula (III). And wherein X represents either carbon or nitrogen atom within aromatic ring, Y represents either oxygen or sulphur atom and an additional group Q, group Qi or groups Qi (Qi indicates that the group or several groups may be bound to any unsaturated moiety of the ring) are selected from the group consisting of —OH, —COOH, —N(CH$_3$)$_2$, —N(CH$_2$—CH$_3$)$_2$|—CO—CH$_3$, —CO—O—CH$_3$, —O—CH$_3$, —S—CH$_3$, —SO$_2$—CH$_3$, —CN, —NO$_2$ or -Halogen elements, and wherein R5 may be formula (IV) and metal and ammonium salts thereof, wherein n is between 0 and 5, or oxygen or phosphorus is partially or completely replaced by nitrogen, sulphur, methyleno groups or their derivatives. The invention also concerns the uses of the above mentioned compounds in medical field and the process for their preparation.

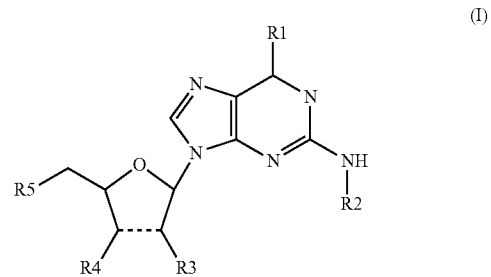

(I)

10 Claims, 26 Drawing Sheets

OTHER PUBLICATIONS

Noel, P.J., et al., "CD28 Costimulation Prevents Cell Death During Primary T cell Activation," *J. Immmunol.*, 1996; 157: 636-642.

Frauwirth, K.A., et al., "Activation and Inhibition of Lymphocytes by Costimulation," *J. Clinical Investigation*, 2002; 109(3): 295-299.

Marinari, B., et al., "Vav Cooperates with CD28 to Induce NF-κB Activation via a Pathway Involving Rac-1 an Mitogen-Activated Kinase Kinase 1," *Eur. J. Immunol.*, 2002; 32: 447-456.

Faruqi, T.R., et al., "Rac1 Mediates STAT3 Activation by Autocrine IL-6," *PNAS*, 2001; 98(16): 9014-9019.

Mudter, J., et al., "The Role of Signal Transducers and Activators of Transcription in T Inflammatory Bowel Diseases," *Inflammatory Bowel Diseases*, 2003; 9(5): 332-337.

Lovato, P., et al., "Constitutive STAT3 Activation in Intestinal T Cells from Patients with Crohn's Disease," *J. Biol. Chem.*, 2003; 278(19): 16777-16781.

Van Aelst, et al, "Rho GTPases and Signaling Networks," *Genes & Development*, 1997; 11: 2295-2322.

Kohyama, et al., "A Facile Synthesis of AICAR from Inosine," *Synthesis* (2003) 17: 2639-2642.

Imai, et al., "Synthesis of Compounds related to Inosine 5'-Phosphate and their Flavor Enhancing Activity. IV. 2-Substituted Inosine 5'-Phosphates," *Chem. Pharm. Bull.*, (1971) 19(3): 576-586.

Ostermann, et al., "New N-2-Labelled Fluorescent Derivates of Guanosine Nucleotides and their Interaction with GTP-Binding Proteins," *Nucleosides & Nucleotides* (1999), 18(2):245-262.

Ludwig, J., "A New Route to Nucleoside 5'-triphosphastes," *Acta Biochim. et Biophys. Acad. Sci. Hung.* (1981) 16(3-4): 131-133.

Dec. 15, 2006, International Search Report, PCT/IE2006/000077.

Jan. 22, 2008, International Preliminary Report on Patentability, with Written Opinion, PCT/IE2006/000077.

Patel, Vinod, F., et al., (1995) "Novel Trityl Linked Drug Immunoconjugates for Cancer Therapy," Biorganic & Medicinal Chemistry Letters 5: 507-512.

* cited by examiner

Figure 6A

Measurement day 1

| | classical drug (6-thio-GTP) | | | | | | | |
|---|---|---|---|---|---|---|---|---|
| | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | -1 | 0 | 2 | 0 | 0 | 0 | 0.17 | 0.98 |
| Annexin pos./ PI neg. | 0 | 0 | -2 | 0 | 2 | 0 | 0.00 | 1.26 |

Measurement day 2

| | classical drug (6-thio-GTP) | | | | | | | |
|---|---|---|---|---|---|---|---|---|
| | Buffy1 11.04.06 | Buffy2 14.12.05 | Buffy1 14.12.05 | Buffy1 03.04.06 | Buffy 1 02.05.06 | Buffy F 03.05.06 | mean | StDev |
| Annexin pos./ PI pos. | 3 | -1 | -1 | -2 | -1 | 0 | -0.33 | 1.75 |
| Annexin pos./ PI neg. | 2 | -1 | -1 | 0 | 2 | -1 | 0.17 | 1.47 |

Measurement day 3

| | classical drug (6-thio-GTP) | | | | | | | |
|---|---|---|---|---|---|---|---|---|
| | Buffy1 11.04.06 | Buffy1 14.12.05 | Buffy2 14.12.05 | Buffy1 06.01.06 | Buffy 1 02.05.06 | Buffy F 03.05.06 | mean | StDev |
| Annexin pos./ PI pos. | 1 | 1 | 0 | -2 | -1 | -2 | -0.50 | 1.38 |
| Annexin pos./ PI neg. | -2 | 1 | 1 | 0 | 0 | 0 | 0.00 | 1.10 |

Measurement day 4

| | classical drug (6-thio-GTP) | | | | | | | |
|---|---|---|---|---|---|---|---|---|
| | Buffy1 11.04.06 | Buffy1 14.12.05 | Buffy2 14.12.05 | Buffy1 06.01.06 | Buffy 1 02.05.06 | Buffy F 03.05.06 | mean | StDev |
| Annexin pos./ PI pos. | -5 | 3 | -2 | 0 | 1 | 10 | 1.17 | 5.12 |
| Annexin pos./ PI neg. | -2 | 1 | 0 | 1 | -1 | -13 | -2.33 | 5.35 |

Measurement day 5

| | classical drug (6-thio-GTP) | | | | | | | |
|---|---|---|---|---|---|---|---|---|
| | Buffy1 11.04.06 | Buffy1 14.12.05 | Buffy2 14.12.05 | Buffy1 06.01.06 | Buffy 1 02.05.06 | Buffy F 03.05.06 | mean | StDev |
| Annexin pos./ PI pos. | 2 | 0 | -5 | -3 | 4 | 1 | -0.17 | 3.31 |
| Annexin pos./ PI neg. | 1 | -3 | 1 | 0 | -9 | -14 | -4.00 | 6.20 |

Mean and StDeviation

| | day1 6-Thio-GTP (n=6) | 05B-0 (n=4) | 05B-1 (n=4) | 05C-0 (n=6) | 05C-1 (n=6) | 05C-2 (n=6) | 05C-3 (n=6) | 06D-1 (n=6) |
|---|---|---|---|---|---|---|---|---|
| Annexin pos./ PI pos. | 0.17 | 2.75 | 0.5 | 0.17 | -0.5 | -0.67 | -0.5 | 1.17 |
| StDev | 0.98 | 0.5 | 2.89 | 1.17 | 1.05 | 1.21 | 0.55 | 2.48 |
| Annexin pos./ PI neg. | 0 | 4 | 0 | -2.83 | -0.33 | -1.17 | -0.67 | -0.33 |
| StDev | 1.26 | 4.08 | 2.16 | 7.96 | 1.51 | 3.76 | 1.37 | 1.86 |

SEM

| | day1 6-Thio-GTP (n=6) | 05B-0 (n=4) | 05B-1 (n=4) | 05C-0 (n=6) | 05C-1 (n=6) | 05C-2 (n=6) | 05C-3 (n=6) | 06D-1 (n=6) |
|---|---|---|---|---|---|---|---|---|
| Annexin pos./ PI pos. | 0.17 | 2.75 | 0.5 | 0.17 | -0.5 | -0.67 | -0.5 | 1.17 |
| SEM | 0.4 | 0.25 | 1.45 | 0.48 | 0.43 | 0.49 | 0.22 | 1.01 |
| Annexin pos./ PI neg. | 0 | 4 | 0 | -2.83 | -0.33 | -1.17 | -0.67 | -0.33 |
| SEM | 0.51 | 2.04 | 1.08 | 3.25 | 0.62 | 1.54 | 0.56 | 0.76 |

Figure 6B

Measurement day 1

| | 05B0 | | | | | |
|---|---|---|---|---|---|---|
| | Buffy1 19.04.06 | Buffy2 19.04.06 | Buffy 1 02.05.06 | Buffy F 03.05.06 | mean | StDev |
| Annexin pos./ PI pos. | 3 | 3 | 2 | 3 | 2.75 | 0.50 |
| Annexin pos./ PI neg. | 1 | 3 | 10 | 2 | 4.00 | 4.08 |

Measurement day 2

| | 05B0 | | | | | |
|---|---|---|---|---|---|---|
| | Buffy1 19.04.06 | Buffy2 19.04.06 | Buffy 1 02.05.06 | Buffy F 03.05.06 | mean | StDev |
| Annexin pos./ PI pos. | 12 | 17 | 9 | 8 | 11.50 | 4.04 |
| Annexin pos./ PI neg. | 6 | 10 | 6 | 3 | 6.25 | 2.87 |

Measurement day 3

| | 05B0 | | | | | |
|---|---|---|---|---|---|---|
| | Buffy1 19.04.06 | Buffy2 19.04.06 | Buffy 1 02.05.06 | Buffy F 03.05.06 | mean | StDev |
| Annexin pos./ PI pos. | 21 | 24 | 16 | 9 | 17.50 | 6.56 |
| Annexin pos./ PI neg. | 5 | 7 | 8 | -1 | 4.75 | 4.03 |

Measurement day 4

| | 05B0 | | | | | |
|---|---|---|---|---|---|---|
| | Buffy1 19.04.06 | Buffy2 19.04.06 | Buffy 1 02.05.06 | Buffy F 03.05.06 | mean | StDev |
| Annexin pos./ PI pos. | 30 | 23 | 22 | 13 | 22.00 | 6.98 |
| Annexin pos./ PI neg. | 0 | 3 | 2 | -10 | -1.25 | 5.97 |

Measurement day 5

| | 05B0 | | | | | |
|---|---|---|---|---|---|---|
| | Buffy1 19.04.06 | Buffy2 19.04.06 | Buffy 1 02.05.06 | Buffy F 03.05.06 | mean | StDev |
| Annexin pos./ PI pos. | 17 | 20 | 30 | 10 | 19.25 | 8.30 |
| Annexin pos./ PI neg. | -3 | -1 | -7 | -8 | -4.75 | 3.30 |

Mean and StDeviation

| | 06D-3 (n=6) | 06D-6 (n=6) | 06D-12 (n=6) | 06D-14 (n=6) | 06D-22 (n=6) | 06D-30 (n=6) |
|---|---|---|---|---|---|---|
| Annexin pos./ PI pos. | 0.67 | -0.33 | -0.5 | -0.33 | 0.33 | 0.17 |
| StDev | 0.52 | 0.82 | 1.52 | 1.03 | 1.03 | 1.94 |
| Annexin pos./ PI neg. | -0.33 | -1.17 | -0.67 | 0 | 0 | 0 |
| StDev | 0.82 | 0.75 | 1.03 | 0.89 | 1.1 | 2.1 |

SEM

| | 06D-3 (n=6) | 06D-6 (n=6) | 06D-12 (n=6) | 06D-14 (n=6) | 06D-22 (n=6) | 06D-30 (n=6) |
|---|---|---|---|---|---|---|
| Annexin pos./ PI pos. | 0.67 | -0.33 | -0.5 | -0.33 | 0.33 | 0.17 |
| SEM | 0.21 | 0.33 | 0.62 | 0.42 | 0.42 | 0.79 |
| Annexin pos./ PI neg. | -0.33 | -1.17 | -0.67 | 0 | 0 | 0 |
| SEM | 0.33 | 0.31 | 0.42 | 0.36 | 0.45 | 0.86 |

Figure 6C

Measurement day 1

| | 05B1 | | | | | |
| --- | --- | --- | --- | --- | --- | --- |
| | Buffy1 19.04.06 | Buffy2 19.04.06 | Buffy 1 02.05.06 | Buffy F 03.05.06 | mean | StDev |
| Annexin pos./ PI pos. | 4 | -3 | 0 | 1 | 0.50 | 2.89 |
| Annexin pos./ PI neg. | -1 | -2 | 3 | 0 | 0.00 | 2.16 |

Measurement day 2

| | 05B1 | | | | | |
| --- | --- | --- | --- | --- | --- | --- |
| | Buffy1 19.04.06 | Buffy2 19.04.06 | Buffy 1 02.05.06 | Buffy F 03.05.06 | mean | StDev |
| Annexin pos./ PI pos. | 3 | 6 | 1 | 2 | 3.00 | 2.16 |
| Annexin pos./ PI neg. | -1 | 0 | 4 | 1 | 1.00 | 2.16 |

Measurement day 3

| | 05B1 | | | | | |
| --- | --- | --- | --- | --- | --- | --- |
| | Buffy1 19.04.06 | Buffy2 19.04.06 | Buffy 1 02.05.06 | Buffy F 03.05.06 | mean | StDev |
| Annexin pos./ PI pos. | 4 | -5 | 2 | -1 | 0.00 | 3.92 |
| Annexin pos./ PI neg. | -1 | -1 | -2 | -1 | -1.25 | 0.50 |

Measurement day 4

| | 05B1 | | | | | |
| --- | --- | --- | --- | --- | --- | --- |
| | Buffy1 19.04.06 | Buffy2 19.04.06 | Buffy 1 02.05.06 | Buffy F 03.05.06 | mean | StDev |
| Annexin pos./ PI pos. | 5 | 8 | 5 | 5 | 5.75 | 1.50 |
| Annexin pos./ PI neg. | 0 | 1 | 1 | 5 | 1.75 | 2.22 |

Measurement day 5

| | 05B1 | | | | | |
| --- | --- | --- | --- | --- | --- | --- |
| | Buffy1 19.04.06 | Buffy2 19.04.06 | Buffy 1 02.05.06 | Buffy F 03.05.06 | mean | StDev |
| Annexin pos./ PI pos. | -3 | 5 | 4 | -7 | -0.25 | 5.74 |
| Annexin pos./ PI neg. | 1 | -1 | -6 | 4 | -0.50 | 4.20 |

Mean and StDeviation

| | day2 6-Thio-GTP (n=6) | 05B-0 (n=4) | 05B-1 (n=4) | 05C-0 (n=6) | 05C-1 (n=6) |
| --- | --- | --- | --- | --- | --- |
| Annexin pos./ PI pos. | -0.33 | 11.5 | 3 | -0.67 | -1.67 |
| StDev | 1.75 | 4.04 | 2.16 | 1.75 | 1.75 |
| Annexin pos./ PI neg. | 0.17 | 6.25 | 1 | -0.33 | -0.83 |
| StDev | 1.47 | 2.87 | 2.16 | 1.37 | 3.31 |

SEM

| | day2 6-Thio-GTP (n=6) | 05B-0 (n=4) | 05B-1 (n=4) | 05C-0 (n=6) | 05C-1 (n=6) |
| --- | --- | --- | --- | --- | --- |
| Annexin pos./ PI pos. | -0.33 | 11.5 | 3 | -0.67 | -1.67 |
| SEM | 0.71 | 2.02 | 1.08 | 0.71 | 0.71 |
| Annexin pos./ PI neg. | 0.17 | 6.25 | 1 | -0.33 | -0.83 |
| SEM | 0.6 | 1.44 | 1.08 | 0.56 | 1.35 |

Figure 6D

Measurement day 1

|  | 05C-0 | | | | | | | |
|---|---|---|---|---|---|---|---|---|
|  | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | -2 | 0 | 1 | 1 | 0 | 1 | 0.17 | 1.17 |
| Annexin pos./ PI neg. | 0 | -19 | 0 | 0 | 2 | 0 | -2.83 | 7.96 |

Measurement day 2

|  | 05C-0 | | | | | | | |
|---|---|---|---|---|---|---|---|---|
|  | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | 2 | -3 | 0 | -1 | -2 | 0 | -0.67 | 1.75 |
| Annexin pos./ PI neg. | 2 | -1 | 0 | 0 | -1 | -2 | -0.33 | 1.37 |

Measurement day 3

|  | 05C-0 | | | | | | | |
|---|---|---|---|---|---|---|---|---|
|  | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | 0 | 1 | -3 | -2 | -2 | -2 | -1.33 | 1.51 |
| Annexin pos./ PI neg. | 0 | 0 | -1 | 0 | 0 | 3 | 0.33 | 1.37 |

Measurement day 4

|  | 05C-0 | | | | | | | |
|---|---|---|---|---|---|---|---|---|
|  | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | -2 | -1 | -2 | 4 | 2 | 1 | 0.33 | 2.42 |
| Annexin pos./ PI neg. | 0 | 2 | 0 | 2 | -1 | -2 | 0.17 | 1.60 |

Measurement day 5

|  | 05C-0 | | | | | | | |
|---|---|---|---|---|---|---|---|---|
|  | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | -1 | -1 | -5 | -2 | 0 | -7 | -2.67 | 2.73 |
| Annexin pos./ PI neg. | 2 | -1 | 1 | 5 | -4 | 6 | 1.50 | 3.73 |

Mean and StDeviation

|  | 05C-2 (n=6) | 05C-3 (n=6) | 06D-1 (n=6) | 06D-3 (n=6) | 06D-6 (n=6) | 06D-12 (n=6) | 06D-14 (n=6) | 06D-22 (n=6) |
|---|---|---|---|---|---|---|---|---|
| Annexin pos./ PI pos. | -2 | -1.33 | -1 | -1.17 | -1.67 | -1.33 | -0.33 | 0.33 |
| StDev | 2.1 | 0.82 | 1.41 | 1.47 | 1.51 | 1.97 | 3.27 | 1.51 |
| Annexin pos./ PI neg. | 1 | 0.67 | 0.5 | 0.33 | 0.83 | 0.33 | -0.17 | 0.33 |
| StDev | 1.26 | 1.37 | 1.76 | 1.37 | 1.17 | 1.37 | 1.72 | 0.52 |

SEM

|  | 05C-2 (n=6) | 05C-3 (n=6) | 06D-1 (n=6) | 06D-3 (n=6) | 06D-6 (n=6) | 06D-12 (n=6) | 06D-14 (n=6) | 06D-22 (n=6) |
|---|---|---|---|---|---|---|---|---|
| Annexin pos./ PI pos. | -2 | -1.33 | -1 | -1.17 | -1.67 | -1.33 | -0.33 | 0.33 |
| SEM | 0.86 | 0.33 | 0.58 | 0.6 | 0.62 | 0.8 | 1.33 | 0.62 |
| Annexin pos./ PI neg. | 1 | 0.67 | 0.5 | 0.33 | 0.83 | 0.33 | -0.17 | 0.33 |
| SEM | 0.51 | 0.56 | 0.72 | 0.56 | 0.48 | 0.56 | 0.7 | 0.21 |

Figure 6E

Measurement day 1

|  | 05C-1 Buffy1 11.04.06 | Buffy2 11.04.06 | Buffy1 19.04.06 | Buffy2 19.04.06 | Buffy 1 02.05.06 | Buffy F 03.05.06 | mean | StDev |
|---|---|---|---|---|---|---|---|---|
| Annexin pos./ PI pos. | -2 | 0 | 1 | -1 | -1 | 0 | -0.50 | 1.05 |
| Annexin pos./ PI neg. | 0 | -3 | -1 | 0 | 1 | 1 | -0.33 | 1.51 |

Measurement day 2

|  | 05C-1 Buffy1 11.04.06 | Buffy2 11.04.06 | Buffy1 19.04.06 | Buffy2 19.04.06 | Buffy 1 02.05.06 | Buffy F 03.05.06 | mean | StDev |
|---|---|---|---|---|---|---|---|---|
| Annexin pos./ PI pos. | 1 | -2 | -3 | -3 | -3 | 0 | -1.67 | 1.75 |
| Annexin pos./ PI neg. | 2 | 1 | 1 | 0 | -7 | -2 | -0.83 | 3.31 |

Measurement day 3

|  | 05C-1 Buffy1 11.04.06 | Buffy2 11.04.06 | Buffy1 19.04.06 | Buffy2 19.04.06 | Buffy 1 02.05.06 | Buffy F 03.05.06 | mean | StDev |
|---|---|---|---|---|---|---|---|---|
| Annexin pos./ PI pos. | -1 | 0 | -2 | -4 | -3 | -3 | -2.17 | 1.47 |
| Annexin pos./ PI neg. | 0 | 0 | 0 | 1 | 1 | -1 | 0.17 | 0.75 |

Measurement day 4

|  | 05C-1 Buffy1 11.04.06 | Buffy2 11.04.06 | Buffy1 19.04.06 | Buffy2 19.04.06 | Buffy 1 02.05.06 | Buffy F 03.05.06 | mean | StDev |
|---|---|---|---|---|---|---|---|---|
| Annexin pos./ PI pos. | -3 | 1 | -5 | -9 | -2 | -1 | -3.17 | 3.49 |
| Annexin pos./ PI neg. | 2 | 1 | -1 | 1 | -3 | -2 | -0.33 | 1.97 |

Measurement day 5

|  | 05C-1 Buffy1 11.04.06 | Buffy2 11.04.06 | Buffy1 19.04.06 | Buffy2 19.04.06 | Buffy 1 02.05.06 | Buffy F 03.05.06 | mean | StDev |
|---|---|---|---|---|---|---|---|---|
| Annexin pos./ PI pos. | -1 | -3 | -10 | -14 | -3 | -10 | -6.83 | 5.19 |
| Annexin pos./ PI neg. | 2 | 1 | -1 | 3 | -4 | 8 | 1.50 | 4.04 |

Mean and StDeviation

|  | 06D-30 (n=6) | day3 6-Thio-GTP (n=6) | 05B-0 (n=4) | 05B-1 (n=4) | 05C-0 (n=6) | 05C-1 (n=6) | 05C-2 (n=6) |
|---|---|---|---|---|---|---|---|
| Annexin pos./ PI pos. | -0.17 | -0.5 | 17.5 | 0 | -1.33 | -2.17 | -2.17 |
| StDev | 2.32 | 1.38 | 6.56 | 3.2 | 1.51 | 1.47 | 3.06 |
| Annexin pos./ PI neg. | -0.17 | 0 | 4.75 | -1.25 | 0.33 | 0.17 | 0.17 |
| StDev | 1.17 | 1.1 | 4.03 | 2.22 | 1.37 | 0.75 | 0.41 |

SEM

|  | 06D-30 (n=6) | day3 6-Thio-GTP (n=6) | 05B-0 (n=4) | 05B-1 (n=4) | 05C-0 (n=6) | 05C-1 (n=6) | 05C-2 (n=6) |
|---|---|---|---|---|---|---|---|
| Annexin pos./ PI pos. | -0.17 | -0.5 | 17.5 | 0 | -1.33 | -2.17 | -2.17 |
| SEM | 0.95 | 0.56 | 3.28 | 1.6 | 0.62 | 0.6 | 1.25 |
| Annexin pos./ PI neg. | -0.17 | 0 | 4.75 | -1.25 | 0.33 | 0.17 | 0.17 |
| SEM | 0.48 | 0.45 | 2.02 | 1.11 | 0.56 | 0.31 | 0.17 |

Figure 6 F

Measurement day 1

|  | 05C-2 Buffy1 11.04.06 | Buffy2 11.04.06 | Buffy1 19.04.06 | Buffy2 19.04.06 | Buffy 1 02.05.06 | Buffy F 03.05.06 | mean | StDev |
|---|---|---|---|---|---|---|---|---|
| Annexin pos./ PI pos. | -2 | 0 | -1 | -2 | 0 | 1 | -0.67 | 1.21 |
| Annexin pos./ PI neg. | -5 | -5 | -2 | 0 | 0 | 5 | -1.17 | 3.76 |

Measurement day 2

|  | 05C-2 Buffy1 11.04.06 | Buffy2 11.04.06 | Buffy1 19.04.06 | Buffy2 19.04.06 | Buffy 1 02.05.06 | Buffy F 03.05.06 | mean | StDev |
|---|---|---|---|---|---|---|---|---|
| Annexin pos./ PI pos. | 2 | -3 | -3 | -4 | -2 | -2 | -2.00 | 2.10 |
| Annexin pos./ PI neg. | 2 | 2 | 1 | 0 | 2 | -1 | 1.00 | 1.26 |

Measurement day 3

|  | 05C-2 Buffy1 11.04.06 | Buffy2 11.04.06 | Buffy1 19.04.06 | Buffy2 19.04.06 | Buffy 1 02.05.06 | Buffy F 03.05.06 | mean | StDev |
|---|---|---|---|---|---|---|---|---|
| Annexin pos./ PI pos. | 0 | 2 | -3 | -7 | -3 | -2 | -2.17 | 3.06 |
| Annexin pos./ PI neg. | 1 | 0 | 0 | 0 | 0 | 0 | 0.17 | 0.41 |

Measurement day 4

|  | 05C-2 Buffy1 11.04.06 | Buffy2 11.04.06 | Buffy1 19.04.06 | Buffy2 19.04.06 | Buffy 1 02.05.06 | Buffy F 03.05.06 | mean | StDev |
|---|---|---|---|---|---|---|---|---|
| Annexin pos./ PI pos. | -2 | 1 | -5 | -5 | 0 | 0 | -1.83 | 2.64 |
| Annexin pos./ PI neg. | 0 | 0 | -1 | 1 | 2 | -2 | 0.00 | 1.41 |

Measurement day 5

|  | 05C-2 Buffy1 11.04.06 | Buffy2 11.04.06 | Buffy1 19.04.06 | Buffy2 19.04.06 | Buffy 1 02.05.06 | Buffy F 03.05.06 | mean | StDev |
|---|---|---|---|---|---|---|---|---|
| Annexin pos./ PI pos. | 0 | -4 | -10 | -13 | -3 | -10 | -6.67 | 5.05 |
| Annexin pos./ PI neg. | 0 | -1 | 1 | 1 | -4 | 7 | 0.67 | 3.61 |

Mean and StDeviation

|  | 05C-3 (n=6) | 06D-1 (n=6) | 06D-3 (n=6) | 06D-6 (n=6) | 06D-12 (n=6) | 06D-14 (n=6) | 06D-22 (n=6) | 06D-30 (n=6) |
|---|---|---|---|---|---|---|---|---|
| Annexin pos./ PI pos. | -1.67 | -0.33 | -1.5 | -1.33 | 0.83 | 0.17 | 0.67 | 0.83 |
| StDev | 1.75 | 1.63 | 1.64 | 1.51 | 1.17 | 2.23 | 1.51 | 2.32 |
| Annexin pos./ PI neg. | 0 | 0.5 | 0.33 | 0.33 | 0.83 | 0.33 | 0.67 | 1 |
| StDev | 1.26 | 1.64 | 1.37 | 1.21 | 1.33 | 1.37 | 1.51 | 0.63 |

SEM

|  | 05C-3 (n=6) | 06D-1 (n=6) | 06D-3 (n=6) | 06D-6 (n=6) | 06D-12 (n=6) | 06D-14 (n=6) | 06D-22 (n=6) | 06D-30 (n=6) |
|---|---|---|---|---|---|---|---|---|
| Annexin pos./ PI pos. | -1.67 | -0.33 | -1.5 | -1.33 | 0.83 | 0.17 | 0.67 | 0.83 |
| SEM | 0.71 | 0.66 | 0.67 | 0.62 | 0.48 | 0.91 | 0.62 | 0.95 |
| Annexin pos./ PI neg. | 0 | 0.5 | 0.33 | 0.33 | 0.83 | 0.33 | 0.67 | 1 |
| SEM | 0.51 | 0.67 | 0.56 | 0.49 | 0.54 | 0.56 | 0.62 | 0.26 |

Figure 6G

Measurement day 1

| | 05C-3 | | | | | | | |
|---|---|---|---|---|---|---|---|---|
| | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | -1 | 0 | 0 | -1 | 0 | -1 | -0.50 | 0.55 |
| Annexin pos./ PI neg. | -1 | -3 | -1 | 0 | 1 | 0 | -0.67 | 1.37 |

Measurement day 2

| | 05C-3 | | | | | | | |
|---|---|---|---|---|---|---|---|---|
| | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | 0 | -2 | -1 | -2 | -2 | -1 | -1.33 | 0.82 |
| Annexin pos./ PI neg. | 3 | 1 | 0 | 0 | 1 | -1 | 0.67 | 1.37 |

Measurement day 3

| | 05C-3 | | | | | | | |
|---|---|---|---|---|---|---|---|---|
| | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | 0 | 1 | -2 | -3 | -3 | -3 | -1.67 | 1.75 |
| Annexin pos./ PI neg. | 0 | -2 | 0 | 0 | 0 | 2 | 0.00 | 1.26 |

Measurement day 4

| | 05C-3 | | | | | | | |
|---|---|---|---|---|---|---|---|---|
| | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | 0 | 0 | -4 | -4 | 0 | -1 | -1.50 | 1.97 |
| Annexin pos./ PI neg. | 1 | 2 | 0 | 2 | -1 | -2 | 0.33 | 1.63 |

Measurement day 5

| | 05C-3 | | | | | | | |
|---|---|---|---|---|---|---|---|---|
| | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | 0 | 0 | -6 | -5 | -2 | -8 | -3.50 | 3.33 |
| Annexin pos./ PI neg. | 1 | 0 | -1 | 0 | -4 | 4 | 0.00 | 2.61 |

Mean and StDeviation

| | day4 6-Thio-GTP (n=6) | 05B-0 (n=4) | 05B-1 (n=4) | 05C-0 (n=6) | 05C-1 (n=6) | 05C-2 (n=6) | 05C-3 (n=6) |
|---|---|---|---|---|---|---|---|
| Annexin pos./ PI pos. | 1.17 | 22 | 5.75 | 0.33 | -3.17 | -1.83 | -1.5 |
| StDev | 5.12 | 6.98 | 1.5 | 2.42 | 3.49 | 2.64 | 1.97 |
| Annexin pos./ PI neg. | -2.33 | -1.25 | 1.75 | 0.17 | -0.33 | 0 | 0.33 |
| StDev | 5.35 | 5.97 | 2.22 | 1.6 | 1.97 | 1.41 | 1.63 |

SEM

| | day4 6-Thio-GTP (n=6) | 05B-0 (n=4) | 05B-1 (n=4) | 05C-0 (n=6) | 05C-1 (n=6) | 05C-2 (n=6) | 05C-3 (n=6) |
|---|---|---|---|---|---|---|---|
| Annexin pos./ PI pos. | 1.17 | 22 | 5.75 | 0.33 | -3.17 | -1.83 | -1.5 |
| SEM | 2.1 | 3.49 | 0.75 | 0.99 | 1.42 | 1.08 | 0.8 |
| Annexin pos./ PI neg. | -2.33 | -1.25 | 1.75 | 0.17 | -0.33 | 0 | 0.33 |
| SEM | 2.18 | 2.99 | 1.11 | 0.65 | 0.8 | 0.58 | 0.66 |

Figure 6 H

Measurement day 1

| | 06D-1 | | | | | | | |
|---|---|---|---|---|---|---|---|---|
| | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | 0 | -1 | 1 | 1 | 0 | 6 | 1.17 | 2.48 |
| Annexin pos./ PI neg. | -2 | -3 | 0 | 0 | 1 | 2 | -0.33 | 1.86 |

Measurement day 2

| | 06D-1 | | | | | | | |
|---|---|---|---|---|---|---|---|---|
| | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | -1 | -3 | -1 | 1 | -2 | 0 | -1.00 | 1.41 |
| Annexin pos./ PI neg. | 2 | -2 | 0 | 0 | 3 | 0 | 0.50 | 1.76 |

Measurement day 3

| | 06D-1 | | | | | | | |
|---|---|---|---|---|---|---|---|---|
| | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | -1 | 2 | 0 | 1 | -2 | -2 | -0.33 | 1.63 |
| Annexin pos./ PI neg. | -1 | -1 | 0 | 0 | 2 | 3 | 0.50 | 1.64 |

Measurement day 4

| | 06D-1 | | | | | | | |
|---|---|---|---|---|---|---|---|---|
| | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | -1 | 0 | -1 | 1 | 0 | 2 | 0.17 | 1.17 |
| Annexin pos./ PI neg. | 0 | 1 | -1 | 0 | 0 | -3 | -0.50 | 1.38 |

Measurement day 5

| | 06D-1 | | | | | | | |
|---|---|---|---|---|---|---|---|---|
| | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | 2 | -3 | -6 | -4 | -2 | -5 | -3.00 | 2.83 |
| Annexin pos./ PI neg. | 1 | -2 | -1 | 1 | -3 | 7 | 0.50 | 3.56 |

Mean and StDeviation

| | 06D-1 (n=6) | 06D-3 (n=6) | 06D-6 (n=6) | 06D-12 (n=6) | 06D-14 (n=6) | 06D-22 (n=6) | 06D-30 (n=6) |
|---|---|---|---|---|---|---|---|
| Annexin pos./ PI pos. | 0.17 | 0.67 | -0.5 | -0.5 | 1 | 3.17 | 0.83 |
| StDev | 1.17 | 3.88 | 7.4 | 2.88 | 1.9 | 3.54 | 2.32 |
| Annexin pos./ PI neg. | -0.5 | -0.67 | -3.5 | -0.17 | 1 | 0.5 | 0.67 |
| StDev | 1.38 | 1.21 | 5.75 | 1.72 | 2.68 | 2.07 | 1.86 |

SEM

| | 06D-1 (n=6) | 06D-3 (n=6) | 06D-6 (n=6) | 06D-12 (n=6) | 06D-14 (n=6) | 06D-22 (n=6) | 06D-30 (n=6) |
|---|---|---|---|---|---|---|---|
| Annexin pos./ PI pos. | 0.17 | 0.67 | -0.5 | -0.5 | 1 | 3.17 | 0.83 |
| SEM | 0.48 | 0.58 | 3.02 | 1.18 | 0.78 | 1.45 | 0.95 |
| Annexin pos./ PI neg. | -0.5 | -0.67 | -3.5 | -0.17 | 1 | 0.5 | 0.67 |
| SEM | 0.56 | 0.49 | 2.33 | 0.7 | 1.09 | 0.85 | 0.76 |

Figure 6 I

Measurement day 1

|  | 06D-3 Buffy1 11.04.06 | Buffy2 11.04.06 | Buffy1 19.04.06 | Buffy2 19.04.06 | Buffy 1 02.05.06 | Buffy F 03.05.06 | mean | StDev |
|---|---|---|---|---|---|---|---|---|
| Annexin pos./ PI pos. | 0 | 1 | 1 | 0 | 1 | 1 | 0.67 | 0.52 |
| Annexin pos./ PI neg. | -1 | 0 | -1 | 1 | 0 | -1 | -0.33 | 0.82 |

Measurement day 2

|  | 06D-3 Buffy1 11.04.06 | Buffy2 11.04.06 | Buffy1 19.04.06 | Buffy2 19.04.06 | Buffy 1 02.05.06 | Buffy F 03.05.06 | mean | StDev |
|---|---|---|---|---|---|---|---|---|
| Annexin pos./ PI pos. | 1 | -3 | -2 | 0 | -2 | -1 | -1.17 | 1.47 |
| Annexin pos./ PI neg. | 1 | 0 | 1 | 0 | 2 | -2 | 0.33 | 1.37 |

Measurement day 3

|  | 06D-3 Buffy1 11.04.06 | Buffy2 11.04.06 | Buffy1 19.04.06 | Buffy2 19.04.06 | Buffy 1 02.05.06 | Buffy F 03.05.06 | mean | StDev |
|---|---|---|---|---|---|---|---|---|
| Annexin pos./ PI pos. | 0 | 1 | -3 | -2 | -2 | -3 | -1.50 | 1.64 |
| Annexin pos./ PI neg. | 1 | -2 | 1 | 0 | 2 | 0 | 0.33 | 1.37 |

Measurement day 4

|  | 06D-3 Buffy1 11.04.06 | Buffy2 11.04.06 | Buffy1 19.04.06 | Buffy2 19.04.06 | Buffy 1 02.05.06 | Buffy F 03.05.06 | mean | StDev |
|---|---|---|---|---|---|---|---|---|
| Annexin pos./ PI pos. | 0 | 0 | -5 | 0 | 2 | 7 | 0.67 | 3.88 |
| Annexin pos./ PI neg. | 0 | 0 | -1 | 1 | -2 | -2 | -0.67 | 1.21 |

Measurement day 5

|  | 06D-3 Buffy1 11.04.06 | Buffy2 11.04.06 | Buffy1 19.04.06 | Buffy2 19.04.06 | Buffy 1 02.05.06 | Buffy F 03.05.06 | mean | StDev |
|---|---|---|---|---|---|---|---|---|
| Annexin pos./ PI pos. | -1 | -2 | -7 | -11 | 1 | 8 | -2.00 | 6.57 |
| Annexin pos./ PI neg. | 0 | -2 | 0 | 0 | -9 | -6 | -2.83 | 3.82 |

Mean and StDeviation

|  | day5 6-Thio-GTP (n=6) | 05B-0 (n=4) | 05B-1 (n=4) | 05C-0 (n=6) | 05C-1 (n=6) | 05C-2 (n=6) | 05C-3 (n=6) | 06D-1 (n=6) |
|---|---|---|---|---|---|---|---|---|
| Annexin pos./ PI pos. | -0.17 | 19.25 | -0.25 | -2.67 | -6.83 | -6.67 | -3.5 | -3 |
| StDev | 3.31 | 8.3 | 5.74 | 2.73 | 5.19 | 5.05 | 3.33 | 2.83 |
| Annexin pos./ PI neg. | -4 | -4.75 | -0.5 | 1.5 | 1.5 | 0.67 | 0 | 0.5 |
| StDev | 6.2 | 3.3 | 4.2 | 3.73 | 4.04 | 3.61 | 2.61 | 3.56 |

SEM

|  | day5 6-Thio-GTP (n=6) | 05B-0 (n=4) | 05B-1 (n=4) | 05C-0 (n=6) | 05C-1 (n=6) | 05C-2 (n=6) | 05C-3 (n=6) | 06D-1 (n=6) |
|---|---|---|---|---|---|---|---|---|
| Annexin pos./ PI pos. | -0.17 | 19.25 | -0.25 | -2.67 | -6.83 | -6.67 | -3.5 | -3 |
| SEM | 1.35 | 4.15 | 2.87 | 1.11 | 2.12 | 2.06 | 1.36 | 1.16 |
| Annexin pos./ PI neg. | -4 | -4.75 | -0.5 | 1.5 | 1.5 | 0.67 | 0 | 0.5 |
| SEM | 2.53 | 1.65 | 2.1 | 1.52 | 1.65 | 1.47 | 1.07 | 1.45 |

Figure 6 J

Measurement day 1

|  | 06D-6 | | | | | | | |
|---|---|---|---|---|---|---|---|---|
|  | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | -1 | 0 | -1 | -1 | 0 | 1 | -0.33 | 0.82 |
| Annexin pos./ PI neg. | -1 | -2 | -2 | 0 | -1 | -1 | -1.17 | 0.75 |

Measurement day 2

|  | 06D-6 | | | | | | | |
|---|---|---|---|---|---|---|---|---|
|  | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | 1 | -3 | -3 | -1 | -2 | -2 | -1.67 | 1.51 |
| Annexin pos./ PI neg. | 2 | -1 | 1 | 1 | 2 | 0 | 0.83 | 1.17 |

Measurement day 3

|  | 06D-6 | | | | | | | |
|---|---|---|---|---|---|---|---|---|
|  | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | 0 | 0 | -2 | -4 | -1 | -1 | -1.33 | 1.51 |
| Annexin pos./ PI neg. | 1 | -1 | 1 | 0 | 2 | -1 | 0.33 | 1.21 |

Measurement day 4

|  | 06D-6 | | | | | | | |
|---|---|---|---|---|---|---|---|---|
|  | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | 1 | 1 | -5 | -12 | 2 | 10 | -0.50 | 7.40 |
| Annexin pos./ PI neg. | 0 | 0 | -1 | -2 | -3 | -15 | -3.50 | 5.75 |

Measurement day 5

|  | 06D-6 | | | | | | | |
|---|---|---|---|---|---|---|---|---|
|  | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | 3 | 0 | -7 | -7 | 2 | 4 | -0.83 | 4.96 |
| Annexin pos./ PI neg. | 3 | -3 | 0 | 1 | -12 | -16 | -4.50 | 7.71 |

Mean and StDeviation

|  | 06D-3 (n=6) | 06D-6 (n=6) | 06D-12 (n=6) | 06D-14 (n=6) | 06D-22 (n=6) | 06D-30 (n=6) |
|---|---|---|---|---|---|---|
| Annexin pos./ PI pos. | -2 | -0.83 | -2.5 | -1.17 | 5 | -0.5 |
| StDev | 6.57 | 4.96 | 5.28 | 4.92 | 6.39 | 5.65 |
| Annexin pos./ PI neg. | -2.83 | -4.5 | 0.67 | 0.67 | -0.5 | 1.33 |
| StDev | 3.82 | 7.71 | 5.35 | 4.97 | 6.16 | 4.63 |

SEM

|  | 06D-3 (n=6) | 06D-6 (n=6) | 06D-12 (n=6) | 06D-14 (n=6) | 06D-22 (n=6) | 06D-30 (n=6) |
|---|---|---|---|---|---|---|
| Annexin pos./ PI pos. | -2 | -0.83 | -2.5 | -1.17 | 5 | -0.5 |
| SEM | 2.68 | 2.02 | 2.16 | 2 | 2.61 | 2.31 |
| Annexin pos./ PI neg. | -2.83 | -4.5 | 0.67 | 0.67 | -0.5 | 1.33 |
| SEM | 1.56 | 3.35 | 2.18 | 2.03 | 2.51 | 1.89 |

Figure 6 K

Measurement day 1

|  | 06D-12 | | | | | | | |
|---|---|---|---|---|---|---|---|---|
|  | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | -1 | -1 | 1 | -3 | 1 | 0 | -0.50 | 1.52 |
| Annexin pos./ PI neg. | -1 | -1 | -1 | -2 | 1 | 0 | -0.67 | 1.03 |

Measurement day 2

|  | 06D-12 | | | | | | | |
|---|---|---|---|---|---|---|---|---|
|  | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | 1 | -4 | -3 | 0 | -2 | 0 | -1.33 | 1.97 |
| Annexin pos./ PI neg. | 2 | -1 | 0 | 0 | 2 | -1 | 0.33 | 1.37 |

Measurement day 3

|  | 06D-12 | | | | | | | |
|---|---|---|---|---|---|---|---|---|
|  | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | 0 | 1 | -1 | -2 | -2 | -1 | -0.83 | 1.17 |
| Annexin pos./ PI neg. | 1 | -1 | 1 | 0 | 1 | 3 | 0.83 | 1.33 |

Measurement day 4

|  | 06D-12 | | | | | | | |
|---|---|---|---|---|---|---|---|---|
|  | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | 0 | 1 | -6 | -1 | 2 | 1 | -0.50 | 2.88 |
| Annexin pos./ PI neg. | 2 | 0 | 0 | 1 | -1 | -3 | -0.17 | 1.72 |

Measurement day 5

|  | 06D-12 | | | | | | | |
|---|---|---|---|---|---|---|---|---|
|  | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | 6 | -2 | -8 | -6 | 1 | -6 | -2.50 | 5.28 |
| Annexin pos./ PI neg. | 5 | 0 | 0 | 2 | -9 | 6 | 0.67 | 5.35 |

Figure 6 L

Measurement day 1

|  | 06D-14 | | | | | | | |
|---|---|---|---|---|---|---|---|---|
|  | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | -2 | 0 | 0 | 0 | -1 | 1 | -0.33 | 1.03 |
| Annexin pos./ PI neg. | -1 | 0 | -1 | 0 | 1 | 1 | 0.00 | 0.89 |

Measurement day 2

|  | 06D-14 | | | | | | | |
|---|---|---|---|---|---|---|---|---|
|  | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | 3 | -2 | -6 | 2 | 1 | 0 | -0.33 | 3.27 |
| Annexin pos./ PI neg. | 0 | -1 | -1 | 0 | 3 | -2 | -0.17 | 1.72 |

Measurement day 3

|  | 06D-14 | | | | | | | |
|---|---|---|---|---|---|---|---|---|
|  | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | 3 | 3 | -2 | -1 | -1 | -1 | 0.17 | 2.23 |
| Annexin pos./ PI neg. | 1 | -2 | 0 | 0 | 1 | 2 | 0.33 | 1.37 |

Measurement day 4

|  | 06D-14 | | | | | | | |
|---|---|---|---|---|---|---|---|---|
|  | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | 1 | 1 | -2 | 0 | 3 | 3 | 1.00 | 1.90 |
| Annexin pos./ PI neg. | 4 | 2 | 1 | 2 | 1 | -4 | 1.00 | 2.68 |

Measurement day 5

|  | 06D-14 | | | | | | | |
|---|---|---|---|---|---|---|---|---|
|  | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | 7 | -1 | -7 | -2 | 1 | -5 | -1.17 | 4.92 |
| Annexin pos./ PI neg. | 6 | 0 | -1 | 3 | -8 | 4 | 0.67 | 4.97 |

Figure 6 M

Measurement day 1

| | 06D-22 | | | | | | | |
|---|---|---|---|---|---|---|---|---|
| | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | -1 | 1 | 0 | 2 | 0 | 0 | 0.33 | 1.03 |
| Annexin pos./ PI neg. | -1 | 0 | -1 | 0 | 2 | 0 | 0.00 | 1.10 |

Measurement day 2

| | 06D-22 | | | | | | | |
|---|---|---|---|---|---|---|---|---|
| | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | 1 | -1 | 0 | 3 | 0 | -1 | 0.33 | 1.51 |
| Annexin pos./ PI neg. | 0 | 0 | 0 | 1 | 1 | 0 | 0.33 | 0.52 |

Measurement day 3

| | 06D-22 | | | | | | | |
|---|---|---|---|---|---|---|---|---|
| | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | 2 | 1 | 1 | 0 | 2 | -2 | 0.67 | 1.51 |
| Annexin pos./ PI neg. | 3 | -1 | 0 | 0 | 2 | 0 | 0.67 | 1.51 |

Measurement day 4

| | 06D-22 | | | | | | | |
|---|---|---|---|---|---|---|---|---|
| | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | 3 | 1 | -2 | 3 | 8 | 6 | 3.17 | 3.54 |
| Annexin pos./ PI neg. | 3 | 2 | 1 | 1 | -2 | -2 | 0.50 | 2.07 |

Measurement day 5

| | 06D-22 | | | | | | | |
|---|---|---|---|---|---|---|---|---|
| | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | 11 | 0 | -4 | 3 | 12 | 8 | 5.00 | 6.39 |
| Annexin pos./ PI neg. | 7 | 3 | 1 | 2 | -8 | -8 | -0.50 | 6.16 |

Figure 6 N

Measurement day 1

| | 06D-30 | | | | | | | |
|---|---|---|---|---|---|---|---|---|
| | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | -3 | 0 | 1 | 3 | 0 | 0 | 0.17 | 1.94 |
| Annexin pos./ PI neg. | -4 | 1 | 0 | 1 | 2 | 0 | 0.00 | 2.10 |

Measurement day 2

| | 06D-30 | | | | | | | |
|---|---|---|---|---|---|---|---|---|
| | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | 2 | -3 | 0 | 3 | -2 | -1 | -0.17 | 2.32 |
| Annexin pos./ PI neg. | 0 | 1 | 1 | 0 | -1 | -2 | -0.17 | 1.17 |

Measurement day 3

| | 06D-30 | | | | | | | |
|---|---|---|---|---|---|---|---|---|
| | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | 1 | 0 | -2 | 5 | 0 | 1 | 0.83 | 2.32 |
| Annexin pos./ PI neg. | 1 | 1 | 0 | 1 | 1 | 2 | 1.00 | 0.63 |

Measurement day 4

| | 06D-30 | | | | | | | |
|---|---|---|---|---|---|---|---|---|
| | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | 2 | 1 | -3 | 4 | 0 | 1 | 0.83 | 2.32 |
| Annexin pos./ PI neg. | 2 | 1 | 1 | 2 | 1 | -3 | 0.67 | 1.86 |

Measurement day 5

| | 06D-30 | | | | | | | |
|---|---|---|---|---|---|---|---|---|
| | Buffy1 11.04.06 | Buffy2 11.04.06 | Buffy1 19.04.06 | Buffy2 19.04.06 | Buffy 1 02.05.06 | Buffy F 03.05.06 | mean | StDev |
| Annexin pos./ PI pos. | 8 | 0 | -6 | -3 | 4 | -6 | -0.50 | 5.65 |
| Annexin pos./ PI neg. | 6 | 2 | 0 | 2 | -7 | 5 | 1.33 | 4.63 |

| ID | Structure | Formula |
|---|---|---|
|  | [structure of 6-thioguanosine with triacetyl and thioacetamide-hexyl substituent] | In patent referred as: V4=TWI 107/7= 2',3',5'-Triacetil-N-2-(6"-tioacetammide-esil)-6-tioguanosina |
| V3 | [structure of 6-thioguanosine with triacetyl and aminohexyl substituent] | In patent referred as: V3=twi 71/2=2',3',5', O-Triacetil-N-2-(acetil-6"-amminoesil)-guanosina |
| PROBE | [structure of 6-thio-GTP conjugated via EDA linker to TAMRA] | In patent referred as: V5=BMB=TAMRA-EDA-6-tio-GTP |

Figure 7 B
| ID | Structure | Formula |
|---|---|---|
| 5A-0 | 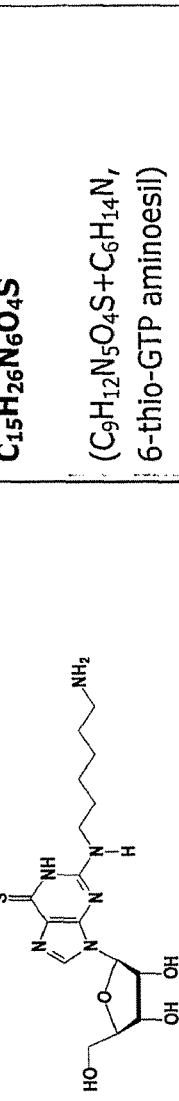 | $C_{15}H_{26}N_6O_4S$<br><br>$(C_9H_{12}N_5O_4S+C_6H_{14}N,$ 6-thio-GTP aminoesil)<br><br>(In patent referred as: V2=TWI 35/1=n-2-(6''-amminoesil)-guanosina) |
| 5A-1 | 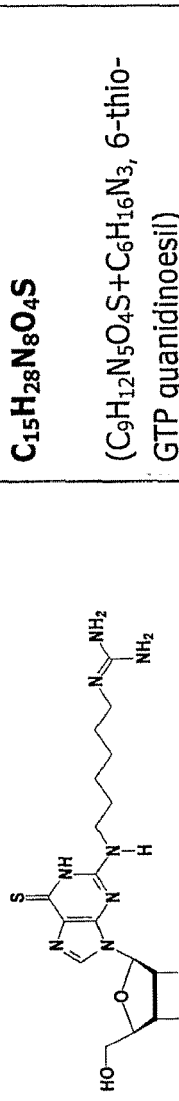 | $C_{15}H_{28}N_8O_4S$<br><br>$(C_9H_{12}N_5O_4S+C_6H_{16}N_3,$ 6-thio-GTP guanidinoesil) |
| 5A-2 | 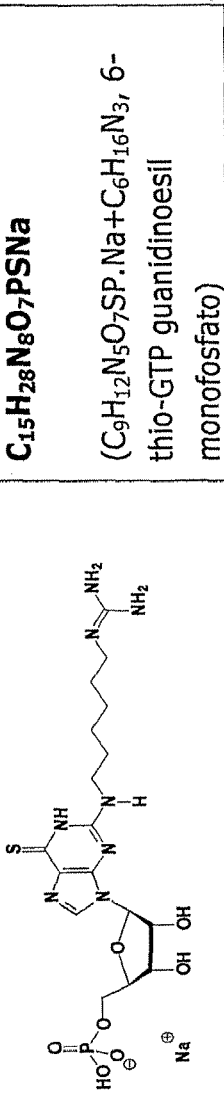 | $C_{15}H_{28}N_8O_7PSNa$<br><br>$(C_9H_{12}N_5O_7SP.Na+C_6H_{16}N_3,$ 6-thio-GTP guanidinoesil monofosfato) |

Figure 7 C
| ID | Structure | Formula |
|---|---|---|
| 5A-3 | 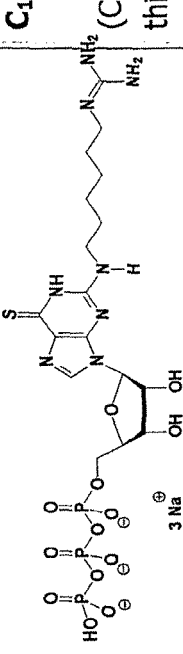 | $C_{15}H_{28}N_8O_{13}P_3SNa$<br>($C_9H_{12}N_5O_{13}SP_3 \cdot Na + C_6H_{16}N_3$, 6-thio-GTP guanidinoesil trifosfato) |
| 5B-0 | 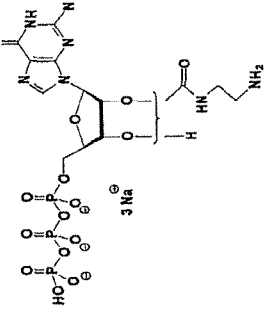 | $C_{12}H_{19}N_7O_{14}P_3SNa_3$<br>($C_9H_{12}N_5O_{13}P_3SNa_3 + C_3H_7N_2O$, 6-Thio-GTP+EDA)<br><br>(In Patent referred as:<br>V1=BMB20=EDA-6-Tio-GTP) |

Figure 7 D

| ID | Structure | Formula |
|---|---|---|
| 5B-1 | 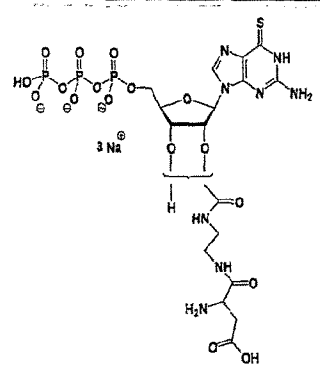 | $C_{16}H_{24}N_8O_{17}P_3SNa_3$<br><br>$(C_9H_{12}N_5O_{13}P_3SNa_3+C_7H_{12}N_3O_4$,<br>6-Thio-<br>GTP+EDA+Acido aspartico) |
| 5B-2 | 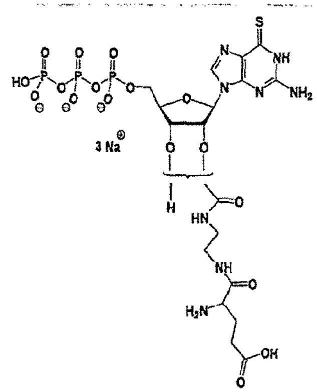 | $C_{17}H_{26}N_8O_{17}P_3SNa_3$<br><br>$(C_9H_{12}N_5O_{13}P_3SNa_3+C_8$<br>$H_{14}N_3O_4$,<br>6-Thio-<br>GTP+EDA+Acido glutammico) |

Figure 7 E
| ID | Structure | Formula |
|---|---|---|
| 5B-3 | 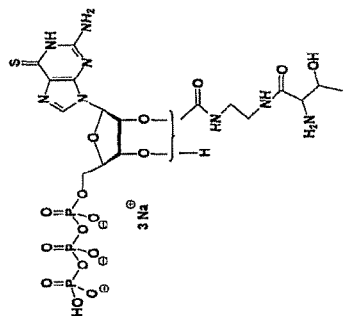 | $C_{16}H_{26}N_8O_{16}P_3SNa_3$<br><br>($C_9H_{12}N_5O_{13}P_3SNa_3 + C_7H_{14}N_3O_3$, 6-Thio-GTP+EDA+Treonina) |
| igla | Structure | Formula |
|---|---|---|
| 5C-1 | 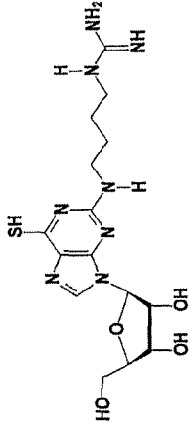 | $C_{13}H_{24}N_8O_4S$<br><br>($C_9H_{12}N_5O_4S + C_4H_{12}N_3$, 6-thio-GTP guanidinobutyl) |

| igla | Structure | Formula |
|---|---|---|
| 5C-2 | 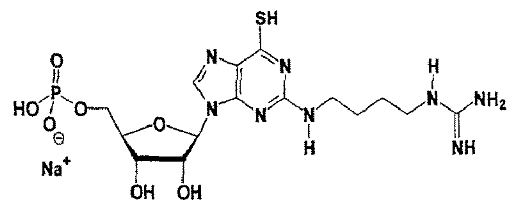 | $C_{13}H_{24}N_8O_7PSNa$<br><br>$(C_9H_{12}N_5O_7SP.Na+C_4H_{12}N_3,$ 6-thio-GTP guanidinobutyil monofosfate) |
| 5C-3 | 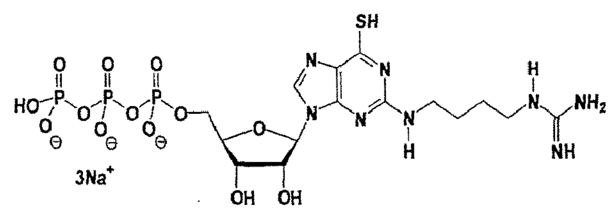 | $C_{13}H_{24}N_8O_{13}P_3SNa$<br><br>$(C_9H_{12}N_5O_{13}SP_3.Na+C_4H_{12}N_3,$ 6-thio-GTP guanidinobutyl trifosfate) |

Figure 7 F

ANALOGOUS COMPOUNDS OF 6-THIOGUANOSINE TRIPHOSPHATE, THEIR USE IN MEDICAL FIELDS AND PROCESSES FOR THEIR PREPARATION

RELATED APPLICATIONS

This application is the U.S. National Stage of International Application No. PCT/IE2006/000077, filed 24 Jul. 2006, published in English, and claims priority under 35 U.S.C. §119 or 365 to Italian Application No. RM2005A000391, filed 22 Jul. 2005 and to Ireland Application No. 2006/0448, filed 14 Jun. 2006.

The present invention relates to analogous compounds of 6-thioguanosine triphosphate, their use in medical field and process for their preparation.

Particularly, the invention refers to the therapeutic use of analogous compounds of 6-thioguanosine triphosphate for example as immunosuppressant for the prevention of rejection of organ transplants and of post-transplant nephropathy and in the treatment of pathologies in which immune system is involved, such as, for instance, inflammatory chronic intestinal diseases, such as Crohn's disease, ulcerous rectocolitis, indeterminate colitis, or of auto-immune enteropathy, active chronic hepatitis, rheumatoid arthritis, Still's disease, systemic lupus erythematous, acquired haemolytic anaemia, idiopathic thrombocytopenia, polyarthritis nodosa, vasculitis, polyangitis, polymyositis, myasthenia gravis, sarcoidosis, lipoid nephritis, multiple sclerosis, dermatomyositis, pemphigus vulgaris, primary biliary cirrhosis, primary sclerosing cholangitis, recurrent multiform erythema, chronic actinic dermatitis, gangrenous hypoderm, ptyriasis rubra, Wegener's granulomatosis, cutaneous vasculitis, atopic dermatitis, psoriasis, pimply pemphigoid and, in general, in the immunosuppressive treatment in addition to radiotherapy, corticosteroids and other cytotoxic agents. The latter also involves immunosuppressive therapy after organ transplantation (e.g. kidney, heart, lung, pancreas and liver transplantation).

The cells involved in the inflammatory immune response are able to survive at the inflammatory site, however, after completion of such response, the majority of cells must "die" to maintain the homeostasis of organism (Boise, 1995). Since the uncontrolled lymphocyte proliferation may cause the development of inflammatory chronic pathologies, the immune system controls the depletion of activated lymphocytes by a process named apoptosis (programmed cell death).

This would assume a particular importance for the immune system of the mucosa, since the apoptosis resistance of lamina propria cells can lead to a chronic inflammatory response at the intestinal level (Tiede, 2003).

The activation of the mucosal immune system plays a key role in the pathogenesis of Crohn's disease. Particularly, pro-inflammatory cytokines produced by T lymphocytes and macrophages, in particular interleukine-6 (IL-6) and interleukine-12 (IL-12), may cause T lymphocytes resistance against apoptosis, which in its turn provokes an intestinal accumulation of lymphocytes and establishes a long-lasting disease (Tiede, 2003).

The lymphocytes activation starts with two signals: the specific binding of antigens to the TCR (T cell receptor) and a second co-stimulatory signal represented by transmembrane proteins, such as CD28 (Maltzman, 2003). It has been shown that co-stimulation with CD28 enhances in vitro survival of activated T lymphocytes; in fact, CD28 induces an enhanced production of interleukine-2 (IL-2) acting as extrinsic factor for T lymphocytes survival, and the intrinsic ability of T lymphocytes to be resistant against apoptosis (Boise, 1995 bis). This occurs since CD28 action is associated with the expression of an anti-apoptotic gene, named bcl-$x_L$ gene (Khoshnan, 2000; Noel, 1996).

The steps through which an inhibition of apoptosis takes place, will be synthesized as follows, as shown in FIG. 1:

- CD28 acts through its cytoplasmaic portion with a complex of "adaptor" proteins and with a molecule, named Vav (Frauwirth, 2002);
- Vav acts as guanosine nucleotide exchange factor (GEF) for another molecule named Rac1 (Frauwirth, 2002);
- Rac1, a small GTPase, in such a way switches between an inactive state bound to GDP and an active state bound to GTP (Frauwirth, 2002);
- Activated Rac1, in its turn, leads to the activation of kinases (IKK) that phosphorylate the NF-κB inhibitory proteins (like I-κB alfa) (Marinari, 2002) through MEK phosphorylation;
- Thus, NF-κB is not anymore retained in an inactive form in the cytosol but is able to translocate to nucleus where induces bcl-$x_L$ expression (Khoshnan, 2000);
- Further, activated Rac1 stimulates the activation of a protein belonging to the STAT family (Signal Transducers and Activators of Transcription), that is STAT-3, thus inducing its translocation to the nucleus and the corresponding expression of STAT-3 dependent genes (Faruqi, 2001). In particular, STAT-3 induces bcl-$x_L$ expression thus contributing to the resistance against apoptosis and to the accumulation of T lymphocytes in the inflamed mucosa during the course of Crohn's disease (Mudter, 2003). On the other hand, the study of intestinal T lymphocytes has pointed out that STAT-3 is steadily activated in patients with Crohn's disease, but not in healthy voluntaries (Lovato 2003).

Rac1, together with RhoA and Cdc42, belongs to the Rho family which is a superfamily of small G protein characterized in that they are able to bind guanosine nucleotides and to regulate many cellular responses. They cycle between an inactive state, when bound to GDP, to an active state with GTP in place of GDP. This reaction is sustained upon guanosine nucleotide exchange factors named GEFs (like Vav). The binding with GTP induces a conformational change, which allows Rac1 and other GTPases to bind to their effectors. The action of other proteins called GTPase-activating protein (GAPs) stimulates the innate GTPase activity of these small G proteins and causes them to turn back to their GDP bound inactive state. Rac1, as in general all GTPase belonging to the Rho family, plays an important role in the mitogenesis processes, proliferation, and invasivity, since it stimulates alterations of the gene expression, in the present case of the gene bcl-$x_L$, modulating the activity of transcription factors, such as, in the present case, NF-κB and STAT-3 (Van Aelst, 1997).

Azathioprine is regarded as "gold standard" of the immunosuppressive therapy of Crohn's disease, also if the mechanism of action of such active principle is still unknown. However, the inhibition of the purine nucleotide biosynthesis with suppression of DNA and RNA synthesis and downregulation of T and B lymphocytes function (Tiede 2003), is assumed to be the main therapeutic mechanism of azathioprine.

Recently, a new mechanism of action of azathioprine acting at the T lymphocytes level has been shown. After the evidence that azathioprine induces in vitro apoptosis of activated T lymphocytes and that treatment with azathioprine causes apoptosis of both circulating and lamina propria T lymphocytes of IBD patients, the specific molecular mechanisms were pointed out (Tiede 2003).

The key point is represented by the metabolite 6-thioguanosine triphosphate (6-thioGTP) which represents the real functional metabolite of the drug. Specifically, 6-thioGTP binds directly to Rac1 in place of GTP, thus blocking its activation. Such a block is highly specific for Rac1, as other GTPases belonging to the same family are not inhibited by 6-thioGTP, and this specificity suggests that the block would be correlated to the structure of Rac1 protein. The fact that an accumulation of the Rac1 guanosine nucleotide exchange factor vav was observed, is consistent with a compensatory mechanism to achieve Rac1 activation.

The block of the activation of Rac1 would result in the block of NF-κB and STAT-3, normally induced by Rac1 itself, and thus in the block of the bcl-$x_L$ gene expression, detected both at the mRNA and protein levels. Thus, azathioprine, by modulating Rac1 activity switches an anti-apoptotic co-stimulatory signal, mediated by CD28, into a pro-apoptotic signal.

This new mechanism of action is able to explain the well-known "delay" in the therapeutic effect of azathioprine, which needs a long treatment time to elicit a clinical response in such a way that benefits and clinical response were not observed earlier than 4 months of therapy. This is due to the fact that 6-thioGPT has 20-fold less affinity to Rac1 in comparison with GTP, which is normally bound to Rac1. Therefore, the azathioprine treatment needs the simultaneous and prolonged administration with high steroids doses, having remarkable side effects such as osteoporosis, diabetes, cataract.

In the light of the above it would be desirable to have at disposal new immunosuppressive drugs eliciting a faster and more efficacious therapeutic response in comparison with the already known compounds.

According to the present invention, a new class of 6-thioGTP analogous drugs able to inhibit Rac1 and characterized by greater affinity to Rac1, an higher suppression of Rac1 activity and, thus having a greater immunosuppressive power and action in comparison with the delayed effect of azathioprine treatment and a best therapeutic effect, was prepared.

It is therefore an object of the present invention to provide a class of analogous compounds of 6-thioguanosine triphosphate of general formula (I):

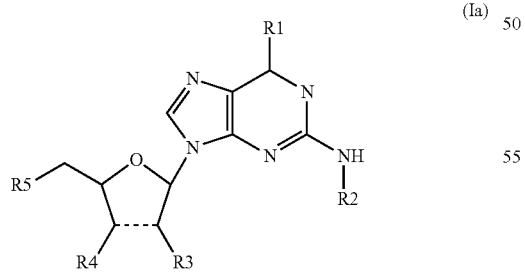

(Ia)

wherein the dashed bond in the sugar moiety can be either single or double and wherein $R_1$, $R_2$, $R_3$, $R_4$ or $R_5$, equal or different between each other, have general formula -(Int)$_m$-Ter, wherein m is between 0 and 12 and Int and Ter are Internal and Terminal building blocks, wherein Int is selected from the group consisting of

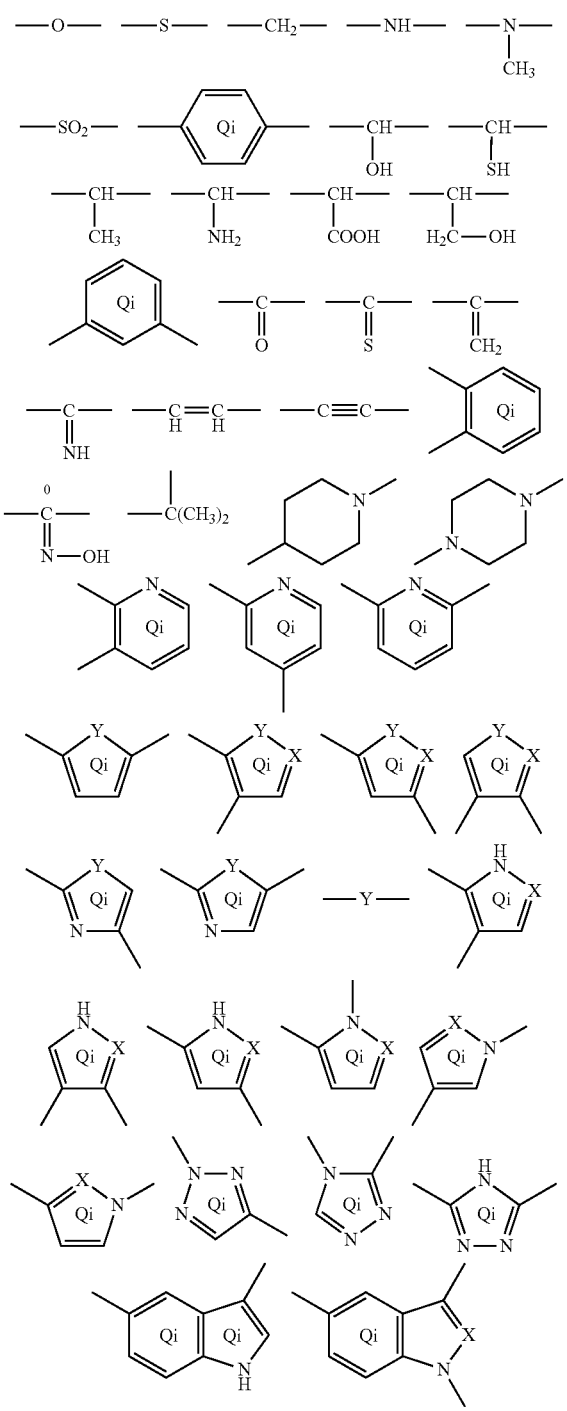

and Ter is selected from the group consisting of

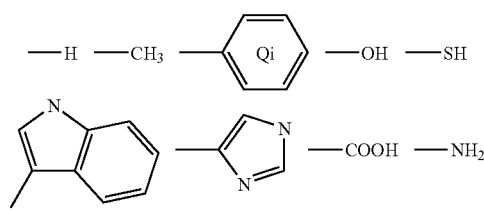

-continued

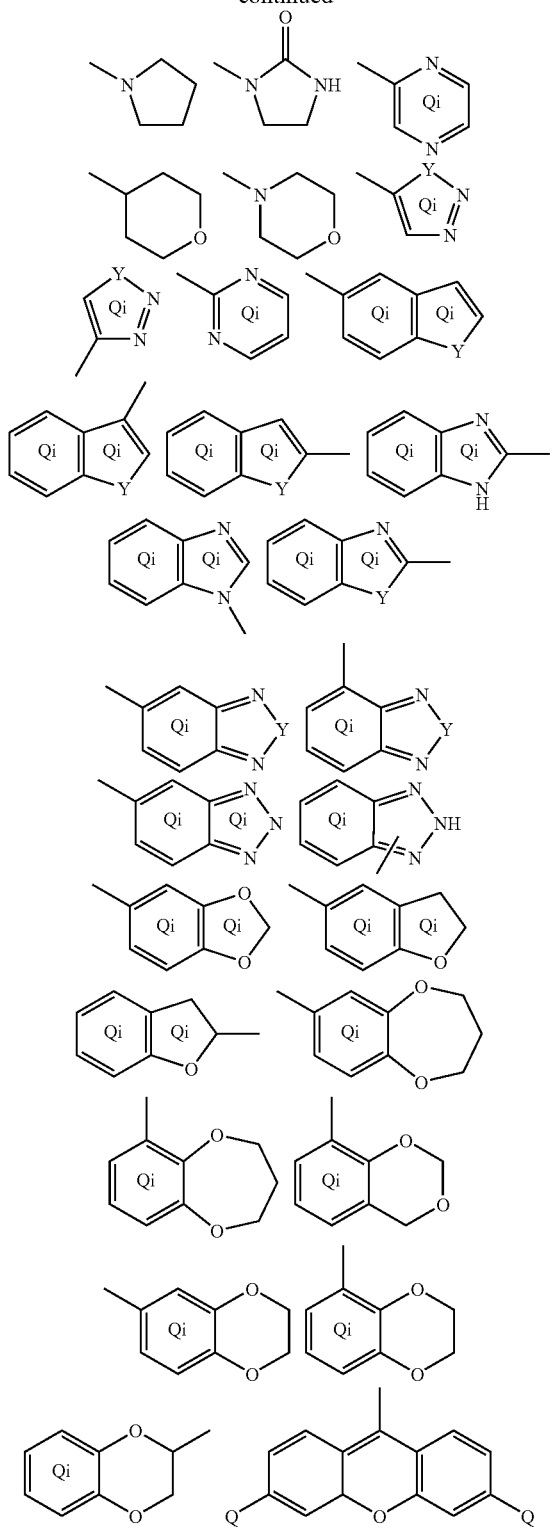

wherein X represents either carbon or nitrogen atom within aromatic ring, Y represents either oxygen or sulphur atom and an additional group Q, group Qi or groups Qi (Qi indicates that the group or several groups may be bound to any unsaturated moiety of the ring) are selected from the group consisting of —OH, —COOH, —N(CH$_3$)$_2$, —N(CH$_2$—CH$_3$)$_2$, —CO—CH$_3$, —CO—O—CH$_3$, —O—CH$_3$, —S—CH$_3$, —SO$_2$—CH$_3$, —CN, —NO$_2$ or -Halogen elements.

Alternatively R$_5$ may be

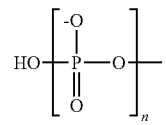

and metal and ammonium salts thereof, wherein n is between 0 and 5, or oxygen or phosphorus is partially or completely replaced by nitrogen, sulphur, methylene groups or their derivatives.

In some embodiments (particularly, but not limited to those where R$_5$ is HO—[PO$_3$]$_n$, and metal and ammonium salts thereof, wherein n is between 0 and 5, or oxygen or phosphorus is partially or completely replaced by nitrogen, sulphur, methylene groups or their derivatives) TER may be selected from the group consisting of:

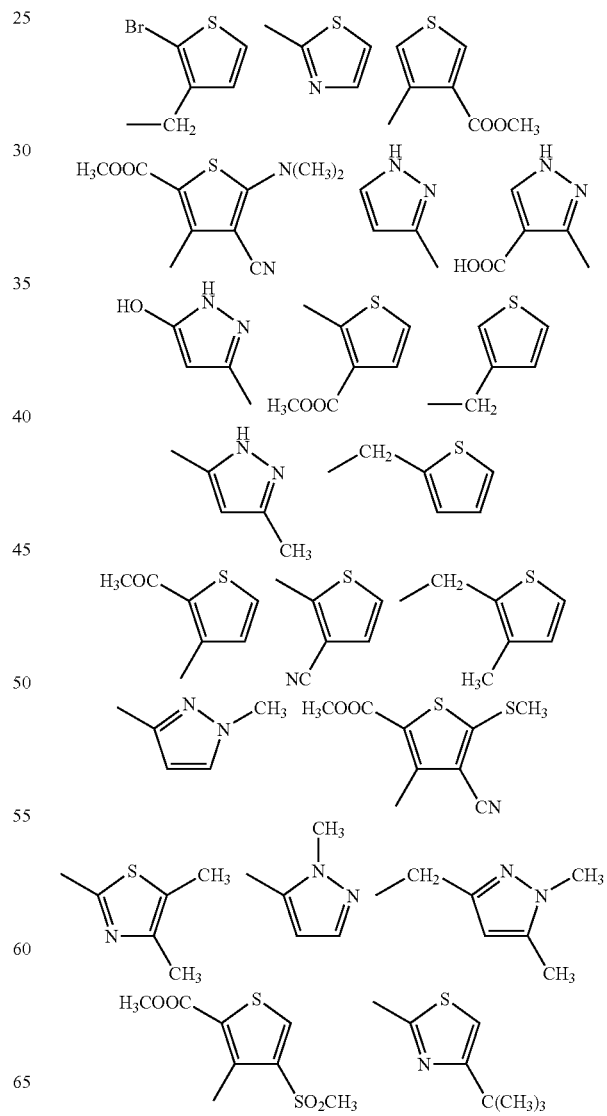

-continued

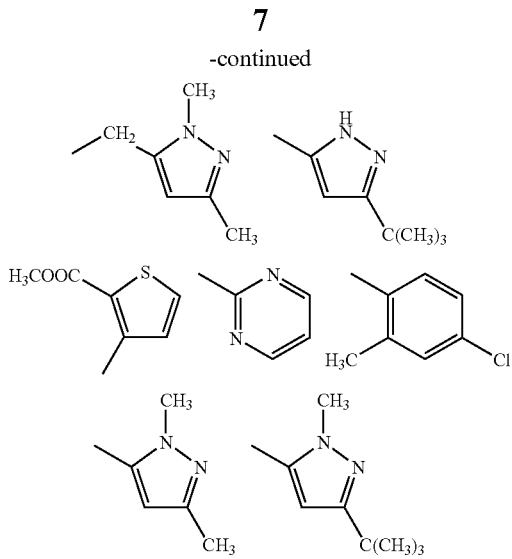

Compounds of formula (I) can be labelled, particularly with $R_3$ or $R_4$ selected from

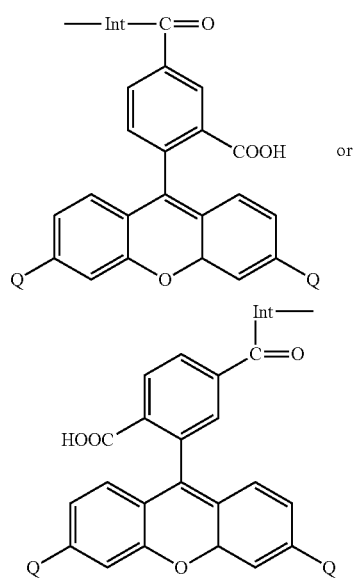

wherein Q is selected from —OH (FAM) or —N(CH$_3$)$_2$ (TAMRA).

In addition the sugar moiety of compounds of formula (I) can be selected from the group consisting of the following sugar moieties or sugar-like moieties:

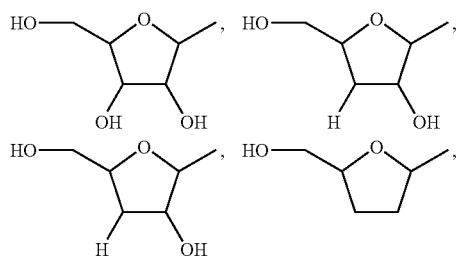

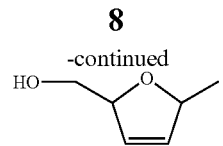

Compounds of the invention may be of the general formula (II) derived from general formula (Ia) and/or (I) where $R_1$ is [—SH] (it is understood that the Guanosine moiety may undergo keto-enol tautomeric shifts and so give rise to [=S]), $R_2$ is [—H], $R_5$ is [—(PO$_3$)$_n$—OH] and one of $R_3$ and $R_4$ is [—OH] and the other of $R_3$ and $R_4$ is [—O—CO—NH-Int$_m$-Ter] (both versions are provided in the same mixture, i.e., [—O—CO—NH-Int$_m$-Ter]: will be the same, but a proportion of the molecules will have [—O—CO—NH—-Int$_m$-Ter]: attached at $R_3$ with $R_4$ being OH, and another proportion of the molecules will have [—O—CO—NH-Int$_m$-Ter]: attached at $R_4$ with $R_3$ being OH):

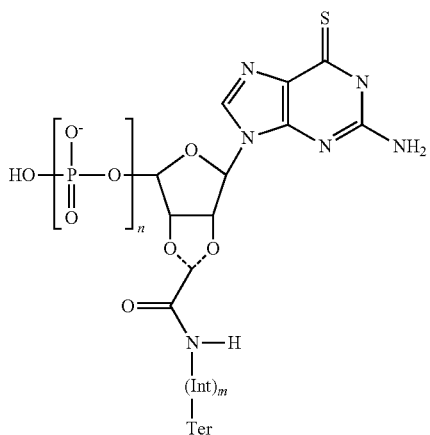

wherein n=1, 2 or 3, m is between 0 and 5, Int is selected from the group consisting of

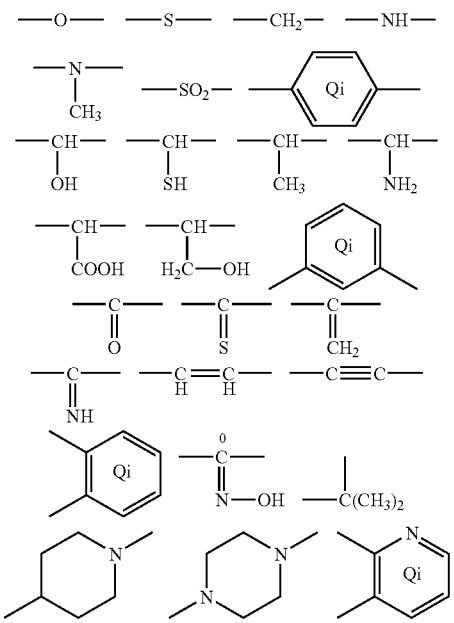

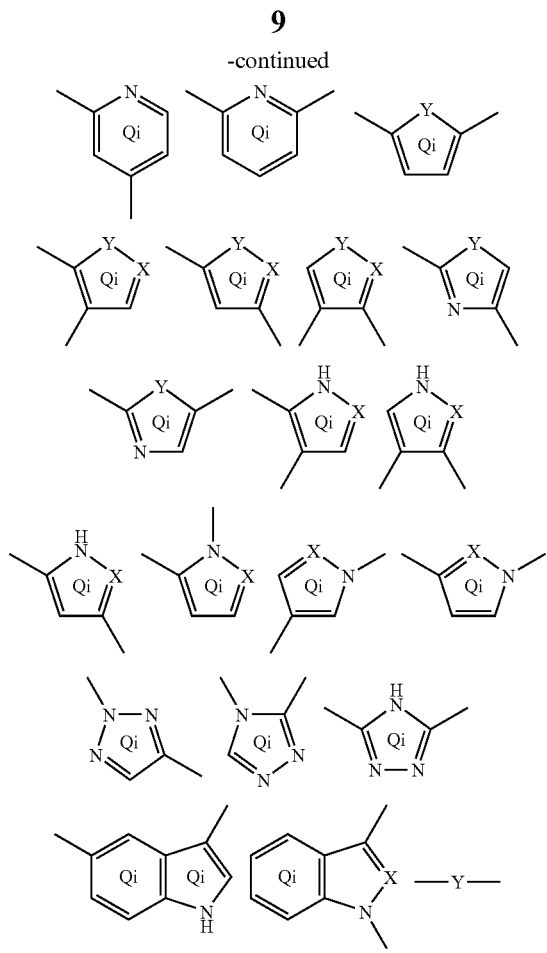

and Ter is selected from the consisting of

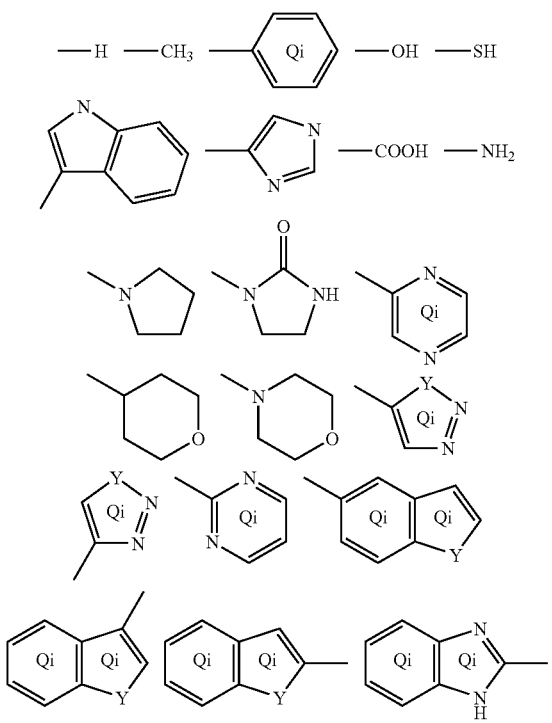

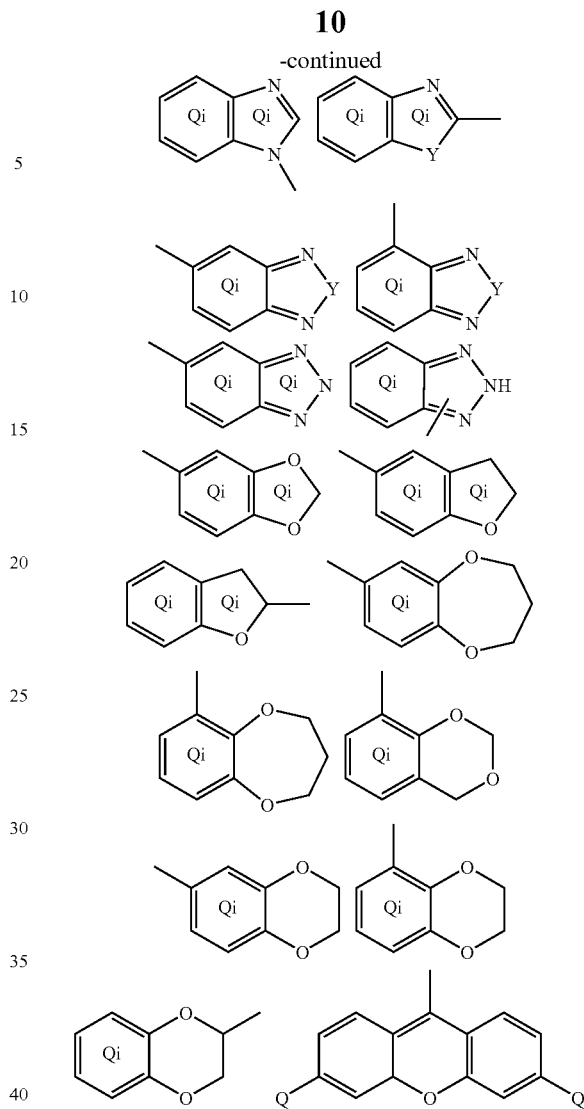

wherein X represents either carbon or nitrogen atom within aromatic ring, Y represents either oxygen or sulphur atom and an additional group Q or groups Qi (i indicating the position of any unsaturated moiety of the ring to which the group Q may be bound) are selected from the group consisting of —$CH_3$, —$C(CH_3)_3$, —OH, —COOH, —CO—$CH_3$, —CO—O—$CH_3$, —O—$CH_3$, —S—$CH_3$, —$SO_2$—$CH_3$, —$N(CH_3)_2$, —$N(CH_2$—$CH_3)_2$, —CN, —$NO_2$ or -Halogen elements.

In some embodiments of the invention of formula (I), (Ia) and (II), Ter is selected from the group consisting of

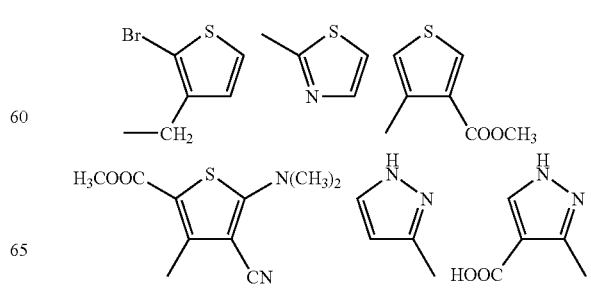

-continued

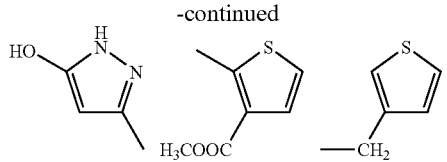

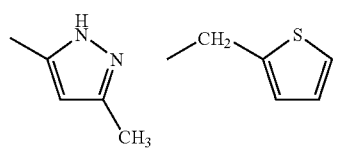

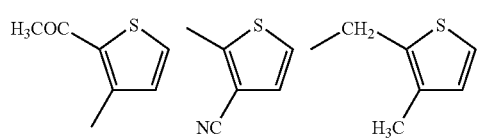

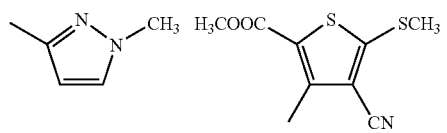

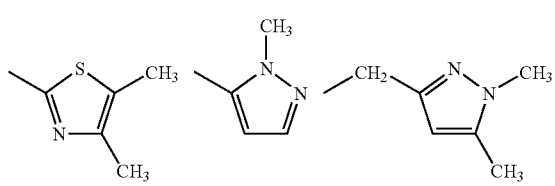

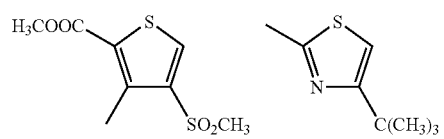

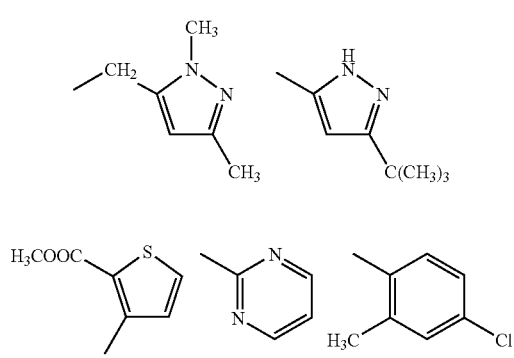

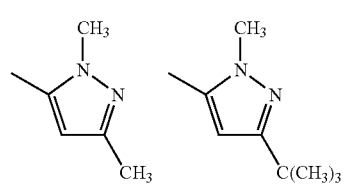

According to some embodiments of the present invention the compounds of formula (I) are the compounds described below:

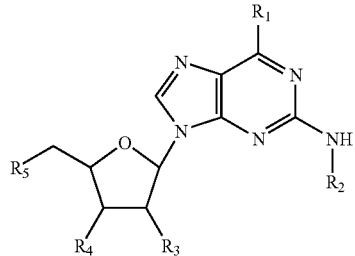

(Ia)

wherein $R_1$, $R_2$, $R_3$, $R_4$ or $R_5$, equal or different between each other, have general formula $-(Int)_m$-Ter, wherein m is between 0 and 12 and Int and Ter are Internal and Terminal building blocks, wherein Int is selected from the consisting of

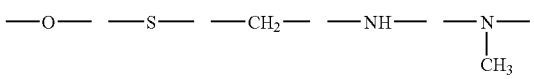

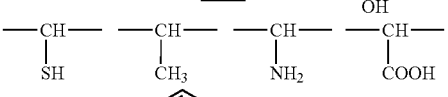

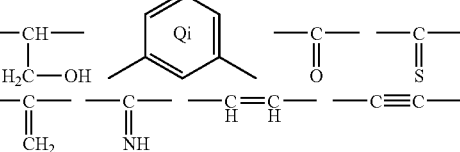

and Ter is selected from the consisting of

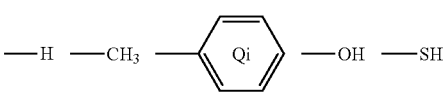

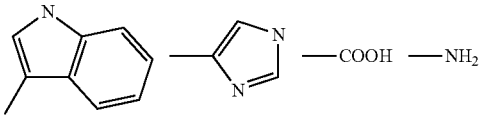

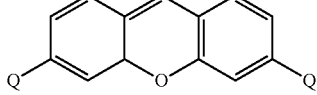

wherein an additional group Q, group Qi or groups Qi (Qi indicates that the group or several groups may be bound to any unsaturated moiety of the ring) are selected from the group consisting of —OH, —COOH, —N(CH$_3$)$_2$, —N(CH$_2$—CH$_3$)$_2$ or -Halogen elements In addition the sugar moiety of compounds of formula (I) can be selected from the group consisting of the following sugar moieties or sugar-like moieties:

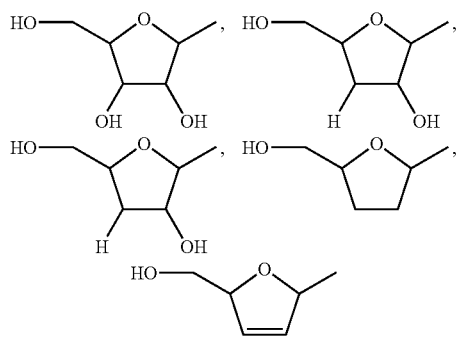

Compounds of formula (I), (Ia) and (II) can be labelled, particularly with $R_3$ or $R_4$ selected from

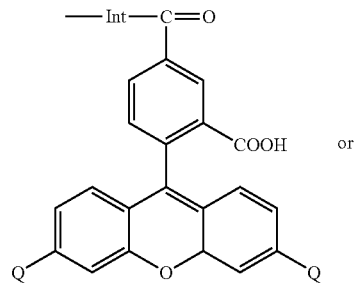

or

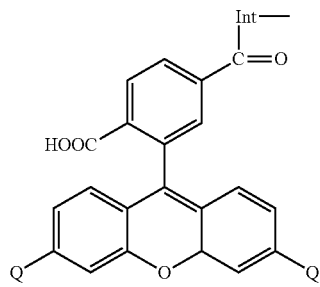

wherein Q is selected from —OH (FAM) or —N(CH$_3$)$_2$ (TAMRA).

According to some embodiments of the present invention the compounds of formula (I), (Ia) and (II) are the compounds described below:

SM4410

2',3'-EDA-6-Thio-GTP, ID: 05B-0

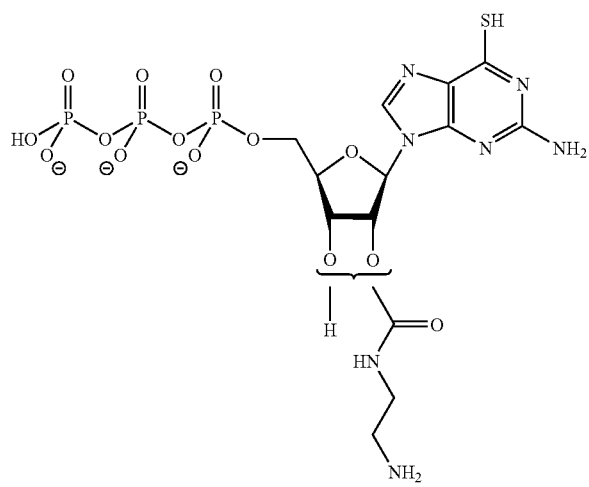

| m = 0 | Ter | n = 3 | 1 | 2 | 3 | | Ter | | |
|---|---|---|---|---|---|---|---|---|---|
| —R1 | —SH | —R5 | —PO$_3$— | —PO$_3$— | —PO$_3$— | | —OH | | |
| m = 6 | Int$_1$ | Int$_2$ | Int$_3$ | Int$_4$ | Int$_5$ | Int$_6$ | Ter | m = 0 Ter | m = 0 Ter |
| —R3 o —R4 | —O— | —C— ‖ O | —NH— | —CH$_2$— | —CH$_2$— | —NH— | —H | —R3 o —R4 | —OH —R2 —H |

FAM-2',3'-EDA-6-Thio-GTP
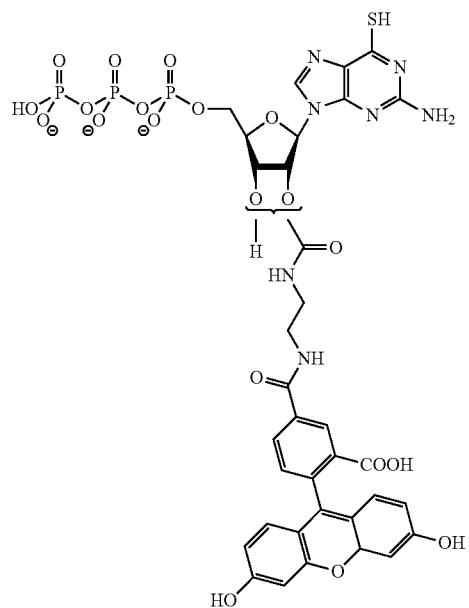
| m = 0 | Ter | n = 3 | 1 | 2 | 3 | Ter | m = 0 | Ter |
|---|---|---|---|---|---|---|---|---|
| —R1 | —SH | —R5 | —PO₃— | —PO₃— | —PO₃— | —OH | —R2 | —H |
| m = 8 | Int₁ | Int₂ | Int₃ | Int₄ | Int₅ | Int₆ | Int₇ | Int₈ | Ter |
| —R3 o —R4 | —O— | —C(=O)— | —NH— | —CH₂— | —CH₂— | —NH— | —C(=O)— | (dimethylbenzoic acid) | (xanthene-diol) |
| m = 0 | Ter |
|---|---|
| —R3 o R4 | —OH |

TAMRA-2',3'-EDA-6-Thio-GTP
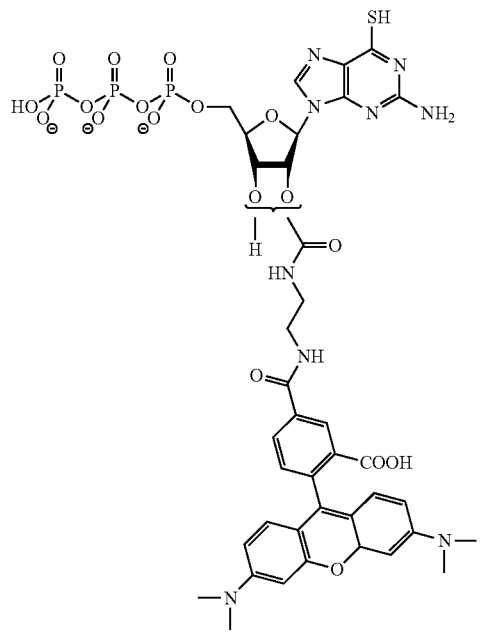
| m = 0 | Ter | | n = 3 | 1 | 2 | 3 | Ter | | m = 0 | Ter |
|---|---|---|---|---|---|---|---|---|---|---|
| —R1 | —SH | | —R5 | —PO$_3$— | —PO$_3$— | —PO$_3$— | —OH | | —R3 o R4 | —OH |
| m = 8 | Int$_1$ | Int$_2$ | Int$_3$ | Int$_4$ | Int$_5$ | Int$_6$ | Int$_7$ | Int$_8$ | Ter | |
| —R3 o —R4 | —O— | —C(=O)— | —NH— | —CH$_2$— | —CH$_2$— | —NH— | —C(=O)— | 5-methyl-2-COOH-phenyl | 9-methylxanthene-3,6-bis(N(CH$_3$)$_2$) | |
| | | | | | m = 0 | | Ter | | | |
| | | | | | —R2 | | —H | | | |

Aspartate-2,3'-EDA-6-Thio-GTP, ID: 05B-1
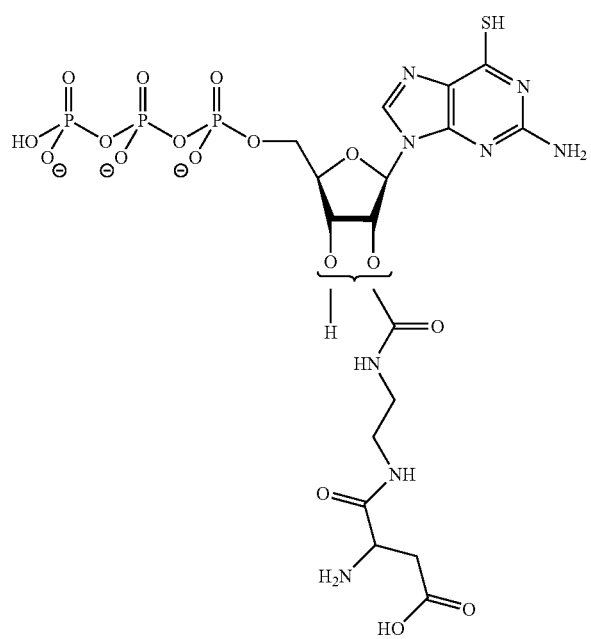
| m = 0 | Ter | | | | n = 3 | 1 | 2 | 3 | Ter | | | |
|---|---|---|---|---|---|---|---|---|---|---|---|---|
| —R1 | —SH | | | | —R5 | —PO$_3$— | —PO$_3$— | —PO$_3$— | —OH | | | |
| m = 9 | Int$_1$ | Int$_2$ | Int$_3$ | Int$_4$ | Int$_5$ | Int$_6$ | Int$_7$ | Int$_8$ | Int$_9$ | Ter | m = 0 Ter | m = 0 Ter |
| —R3 o —R4 | —O— | —C— ‖ O | —NH— | —CH$_2$— | —CH$_2$— | —NH— | —C— ‖ O | —CH— NH$_2$ | —CH$_2$— | —COOH | —R2 | —R3 o —R4 |

Glutamate-2',3'-EDA-6-Thio-GTP, ID: 05B-2
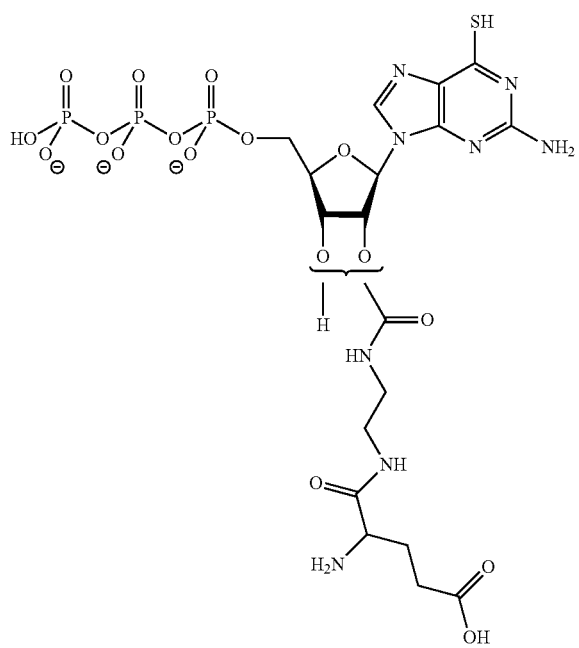
| m = 0 | Ter | | n = 3 | 1 | 2 | 3 | Ter |
|---|---|---|---|---|---|---|---|
| —R1 | —SH | | —R5 | —PO$_3$— | —PO$_3$— | —PO$_3$— | —OH |
| m = 10 | Int$_1$ | Int$_2$ | Int$_3$ | Int$_4$ | Int$_5$ | Int$_6$ | Int$_7$ | Int$_8$ | Int$_9$ | Int$_{10}$ | Ter |
| —R3 o —R4 | —O— | —C(=O)— | —NH— | —CH$_2$— | —CH$_2$— | —NH— | —C(=O)— | —CH(NH$_2$)— | —CH$_2$— | —CH$_2$— | —COOH |
| | | m = 0 | Ter | | | | m = 0 | Ter | | | |
| | | —R2 | —H | | | | —R3 o —R4 | —OH | | | |

Threonine-2',3'-EDA-6-Thio-GTP, ID: 05B-3
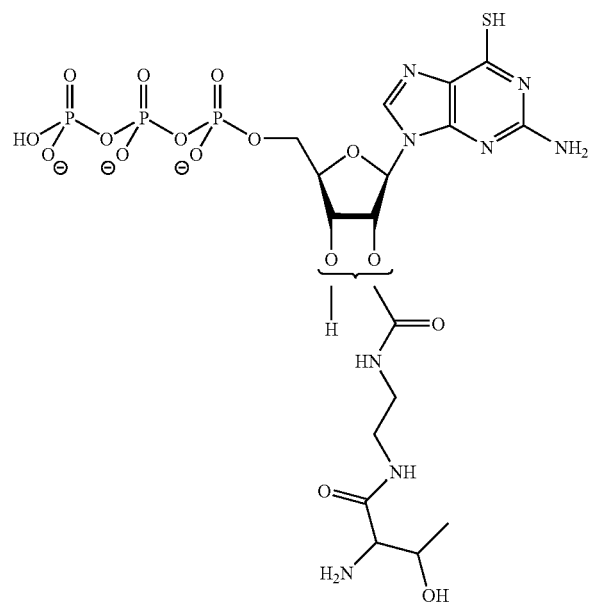
| m = 0 | Ter | | n = 3 | 1 | 2 | 3 | Ter |
|---|---|---|---|---|---|---|---|
| —R1 | —SH | | —R5 | —PO$_3$— | —PO$_3$— | —PO$_3$— | —OH |
| m = 9 | Int$_1$ | Int$_2$ | Int$_3$ | Int$_4$ | Int$_5$ | Int$_6$ | Int$_7$ | Int$_8$ | Int$_9$ | Ter |
| —R3 o —R4 | —O— | —C(=O)— | —NH— | —CH$_2$— | —CH$_2$— | —NH— | —C(=O)— | —CH(NH$_2$)— | —CH(OH)— | —CH$_3$ |
| | | m = 0 | Ter | | | m = 0 | Ter | | | |
| | | —R2 | —H | | | —R3 o —R4 | —OH | | | |

Serine-2',3'-EDA-6-Thio-GTP
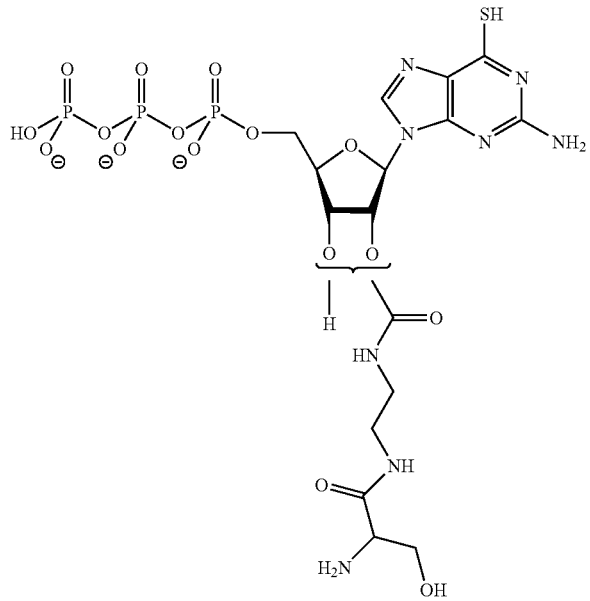
| m = 0 | Ter | n = 3 | 1 | 2 | 3 | Ter |
|---|---|---|---|---|---|---|
| —R1 | —SH | —R5 | —PO$_3$— | —PO$_3$— | —PO$_3$— | —OH |
| m = 9 | Int$_1$ | Int$_2$ | Int$_3$ | Int$_4$ | Int$_5$ | Int$_6$ | Int$_7$ | Int$_8$ | Int$_9$ | Ter |
| —R3 o —R4 | —O— | —C(=O)— | —NH— | —CH$_2$— | —CH$_2$— | —NH— | —C(=O)— | —CH(NH$_2$)— | —CH$_2$— | —OH |
| | | m = 0 | Ter | | | m = 0 | Ter | | | |
| | —R3 o —R4 | —OH | | | | —R2 | —H | | | |
2',3',5',O-Triacetyl-N-2-(Acetyl-6''-aminohexyl)-guanosine
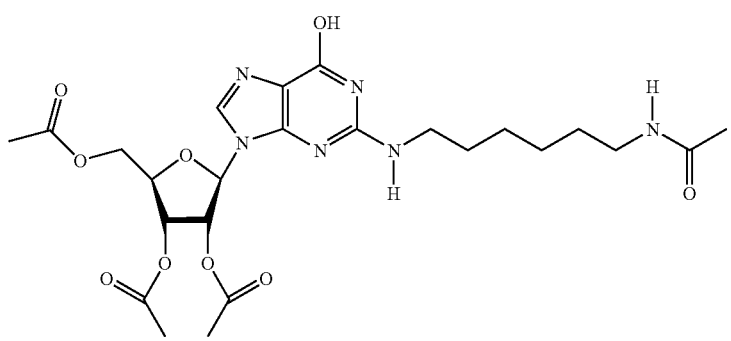
| m = 0 | Ter | m = 2 | Int$_1$ | Int$_2$ | Ter | m = 2 | Int$_1$ | Int$_2$ | Ter |
|---|---|---|---|---|---|---|---|---|---|
| —R1 | —OH | —R5 | —O— | —C(=O)— | —CH$_3$ | —R3 e —R4 | —O— | —C(=O)— | —CH$_3$ |

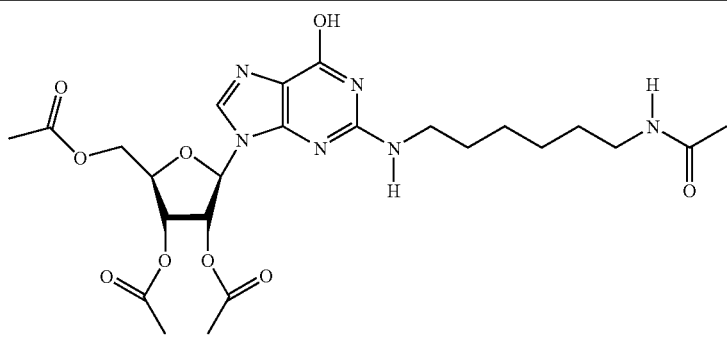
| m = 8 | Int₁ | Int₂ | Int₃ | Int₄ | Int₅ | Int₆ | Int₇ | Int₈ | Ter |
|---|---|---|---|---|---|---|---|---|---|
| —R2 | —CH₂— | —CH₂— | —CH₂— | —CH₂— | —CH₂— | —CH₂— | —NH— | —C(=O)— | —CH₃ |
2',3',5'-Triacetyl-N-2-(6''-thioacetamide-hexyl)-6-Thioguanosine (V4) [TWI 107/7]
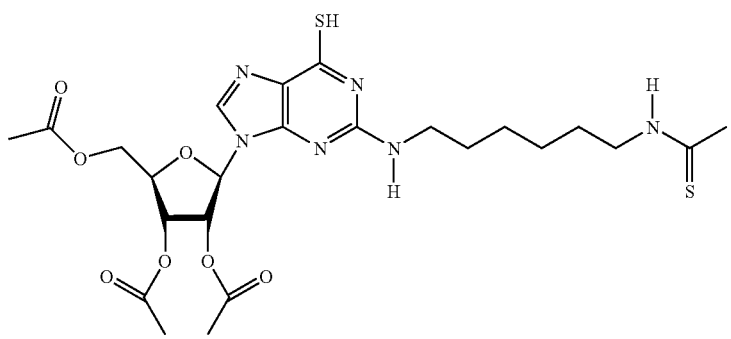
| m = 0 | Ter | m = 2 | Int₁ | Int₂ | Ter | m = 2 | Int₁ | Int₂ | Ter |
|---|---|---|---|---|---|---|---|---|---|
| —R1 | —SH | —R5 | —O— | —C(=O)— | —CH₃ | —R3 e —R4 | —O— | —C(=O)— | —CH₃ |
| m = 8 | Int₁ | Int₂ | Int₃ | Int₄ | Int₅ | Int₆ | Int₇ | Int₈ | Ter |
|---|---|---|---|---|---|---|---|---|---|
| —R2 | —CH₂— | —CH₂— | —CH₂— | —CH₂— | —CH₂— | —CH₂— | —NH— | —C(=S)— | —CH₃ |

N-2-(6"-thioacetamide-hexyl)-6-Thioguanosine
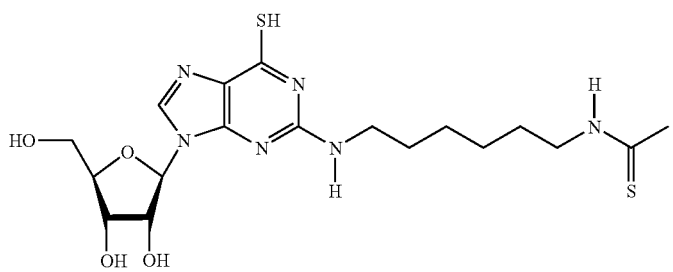
| m = 0 | Ter | | m = 0 | Ter | | m = 0 | | Ter |
|---|---|---|---|---|---|---|---|---|
| —R1 | —SH | | —R5 | —OH | | —R3 e R4 | | —OH |
| m = 8 | Int$_1$ | Int$_2$ | Int$_3$ | Int$_4$ | Int$_5$ | Int$_6$ | Int$_7$ | Int$_8$ | Ter |
| —R2 | —CH$_2$— | —CH$_2$— | —CH$_2$— | —CH$_2$— | —CH$_2$— | —CH$_2$— | —NH— | —C(=S)— | —CH$_3$ |
N-2-(6"-Aminohexyl)-6-Thioguanosine, ID: 05A-0
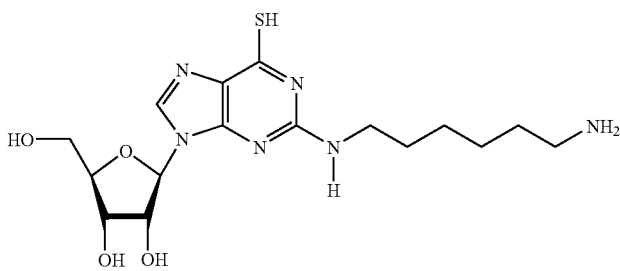
| m = 0 | Ter | m = 0 | Ter | m = 0 | Ter |
|---|---|---|---|---|---|
| —R1 | —SH | —R3 e —R4 | —OH | —R5 | —OH |
| m = 6 | Int$_1$ | Int$_2$ | Int$_3$ | Int$_4$ | Int$_5$ | Int$_6$ | Ter |
| —R2 | —CH$_2$— | —CH$_2$— | —CH$_2$— | —CH$_2$— | —CH$_2$— | —CH$_2$— | —NH$_2$ |

N-2-(6"-guanidino-hexyl)-6-Thioguanosine, ID: 05A-1
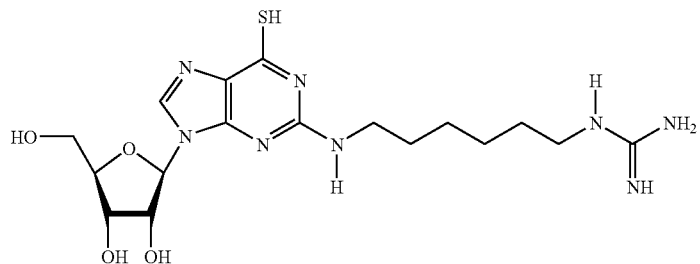
| m = 0 | Ter | | | n = 0 | Ter | | m = 0 | Ter |
|---|---|---|---|---|---|---|---|---|
| —R1 | —SH | | | —R5 | —OH | | —R3 e —R4 | —OH |
| m = 8 | Int₁ | Int₂ | Int₃ | Int₄ | Int₅ | Int₆ | Int₇ | Int₈ | Ter |
| —R2 | —CH₂— | —CH₂— | —CH₂— | —CH₂— | —CH₂— | —CH₂— | —NH— | —C— ‖ NH | —NH₂ |
N-2-(6"-Aminohexyl)-6-Thio-GMP    35
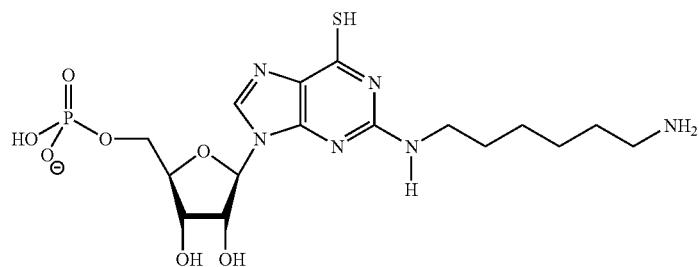
| m = 0 | Ter | n = 1 | 1 | Ter | m = 0 | Ter |
|---|---|---|---|---|---|---|
| —R1 | —SH | —R5 | —PO₃— | —OH | —R3 e —R4 | —OH |
| m = 6 | Int₁ | Int₂ | Int₃ | Int₄ | Int₅ | Int₆ | Ter |
| —R2 | —CH₂— | —CH₂— | —CH₂— | —CH₂— | —CH₂— | —CH₂— | —NH₂ |

N-2-(6"-guanidino-hexyl)-6-Thio-GMP, ID: 05A-2

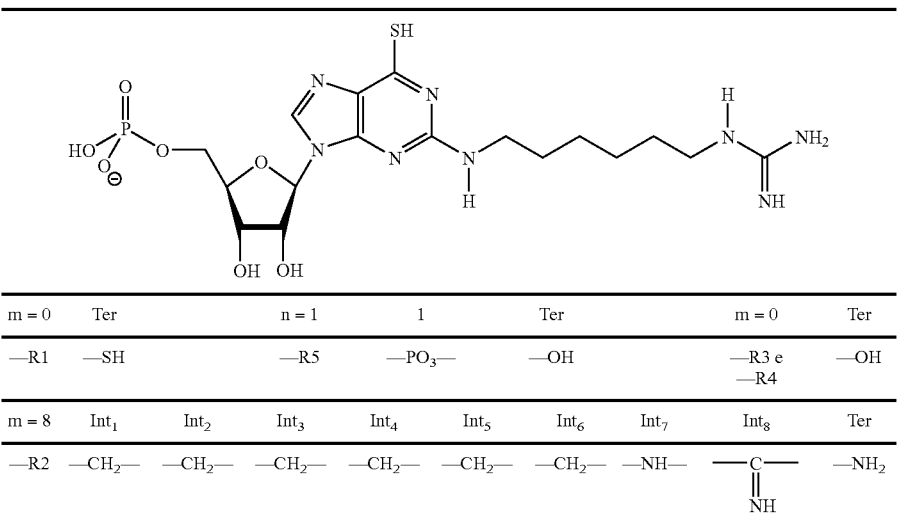

| m = 0 | Ter | n = 1 | 1 | Ter | m = 0 | Ter |
|---|---|---|---|---|---|---|
| —R1 | —SH | —R5 | —PO$_3$— | —OH | —R3 e —R4 | —OH |

| m = 8 | Int$_1$ | Int$_2$ | Int$_3$ | Int$_4$ | Int$_5$ | Int$_6$ | Int$_7$ | Int$_8$ | Ter |
|---|---|---|---|---|---|---|---|---|---|
| —R2 | —CH$_2$— | —CH$_2$— | —CH$_2$— | —CH$_2$— | —CH$_2$— | —CH$_2$— | —NH— | $\overset{\displaystyle \|}{\underset{\displaystyle NH}{-C-}}$ | —NH$_2$ |

N-2-(6"-Aminohexyl)-6-Thio-GTP

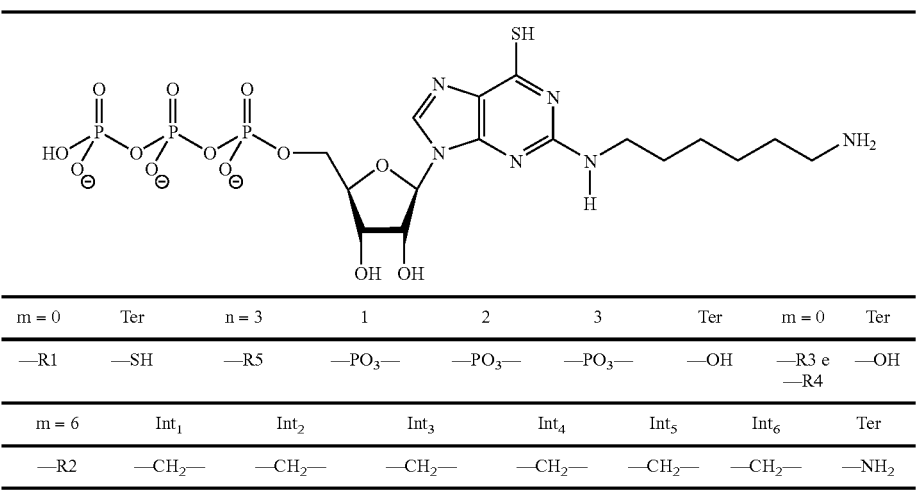

| m = 0 | Ter | n = 3 | 1 | 2 | 3 | Ter | m = 0 | Ter |
|---|---|---|---|---|---|---|---|---|
| —R1 | —SH | —R5 | —PO$_3$— | —PO$_3$— | —PO$_3$— | —OH | —R3 e —R4 | —OH |

| m = 6 | Int$_1$ | Int$_2$ | Int$_3$ | Int$_4$ | Int$_5$ | Int$_6$ | Ter |
|---|---|---|---|---|---|---|---|
| —R2 | —CH$_2$— | —CH$_2$— | —CH$_2$— | —CH$_2$— | —CH$_2$— | —CH$_2$— | —NH$_2$ |

N-2-(6"-guanidino-hexyl)-6-Thio-GTP, ID: 05A-3

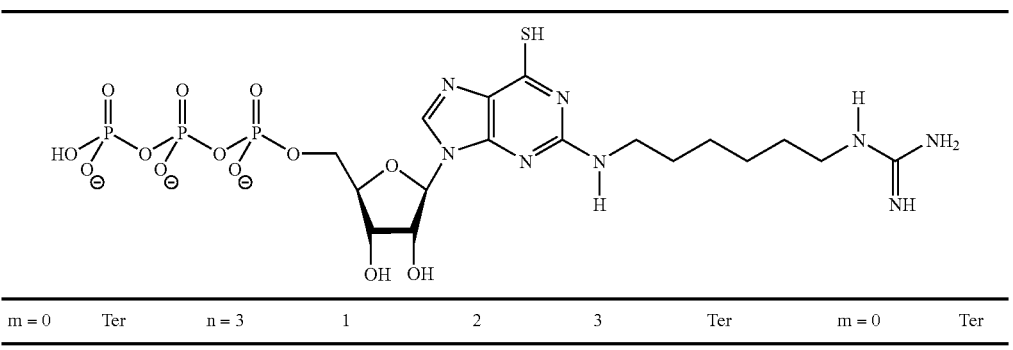

| m = 0 | Ter | n = 3 | 1 | 2 | 3 | Ter | m = 0 | Ter |
|---|---|---|---|---|---|---|---|---|

-continued
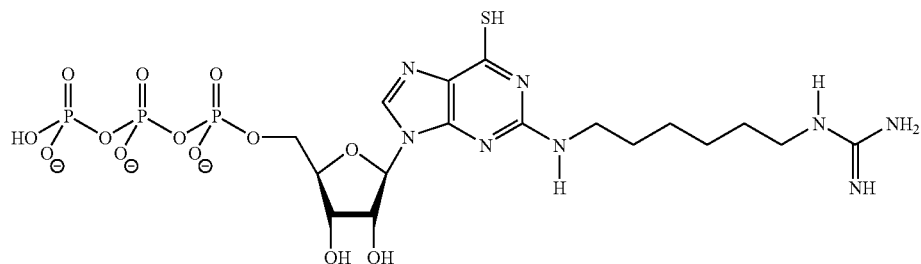
| —R1 | —SH | —R5 | —PO₃— | —PO₃— | —PO₃— | —OH | —R3 e —R4 | —OH |
|---|---|---|---|---|---|---|---|---|
| m = 8 | Int₁ | Int₂ | Int₃ | Int₄ | Int₅ | Int₆ | Int₇ | Int₈ | Ter |
| —R2 | —CH₂— | —CH₂— | —CH₂— | —CH₂— | —CH₂— | —CH₂— | —NH— | —C— ‖ NH | —NH₂ |
N-2-(6"-Aspartate-hexyl)-6-Thioguanosine
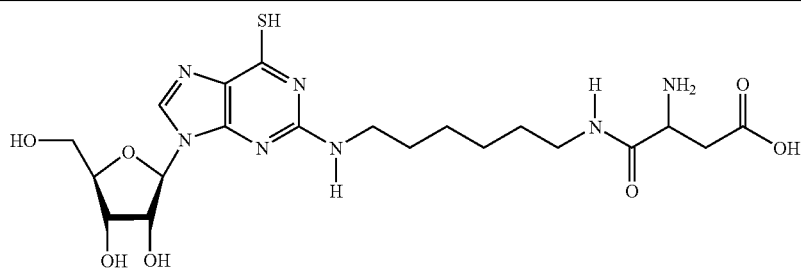
| m = 0 | Ter | | | n = 0 | Ter | | | m = 0 | Ter |
|---|---|---|---|---|---|---|---|---|---|
| —R1 | —SH | | | —R5 | —OH | | | —R3 e —R4 | —OH |
| m = 10 | Int₁ | Int₂ | Int₃ | Int₄ | Int₅ | Int₆ | Int₇ | Int₈ | Int₉ | Int₁₀ | Ter |
| —R2 | —CH₂— | —CH₂— | —CH₂— | —CH₂— | —CH₂— | —CH₂— | —NH— | —C— ‖ O | —CH— | NH₂ | —CH₂— | —COOH |
N-2-(6"-Glutamate-hexyl)-6-Thioguanosine
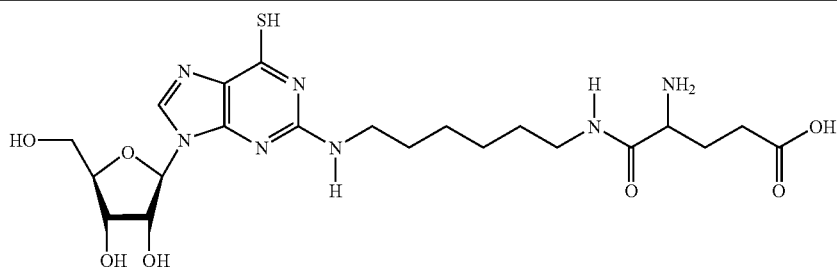
| m = 0 | Ter | n = 0 | Ter | m = 0 | Ter |
|---|---|---|---|---|---|
| —R1 | —SH | —R5 | —OH | —R3 e —R4 | —OH |

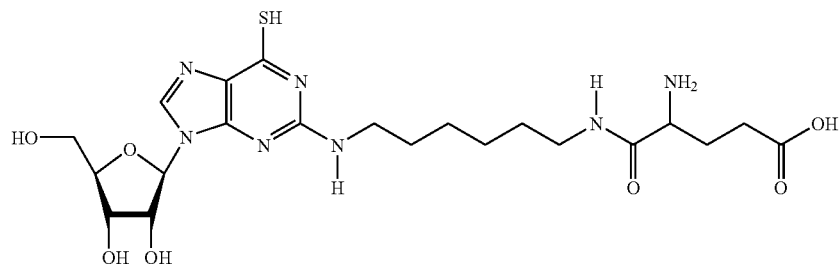

| m = 1 | Int$_1$ | Int$_2$ | Int$_3$ | Int$_4$ | Int$_5$ | Int$_6$ | Int$_7$ | Int$_8$ | Int$_9$ | Int$_{10}$ | Int$_{11}$ | Ter |
|---|---|---|---|---|---|---|---|---|---|---|---|---|
| —R2 | —CH$_2$— | —CH$_2$— | —CH$_2$— | —CH$_2$— | —CH$_2$— | —CH$_2$— | —NH— | —C(=O)— | —CH(NH$_2$)— | —CH$_2$— | —CH$_2$— | —COOH |

N-2-(6″-Threonine-hexyl)-6-Thioguanosine

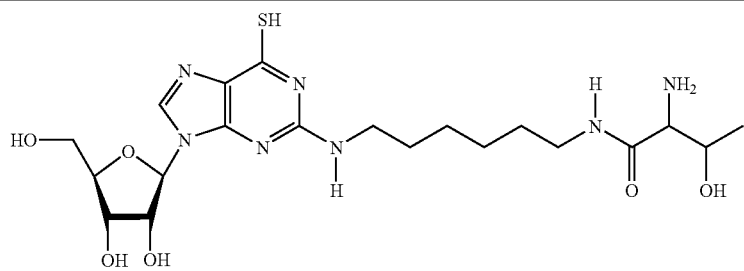

| m = 0 | Ter | | n = 0 | Ter | | m = 0 | Ter |
|---|---|---|---|---|---|---|---|
| —R1 | —SH | | —R5 | —OH | | —R3 e —R4 | —OH |

| m = 10 | Int$_1$ | Int$_2$ | Int$_3$ | Int$_4$ | Int$_5$ | Int$_6$ | Int$_7$ | Int$_8$ | Int$_9$ | Int$_{10}$ | Ter |
|---|---|---|---|---|---|---|---|---|---|---|---|
| —R2 | —CH$_2$— | —CH$_2$— | —CH$_2$— | —CH$_2$— | —CH$_2$— | —CH$_2$— | —NH— | —C(=O)— | —CH(NH$_2$)— | —CH(OH)— | —CH$_3$ |

N-2-(6″-Serine-hexyl)-6-Thioguanosine      45

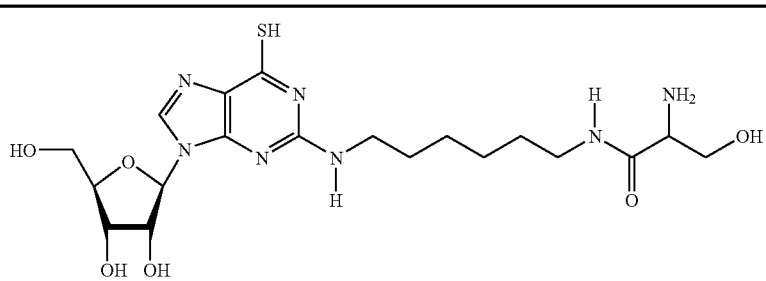

| m = 0 | Ter | | n = 0 | Ter | | m = 0 | Ter |
|---|---|---|---|---|---|---|---|
| —R1 | —SH | | —R5 | —OH | | —R3 e —R4 | —OH |

| m = 10 | Int$_1$ | Int$_2$ | Int$_3$ | Int$_4$ | Int$_5$ | Int$_6$ | Int$_7$ | Int$_8$ | Int$_9$ | Int$_{10}$ | Ter |

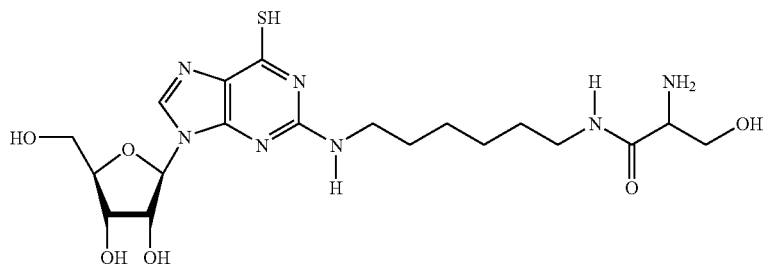
| —R2 | —CH₂— | —CH₂— | —CH₂— | —CH₂— | —CH₂— | —CH₂— | —NH— | —C— ‖ O | —CH— NH₂ | —CH₂— | —OH |
N-2-(6"-Aminobutyl)-6-Thio-Guanosine, ID: 05C-0
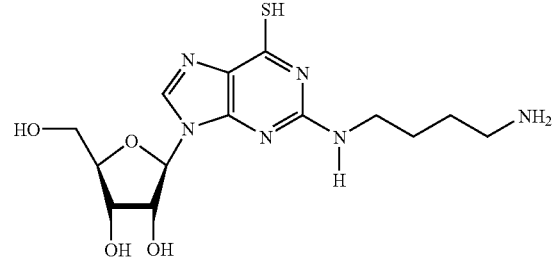
| m = 0 | Ter | n = 0 | Ter | m = 0 | Ter |
|---|---|---|---|---|---|
| —R1 | —SH | —R5 | —OH | —R3 e —R4 | —OH |
-continued
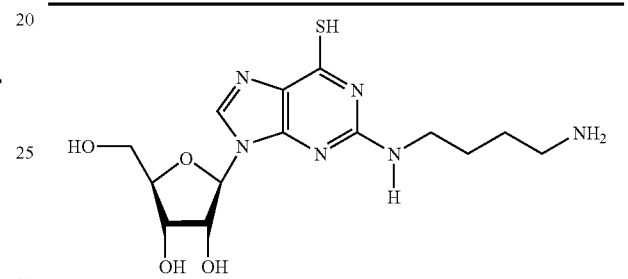
| m = 4 | Int₁ | Int₂ | Int₃ | Int₄ | Ter |
|---|---|---|---|---|---|
| —R2 | —CH₂— | —CH₂— | —CH₂— | —CH₂— | —NH₂ |
2-N-2-(6"-guanidino-butyl)-6-Thioguanosine, ID: 05C-1
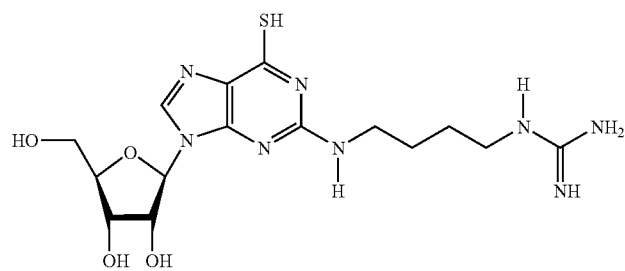
| m = 0 | Ter | n = 0 | Ter | m = 0 | Ter |
|---|---|---|---|---|---|
| —R1 | —SH | —R5 | —OH | —R3 e —R4 | —OH |
| m = 6 | Int₁ | Int₂ | Int₃ | Int₄ | Int₅ | Int₆ | Ter |
|---|---|---|---|---|---|---|---|
| —R2 | —CH₂— | —CH₂— | —CH₂— | —CH₂— | —NH— | —C— ‖ NH | —NH₂ |

2-N-2-(6"-guanidino-butyl)-6-Thio-GMP, ID: 05C-2
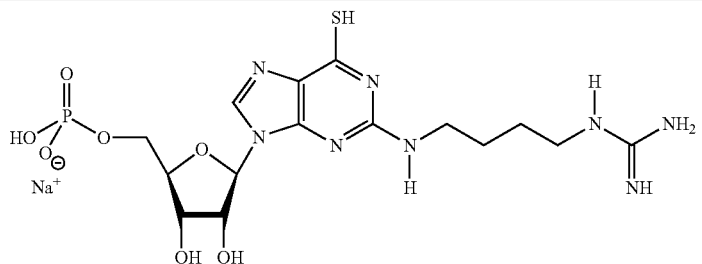
| m = 0 | Ter | n = 1 | 1 | Ter | m = 0 | Ter |
|---|---|---|---|---|---|---|
| —R1 | —SH | —R5 | —PO$_3$— | —OH | —R3 e —R4 | —OH |
| m = 6 | Int$_1$ | Int$_2$ | Int$_3$ | Int$_4$ | Int$_5$ | Int$_6$ | Ter |
| —R2 | —CH$_2$— | —CH$_2$— | —CH$_2$— | —CH$_2$— | —NH— | —C(=NH)— | —NH$_2$ |
2-N-2-(6"-guanidino-butyl)-6-Thio-GTP, ID: 05C-3
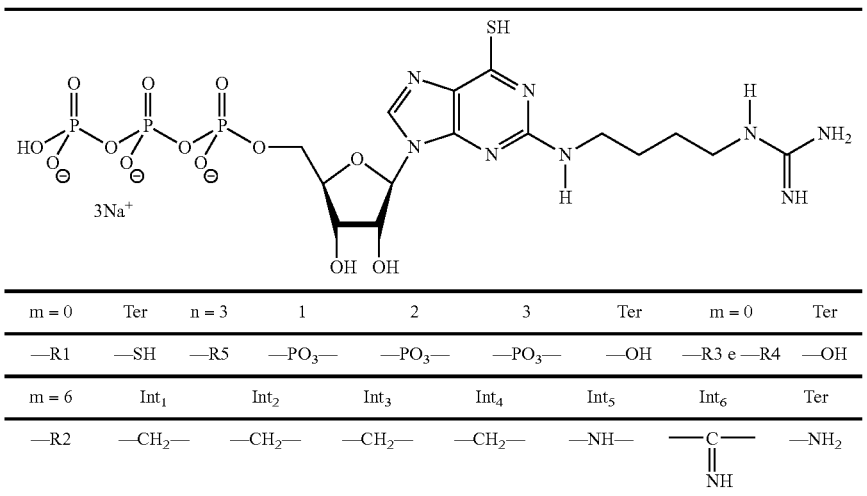
| m = 0 | Ter | n = 3 | 1 | 2 | 3 | Ter | m = 0 | Ter |
|---|---|---|---|---|---|---|---|---|
| —R1 | —SH | —R5 | —PO$_3$— | —PO$_3$— | —PO$_3$— | —OH | —R3 e —R4 | —OH |
| m = 6 | Int$_1$ | Int$_2$ | Int$_3$ | Int$_4$ | Int$_5$ | Int$_6$ | Ter |
| —R2 | —CH$_2$— | —CH$_2$— | —CH$_2$— | —CH$_2$— | —NH— | —C(=NH)— | —NH$_2$ |
N-2-(6"-Aspartate-butyl)-6-Thioguanosine
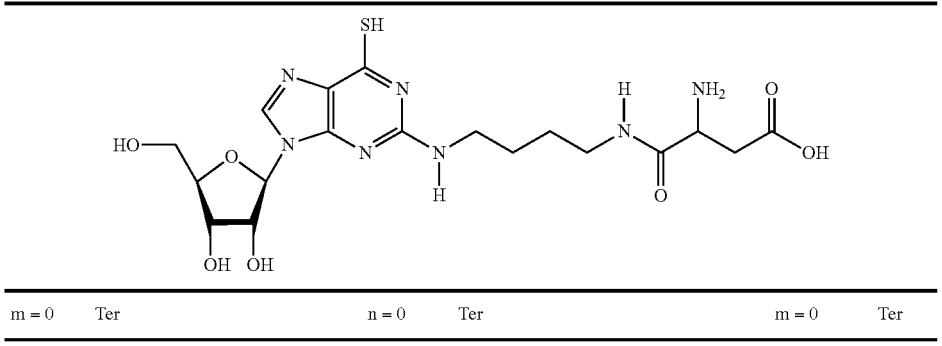
| m = 0 | Ter | n = 0 | Ter | m = 0 | Ter |
|---|---|---|---|---|---|

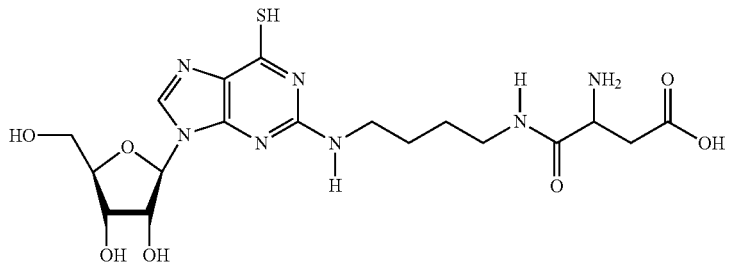
| —R1 | —SH | | | —R5 | —OH | | | —R3 e —R4 | —OH |
|---|---|---|---|---|---|---|---|---|---|
| m = 8 | Int$_1$ | Int$_2$ | Int$_3$ | Int$_4$ | Int$_5$ | Int$_6$ | Int$_7$ | Int$_8$ | Ter |
| —R2 | —CH$_2$— | —CH$_2$— | —CH$_2$— | —CH$_2$— | —NH— | —C(=O)— | —CH(NH$_2$)— | —CH$_2$— | —COOH |
N-2-(6"-Glutamate-butyl)-6-Thioguanosine
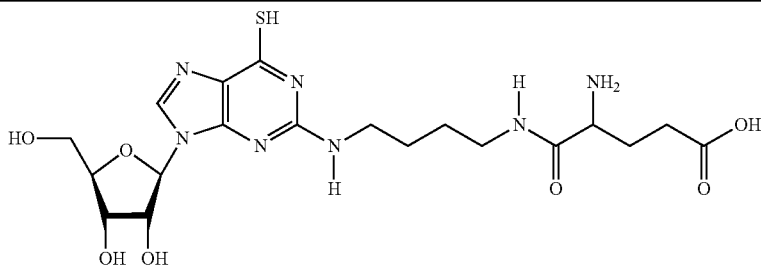
| m = 0 | Ter | | | n = 0 | Ter | | | m = 0 | Ter | |
|---|---|---|---|---|---|---|---|---|---|---|
| —R1 | —SH | | | —R5 | —OH | | | —R3 e —R4 | —OH | |
| m = 9 | Int$_1$ | Int$_2$ | Int$_3$ | Int$_4$ | Int$_5$ | Int$_6$ | Int$_7$ | Int$_8$ | Int$_9$ | Ter |
| —R2 | —CH$_2$— | —CH$_2$— | —CH$_2$— | —CH$_2$— | —NH— | —C(=O)— | —CH(NH$_2$)— | —CH$_2$— | —CH$_2$— | —COOH |
N-2-(6"-Threonine-butyl)-6-Thioguanosine
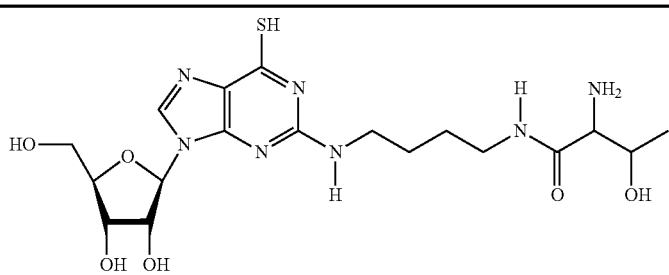
| m = 0 | Ter | n = 0 | Ter | m = 0 | Ter |
|---|---|---|---|---|---|
| —R1 | —SH | —R5 | —OH | —R3 e —R4 | —OH |

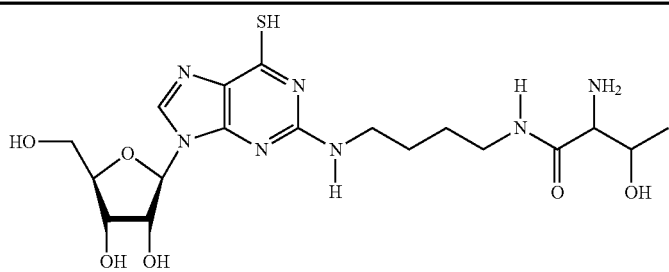

| m = 8 | Int$_1$ | Int$_2$ | Int$_3$ | Int$_4$ | Int$_5$ | Int$_6$ | Int$_7$ | Int$_8$ | Ter |
|---|---|---|---|---|---|---|---|---|---|
| —R2 | —CH$_2$— | —CH$_2$— | —CH$_2$— | —CH$_2$— | —NH— | —C(=O)— | —CH(NH$_2$)— | —CH(OH)— | —CH$_3$ |

N-2-(6''-Serine-butyl)-6-Thioguanosine

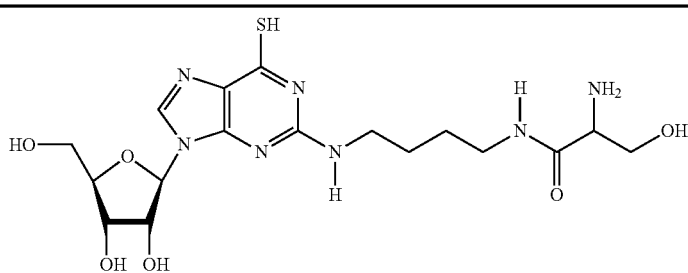

| m = 0 | Ter | | | n = 0 | Ter | | | m = 0 | Ter |
|---|---|---|---|---|---|---|---|---|---|
| —R1 | —SH | | | —R5 | —OH | | | —R3 e —R4 | —OH |

| m = 8 | Int$_1$ | Int$_2$ | Int$_3$ | Int$_4$ | Int$_5$ | Int$_6$ | Int$_7$ | Int$_8$ | Ter |
|---|---|---|---|---|---|---|---|---|---|
| —R2 | —CH$_2$— | —CH$_2$— | —CH$_2$— | —CH$_2$— | —NH— | —C(=O)— | —CH(NH$_2$)— | —CH$_2$— | —OH |

N-2-(6''-Aminopropyl)-6-Thioguanosine

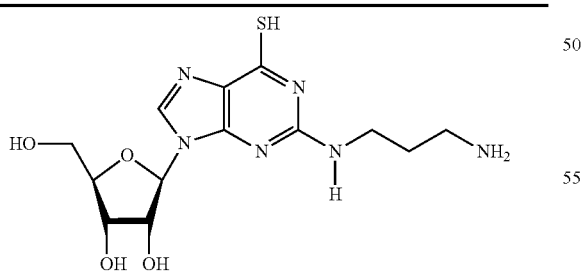

| m = 0 | Ter | n = 0 | Ter | m = 0 | Ter |
|---|---|---|---|---|---|
| —R1 | —SH | —R5 | —OH | —R3 e —R4 | —OH |

| m = 0 | Int$_1$ | Int$_2$ | Int$_3$ | Ter |
|---|---|---|---|---|
| —R2 | —CH$_2$— | —CH$_2$— | —CH$_2$— | —NH$_2$ |

N-2-(6"-guanidino-propyl)-6-Thioguanosine
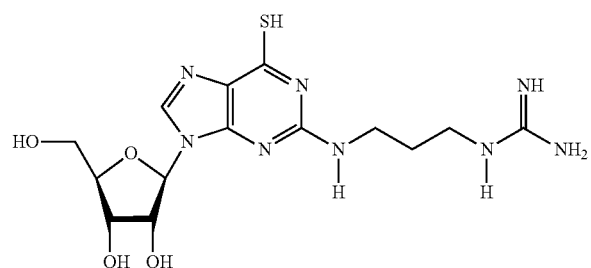
| m = 0 | Ter | n = 0 | Ter | m = 0 | Ter |
|---|---|---|---|---|---|
| —R1 | —SH | —R5 | —OH | —R3 e —R4 | —OH |
| m = 5 | Int$_1$ | Int$_2$ | Int$_3$ | Int$_4$ | Int$_5$ | Ter |
| —R2 | —CH$_2$— | —CH$_2$— | —CH$_2$— | —NH— | —C(=NH)— | —NH$_2$ |
N-2-(6"-Aspartate-propyl)-6-Thioguanosine
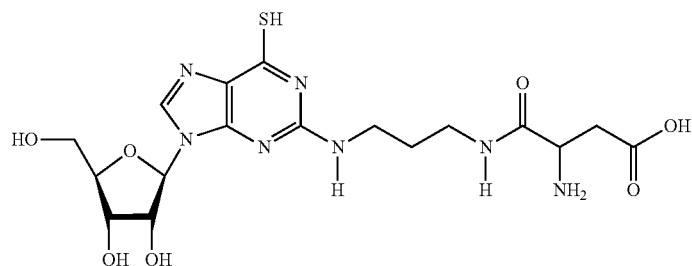
| m = 0 | Ter | n = 0 | Ter | m = 0 | Ter |
|---|---|---|---|---|---|
| —R1 | —SH | —R5 | —OH | —R3 e —R4 | —OH |
| m = 7 | Int$_1$ | Int$_2$ | Int$_3$ | Int$_4$ | Int$_5$ | Int$_6$ | Int$_7$ | Ter |
| —R2 | —CH$_2$— | —CH$_2$— | —CH$_2$— | —NH— | —C(=O)— | —CH(NH$_2$)— | —CH$_2$— | —COOH |

N-2-(6''-Glutamate-propyl)-6-Thioguanosine

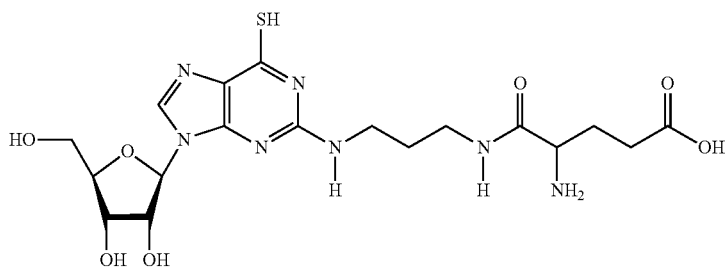

| m = 0 | Ter | | | n = 0 | Ter | | | m = 0 | Ter |
|---|---|---|---|---|---|---|---|---|---|
| —R1 | —SH | | | —R5 | —OH | | | —R3 e —R4 | —OH |
| m = 8 | Int$_1$ | Int$_2$ | Int$_3$ | Int$_4$ | Int$_5$ | Int$_6$ | Int$_7$ | Int$_8$ | Ter |
| —R2 | —CH$_2$— | —CH$_2$— | —CH$_2$— | —NH— | —C— $\parallel$ O | —CH— $\mid$ NH$_2$ | —CH$_2$— | —CH$_2$— | —COOH |

N-2-(6''-Threonine-propyl)-6-Thioguanosine

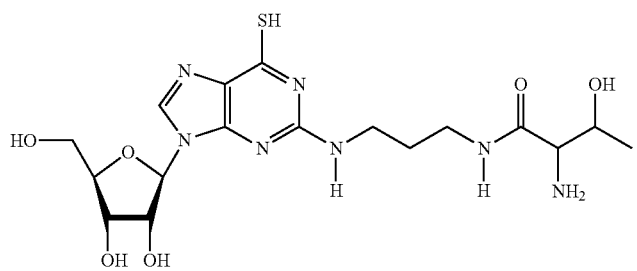

| m = 0 | Ter | | | n = 0 | Ter | | m = 0 | Ter |
|---|---|---|---|---|---|---|---|---|
| —R1 | —SH | | | —R5 | —OH | | —R3 e —R4 | —OH |
| m = 7 | Int$_1$ | Int$_2$ | Int$_3$ | Int$_4$ | Int$_5$ | Int$_6$ | Int$_7$ | Ter |
| —R2 | —CH$_2$— | —CH$_2$— | —CH$_2$— | —NH— | —C— $\parallel$ O | —CH— $\mid$ NH$_2$ | —CH— $\mid$ OH | —CH$_3$ |

N-2-(6"-Serine-propyl)-6-Thioguanosine

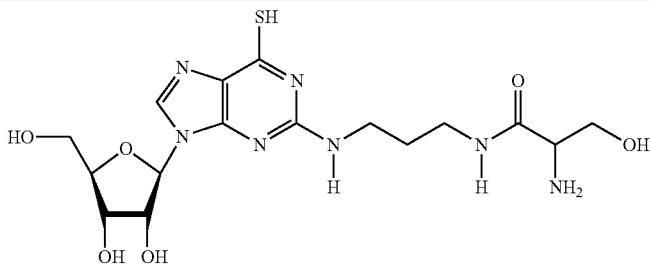

| m = 0 | Ter | | | n = 0 | Ter | | m = 0 | Ter |
|---|---|---|---|---|---|---|---|---|
| —R1 | —SH | | | —R5 | —OH | | —R3 e —R4 | —OH |

| m = 7 | Int₁ | Int₂ | Int₃ | Int₄ | Int₅ | Int₆ | Int₇ | Ter |
|---|---|---|---|---|---|---|---|---|
| —R2 | —CH₂— | —CH₂— | —CH₂— | —NH— | —C(=O)— | —CH(NH₂)— | —CH₂— | —OH |

N-2-(6"-Amino-2-butene)-6-Thioguanosine

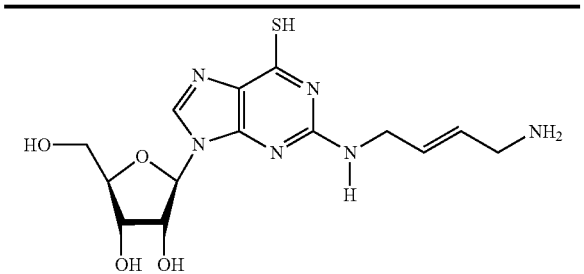

| m = 0 | Ter | n = 0 | Ter | m = 0 | Ter |
|---|---|---|---|---|---|
| —R1 | —SH | —R5 | —OH | —R3 e —R4 | —OH |

-continued

[structure: N-2-(6"-Amino-2-butene)-6-Thioguanosine variant with m=3]

| m = 3 | Int₁ | Int₂ | Int₃ | Ter |
|---|---|---|---|---|
| —R2 | —CH₂— | —CH=CH— | —CH₂— | —NH₂ |

N-2-(6"-guanidino-2-butene)-6-Thioguanosine

[structure]

| m = 0 | Ter | n = 0 | Ter | m = 0 | Ter |
|---|---|---|---|---|---|
| —R1 | —SH | —R5 | —OH | —R3 e —R4 | —OH |

| m = 5 | Int₁ | Int₂ | Int₃ | Int₄ | Int₅ | Ter |
|---|---|---|---|---|---|---|
| —R2 | —CH₂— | —CH=CH— | —CH₂— | —NH— | —C(=NH)— | —NH₂ |

N-2-(6''-Aspartate-2-butene)-6-Thioguanosine
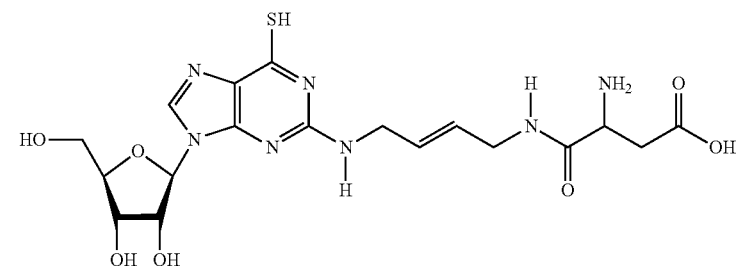
| m = 0 | Ter | | n = 0 | Ter | | m = 0 | Ter |
|---|---|---|---|---|---|---|---|
| —R1 | —SH | | —R5 | —OH | | —R3 e —R4 | —OH |
| m = 7 | $Int_1$ | $Int_2$ | $Int_3$ | $Int_4$ | $Int_5$ | $Int_6$ | $Int_7$ | Ter |
| —R2 | —$CH_2$— | —CH=CH— | —$CH_2$— | —NH— | —C(=O)— | —CH(NH$_2$)— | —$CH_2$— | —COOH |
N-2-(6''-Glutamate-2-butene)-6-Thioguanosine
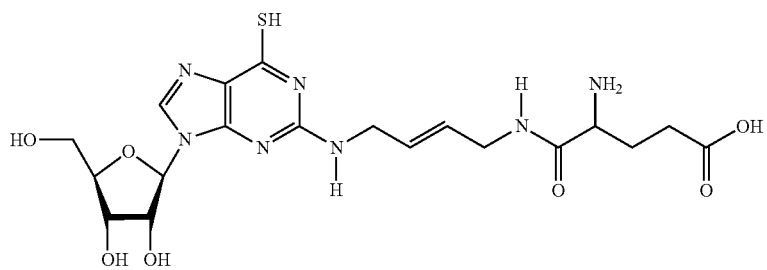
| m = 0 | Ter | | n = 0 | Ter | | m = 0 | Ter |
|---|---|---|---|---|---|---|---|
| —R1 | —SH | | —R5 | —OH | | —R3 e —R4 | —OH |
| m = 8 | $Int_1$ | $Int_2$ | $Int_3$ | $Int_4$ | $Int_5$ | $Int_6$ | $Int_7$ | $Int_8$ | Ter |
| —R2 | —$CH_2$— | —CH=CH— | —$CH_2$— | —NH— | —C(=O)— | —CH(NH$_2$)— | —$CH_2$— | —$CH_2$— | —COOH |

N-2-(6"-Threonine-2-butene)-6-Thioguanosine
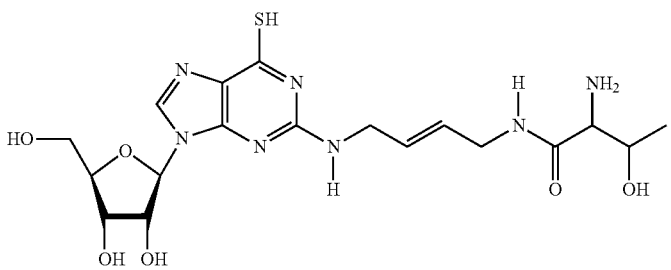
| m = 0 | Ter | | | n = 0 | Ter | | | m = 0 | Ter |
|---|---|---|---|---|---|---|---|---|---|
| —R1 | —SH | | | —R5 | —OH | | | —R3 e —R4 | —OH |
| m = 7 | Int$_1$ | Int$_2$ | Int$_3$ | Int$_4$ | Int$_5$ | Int$_6$ | Int$_7$ | Ter | |
| —R2 | —CH$_2$— | —C=C— H  H | —CH$_2$— | —NH— | —C— ‖ O | —CH— │ NH$_2$ | —CH— │ OH | —CH$_3$ | |
N-2-(6"-Serine-2-butene)-6-Thioguanosine
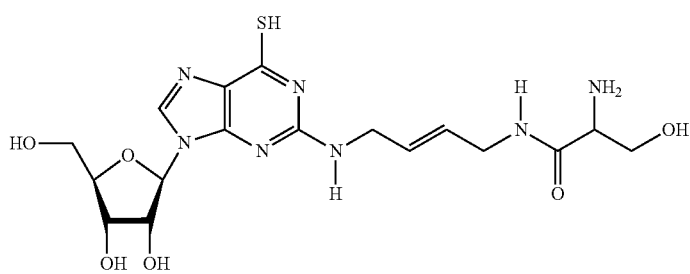
| m = 0 | Ter | | | n = 0 | Ter | | | m = 0 | Ter |
|---|---|---|---|---|---|---|---|---|---|
| —R1 | —SH | | | —R5 | —OH | | | —R3 e —R4 | —OH |
| m = 7 | Int$_1$ | Int$_2$ | Int$_3$ | Int$_4$ | Int$_5$ | Int$_6$ | Int$_7$ | Ter | |
| —R2 | —CH$_2$— | —C=C— H  H | —CH$_2$— | —NH— | —C— ‖ O | —CH— │ NH$_2$ | —CH$_2$— | —OH | |

57

N-2-(6"-Amino-2-butyne)-6-Thioguanosine

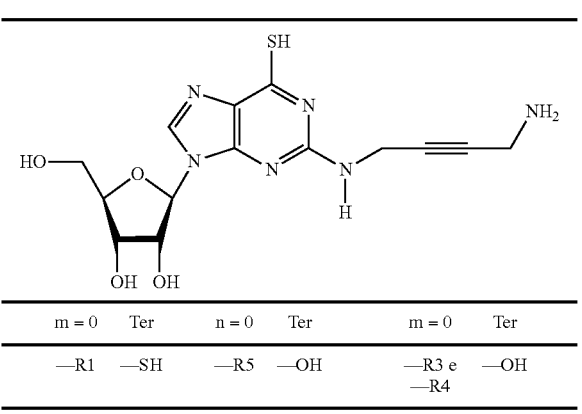

| m = 0 | Ter | n = 0 | Ter | m = 0 | Ter |
|---|---|---|---|---|---|
| —R1 | —SH | —R5 | —OH | —R3 e —R4 | —OH |

58

-continued

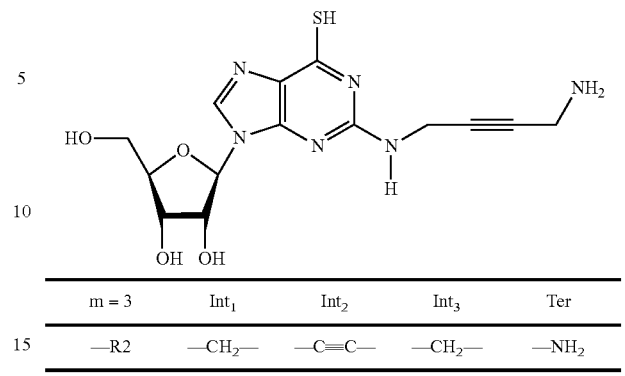

| m = 3 | $Int_1$ | $Int_2$ | $Int_3$ | Ter |
|---|---|---|---|---|
| —R2 | —$CH_2$— | —C≡C— | —$CH_2$— | —$NH_2$ |

N-2-(6"-guanidino-2-butyne)-6-Thioguanosine

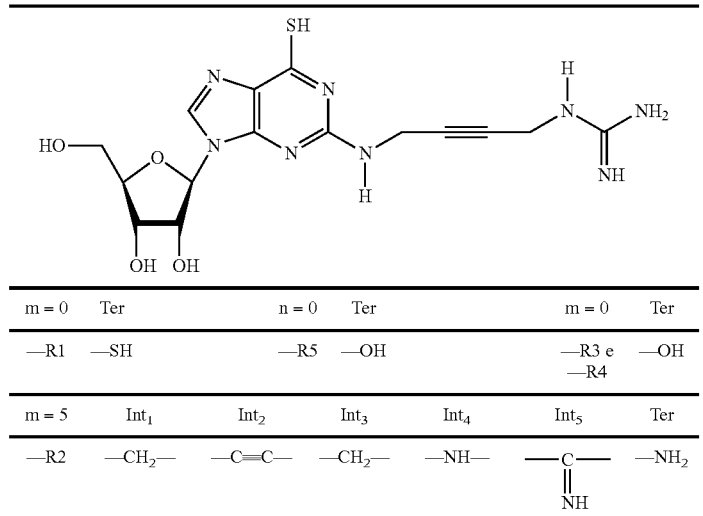

| m = 0 | Ter | n = 0 | Ter | m = 0 | Ter |
|---|---|---|---|---|---|
| —R1 | —SH | —R5 | —OH | —R3 e —R4 | —OH |

| m = 5 | $Int_1$ | $Int_2$ | $Int_3$ | $Int_4$ | $Int_5$ | Ter |
|---|---|---|---|---|---|---|
| —R2 | —$CH_2$— | —C≡C— | —$CH_2$— | —NH— | —C(=NH)— | —$NH_2$ |

N-2-(6"-Aspartate-2-butyne)-6-Thioguanosine

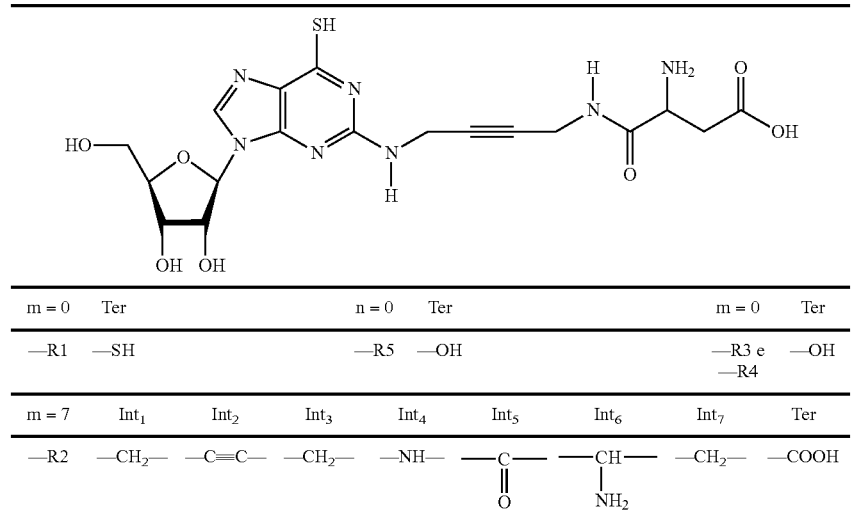

| m = 0 | Ter | n = 0 | Ter | m = 0 | Ter |
|---|---|---|---|---|---|
| —R1 | —SH | —R5 | —OH | —R3 e —R4 | —OH |

| m = 7 | $Int_1$ | $Int_2$ | $Int_3$ | $Int_4$ | $Int_5$ | $Int_6$ | $Int_7$ | Ter |
|---|---|---|---|---|---|---|---|---|
| —R2 | —$CH_2$— | —C≡C— | —$CH_2$— | —NH— | —C(=O)— | —CH($NH_2$)— | —$CH_2$— | —COOH |

N-2-(6"-Glutamate-2-butyne)-6-Thioguanosine
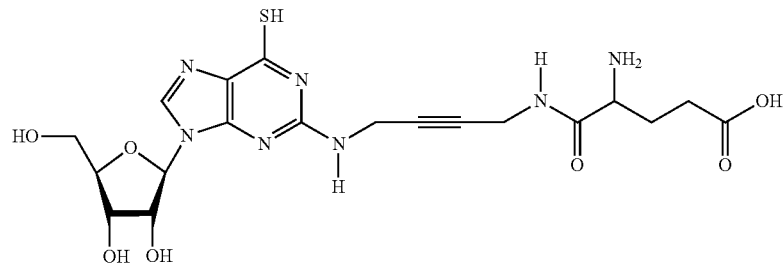
| m = 0 | Ter | | | n = 0 | Ter | | | m = 0 | Ter |
|---|---|---|---|---|---|---|---|---|---|
| —R1 | —SH | | | —R5 | —OH | | | —R3 e —R4 | —OH |
| m = 8 | Int$_1$ | Int$_2$ | Int$_3$ | Int$_4$ | Int$_5$ | Int$_6$ | Int$_7$ | Int$_8$ | Ter |
| —R2 | —CH$_2$— | —C≡C— | —CH$_2$— | —NH— | —C— ‖ O | —CH— \| NH$_2$ | —CH$_2$— | —CH$_2$— | —COOH |
N-2-(6"-Threonine-2-butyne)-6-Thioguanosine
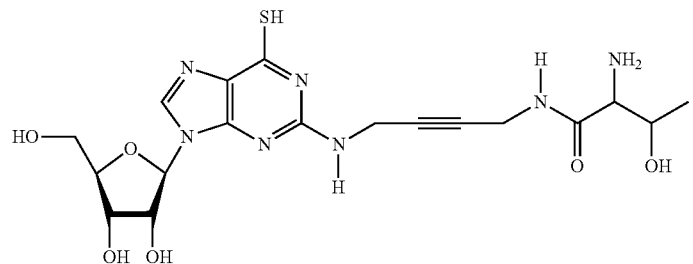
| m = 0 | Ter | | | n = 0 | Ter | | m = 0 | Ter |
|---|---|---|---|---|---|---|---|---|
| —R1 | —SH | | | —R5 | —OH | | —R3 e —R4 | —OH |
| m = 7 | Int$_1$ | Int$_2$ | Int$_3$ | Int$_4$ | Int$_5$ | Int$_6$ | Int$_7$ | Ter |
| —R2 | —CH$_2$— | —C≡C— | —CH$_2$— | —NH— | —C— ‖ O | —CH— \| NH$_2$ | —CH— \| OH | —CH$_3$ |

N-2-(6"-Serine-2-butyne)-6-Thioguanosine

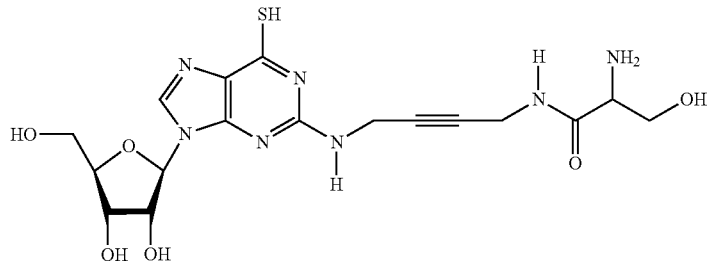

| m = 0 | Ter | | n = 0 | Ter | | m = 0 | Ter |
|---|---|---|---|---|---|---|---|
| —R1 | —SH | | —R5 | —OH | | —R3 e —R4 | —OH |

| m = 7 | Int₁ | Int₂ | Int₃ | Int₄ | Int₅ | Int₆ | Int₇ | Ter |
|---|---|---|---|---|---|---|---|---|
| —R2 | —CH₂— | —C≡C— | —CH₂— | —NH— | —C(=O)— | —CH(NH₂)— | —CH₂— | —OH |

N-2-(6"-Amino-2,4-hexadiyne)-6-Thioguanosine

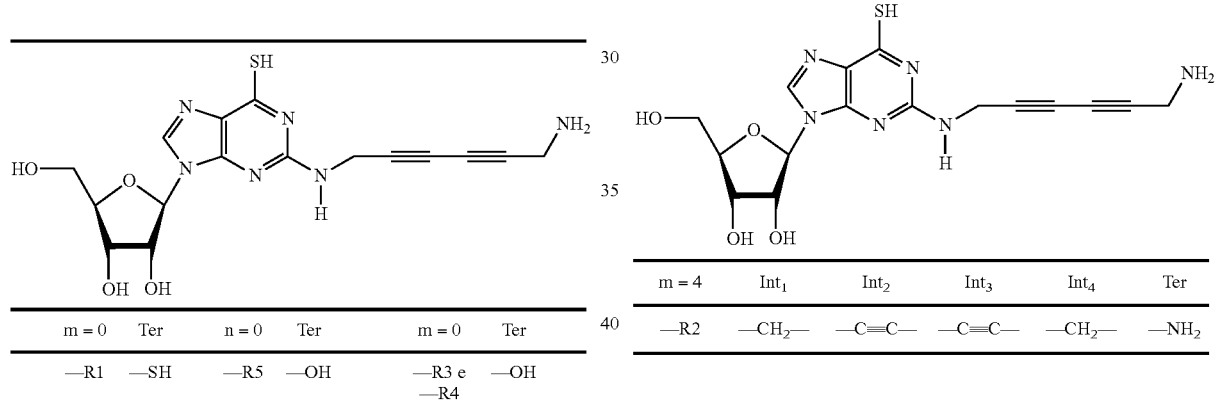

| m = 0 | Ter | | n = 0 | Ter | | m = 0 | Ter |
|---|---|---|---|---|---|---|---|
| —R1 | —SH | | —R5 | —OH | | —R3 e —R4 | —OH |

-continued

| m = 4 | Int₁ | Int₂ | Int₃ | Int₄ | Ter |
|---|---|---|---|---|---|
| —R2 | —CH₂— | —C≡C— | —C≡C— | —CH₂— | —NH₂ |

N-2-(6"-guanidino-2,4-hexadiyne)-6-Thioguanosine

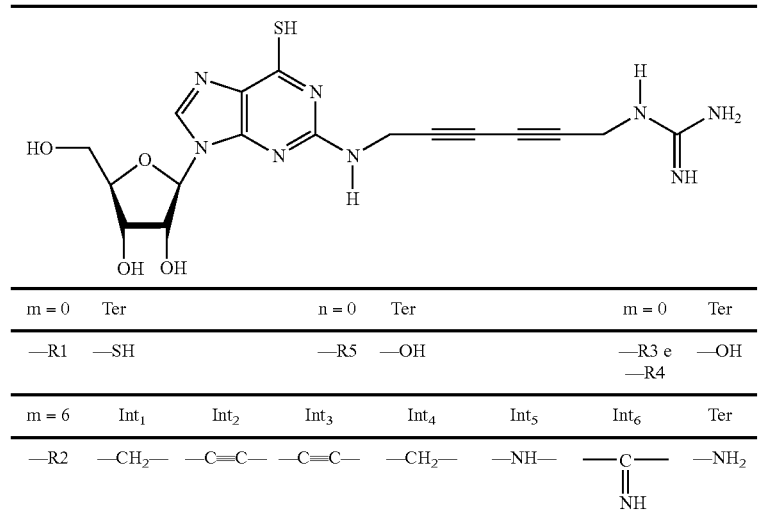

| m = 0 | Ter | | n = 0 | Ter | | m = 0 | Ter |
|---|---|---|---|---|---|---|---|
| —R1 | —SH | | —R5 | —OH | | —R3 e —R4 | —OH |

| m = 6 | Int₁ | Int₂ | Int₃ | Int₄ | Int₅ | Int₆ | Ter |
|---|---|---|---|---|---|---|---|
| —R2 | —CH₂— | —C≡C— | —C≡C— | —CH₂— | —NH— | —C(=NH)— | —NH₂ |

N-2-(6"-Aspartate-2,4-hexadiyne)-6-Thioguanosine

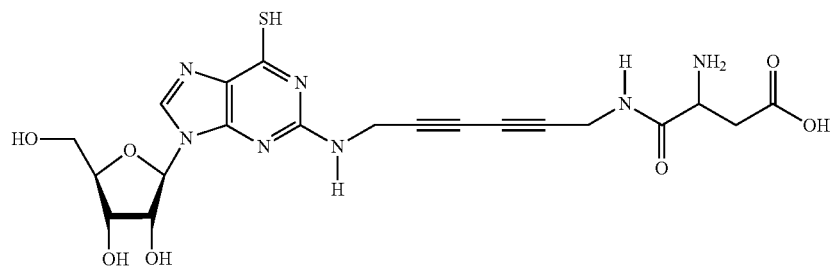

| m = 0 | Ter | | | | n = 0 | Ter | | | m = 0 | Ter |
|---|---|---|---|---|---|---|---|---|---|---|
| —R1 | —SH | | | | —R5 | —OH | | | —R3 e<br>—R4 | —OH |
| m = 8 | Int$_1$ | Int$_2$ | Int$_3$ | Int$_4$ | Int$_5$ | Int$_6$ | Int$_7$ | Int$_8$ | | Ter |
| —R2 | —CH$_2$— | —C≡C— | —C≡C— | —CH$_2$— | —NH— | —C—<br>‖<br>O | —CH—<br>|<br>NH$_2$ | —CH$_2$— | | —COOH |

N-2-(6"-Glutamate-2,4-hexadiyne)-6-Thioguanosine

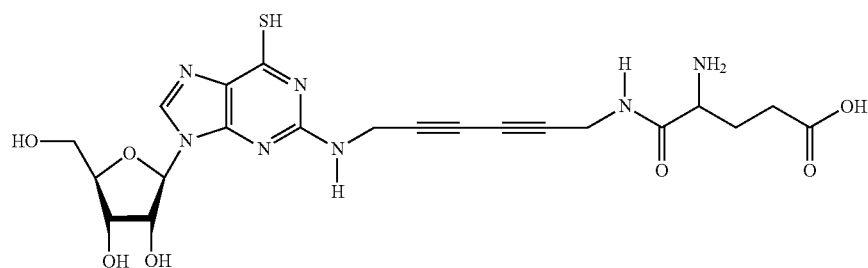

| m = 0 | Ter | | | | n = 0 | Ter | | | | m = 0 | Ter |
|---|---|---|---|---|---|---|---|---|---|---|---|
| —R1 | —SH | | | | —R5 | —OH | | | | —R3 e<br>—R4 | —OH |
| m = 9 | Int$_1$ | Int$_2$ | Int$_3$ | Int$_4$ | Int$_5$ | Int$_6$ | Int$_7$ | Int$_8$ | Int$_9$ | | Ter |
| —R2 | —CH$_2$— | —C≡C— | —C≡C— | —CH$_2$— | —NH— | —C—<br>‖<br>O | —CH—<br>|<br>NH$_2$ | —CH$_2$— | —CH$_2$— | | —COOH |

N-2-(6''-Threonine-2,4-hexadiyne)-6-Thioguanosine

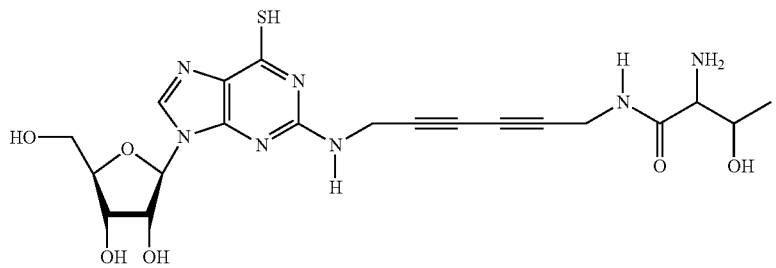

| m = 0 | Ter | | | | n = 0 | Ter | | | m = 0 | Ter |
|---|---|---|---|---|---|---|---|---|---|---|
| —R1 | —SH | | | | —R5 | —OH | | | —R3 e —R4 | —OH |
| m = 8 | $Int_1$ | $Int_2$ | $Int_3$ | $Int_4$ | $Int_5$ | $Int_6$ | $Int_7$ | $Int_8$ | | Ter |
| —R2 | —$CH_2$— | —C≡C— | —C≡C— | —$CH_2$— | —NH— | $\underset{O}{\overset{\parallel}{-C-}}$ | —CH— $\vert$ $NH_2$ | —CH— $\vert$ OH | | —$CH_3$ |

N-2-(6''-Serine-2,4-hexadiyne)-6-Thioguanosine

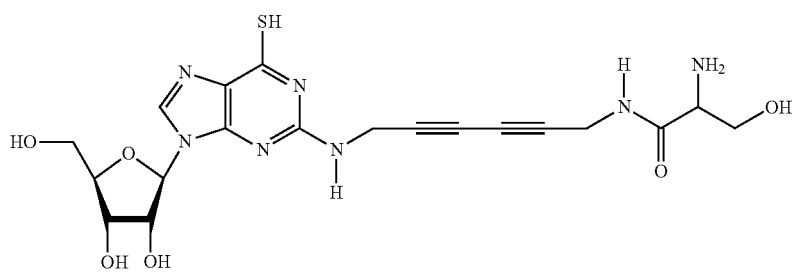

| m = 0 | Ter | | | | n = 0 | Ter | | | m = 0 | Ter |
|---|---|---|---|---|---|---|---|---|---|---|
| —R1 | —SH | | | | —R5 | —OH | | | —R3 e —R4 | —OH |
| m = 8 | $Int_1$ | $Int_2$ | $Int_3$ | $Int_4$ | $Int_5$ | $Int_6$ | $Int_7$ | $Int_8$ | | Ter |
| —R2 | —$CH_2$— | —C≡C— | —C≡C— | —$CH_2$— | —NH— | $\underset{O}{\overset{\parallel}{-C-}}$ | —CH— $\vert$ $NH_2$ | —$CH_2$— | | —OH |

Further compounds of the invention are disclosed, with reference titles indicated.
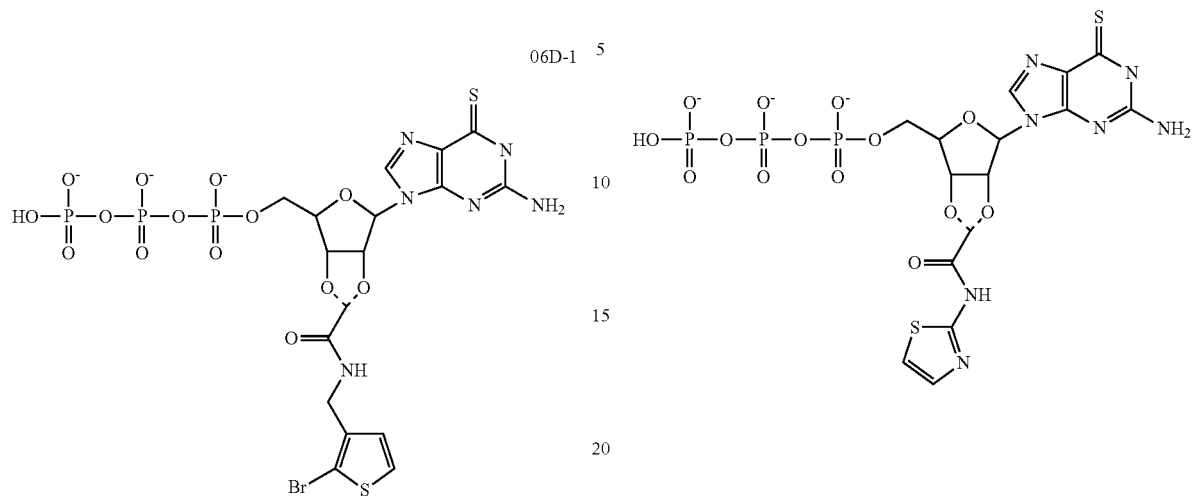
06D-1
06D-4
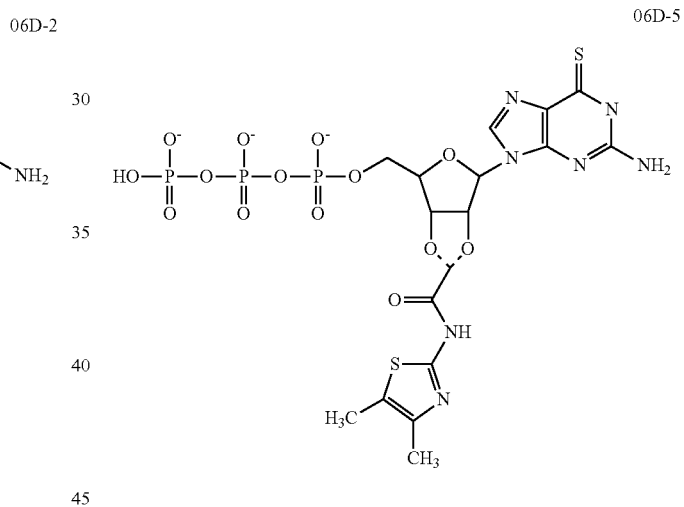
06D-2
06D-5
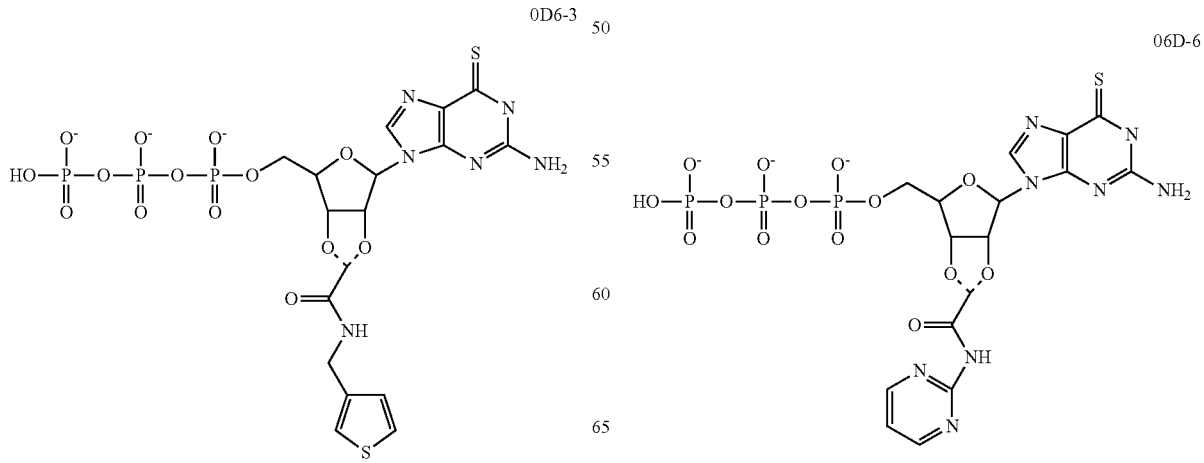
0D6-3
06D-6

06D-7
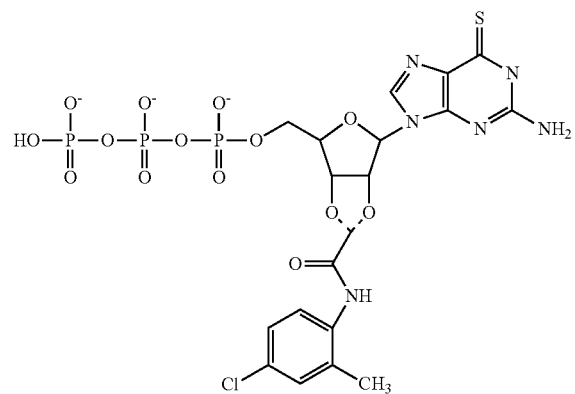
06D-10
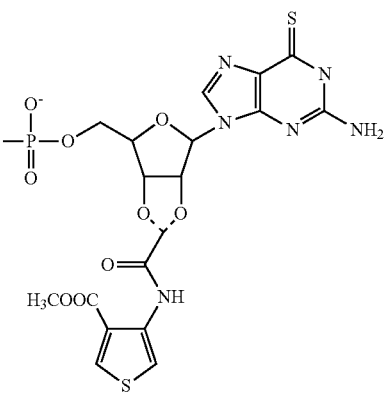
06D-8
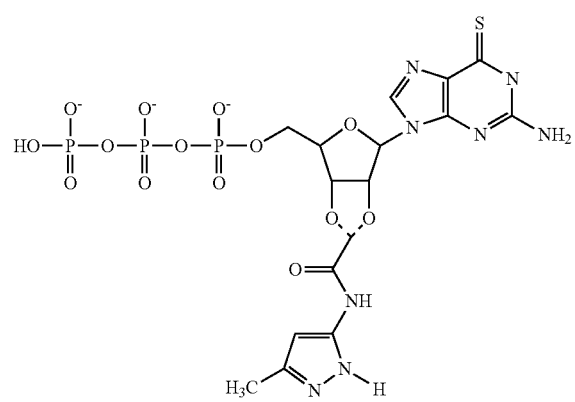
06D-11
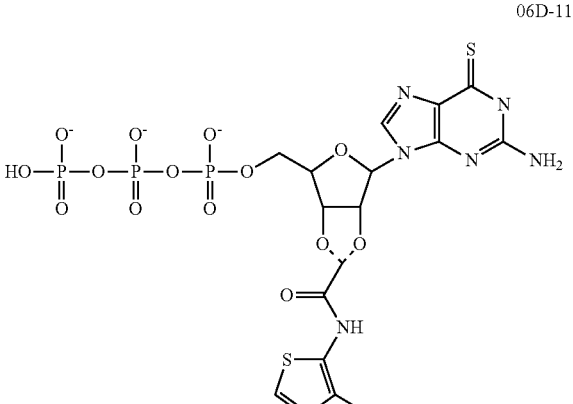
06D-9
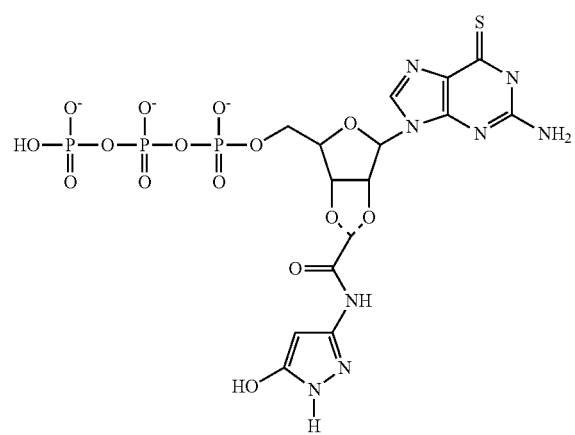
06D-12
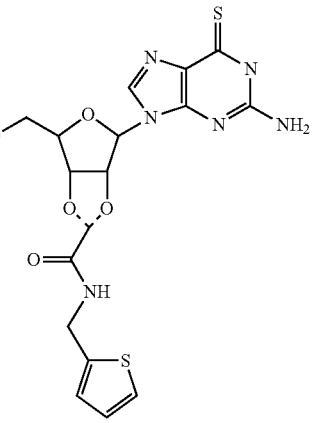

-continued
06D-13
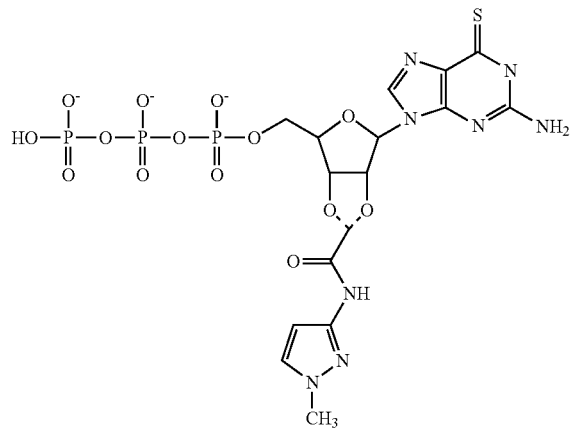
06D-14
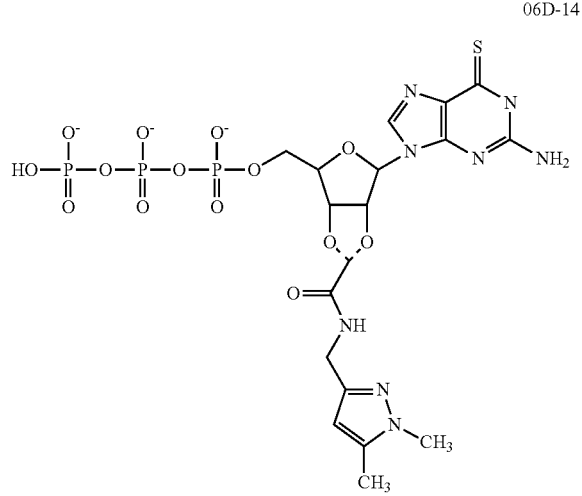
06D-15
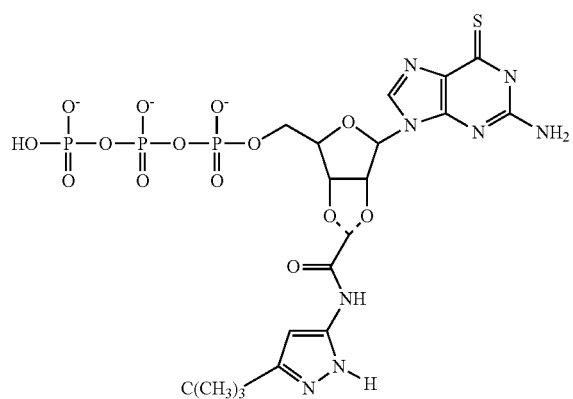
-continued
06D-16
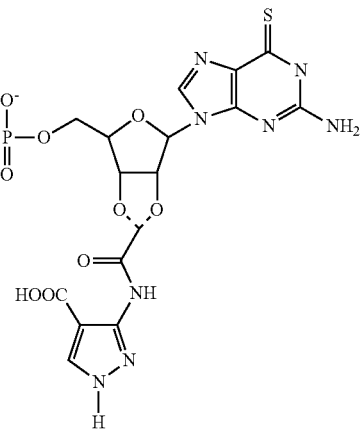
06D-17
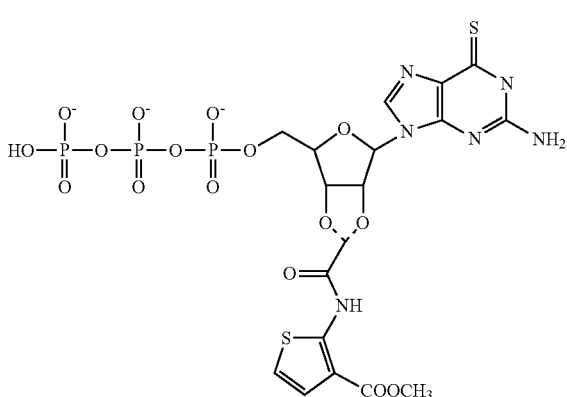
06D-18
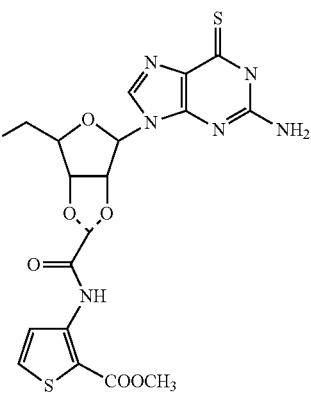

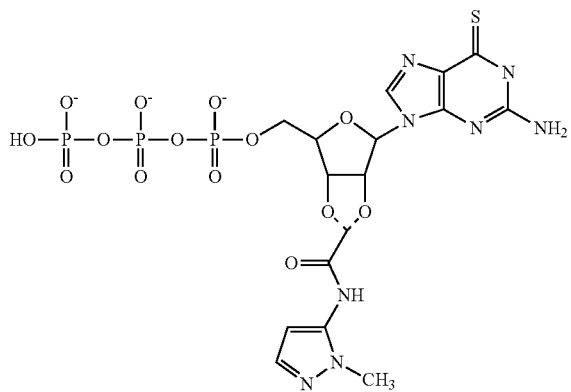
06D-19
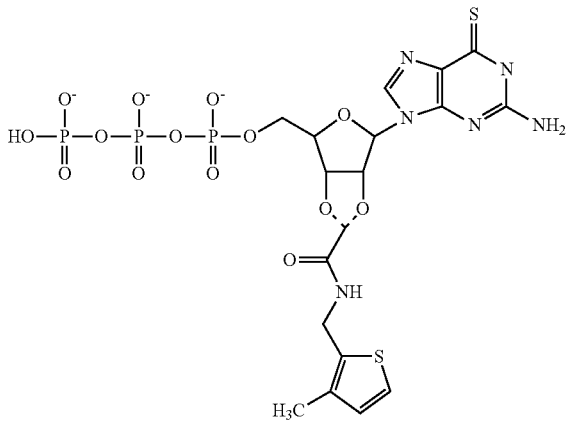
06D-22
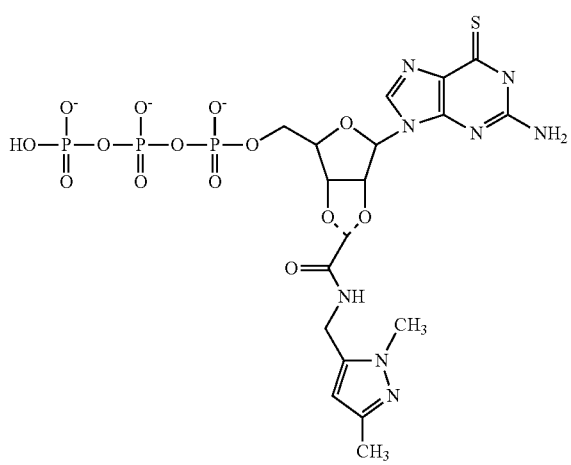
06D-20
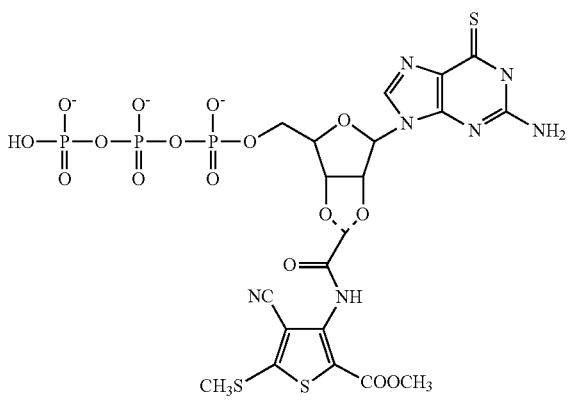
06D-23
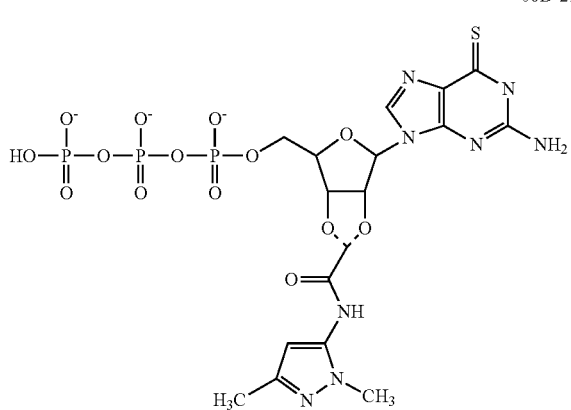
06D-21
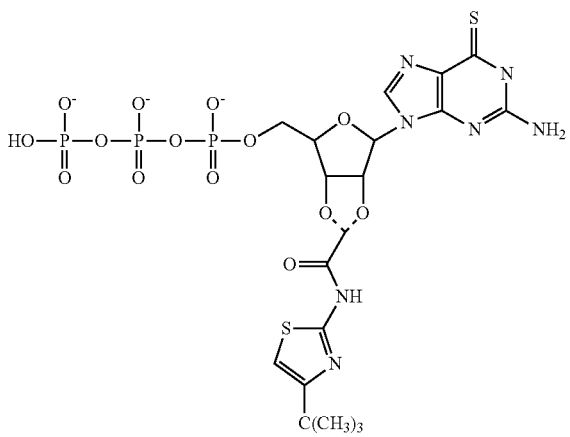
06D-24

75
-continued
06D-25
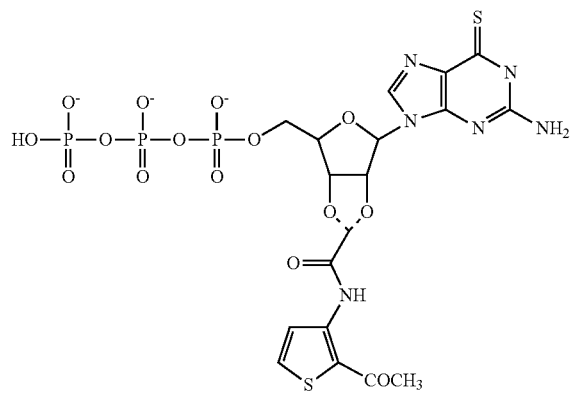
06D-26
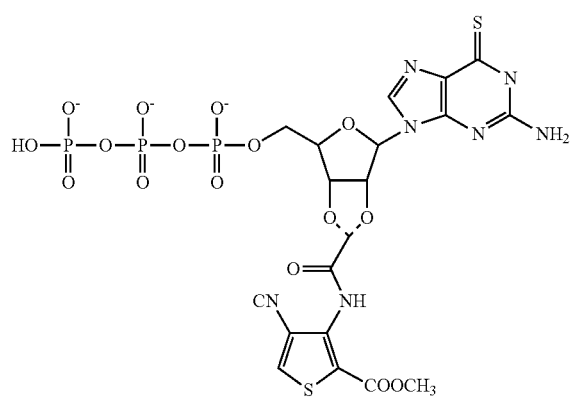
06D-27
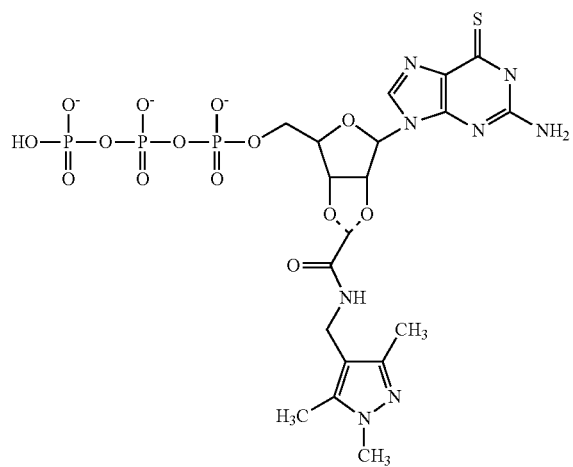
76
-continued
06D-28
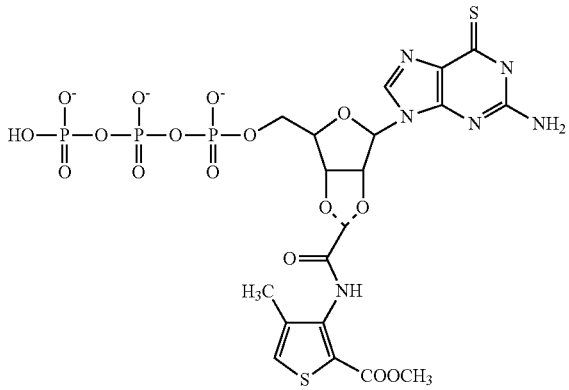
06D-29
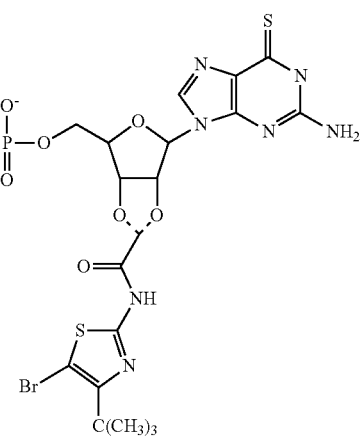
06D-30
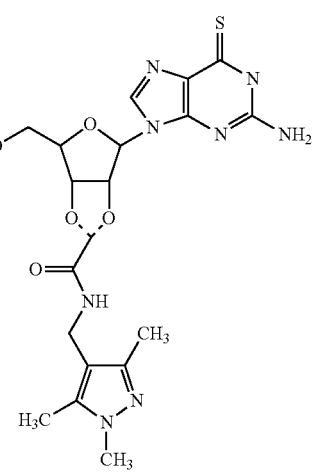

-continued 06D-31

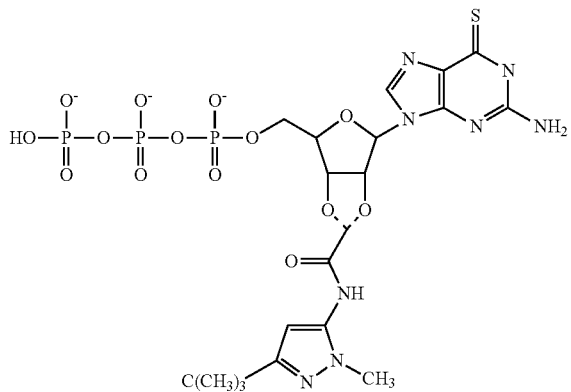

06D-32

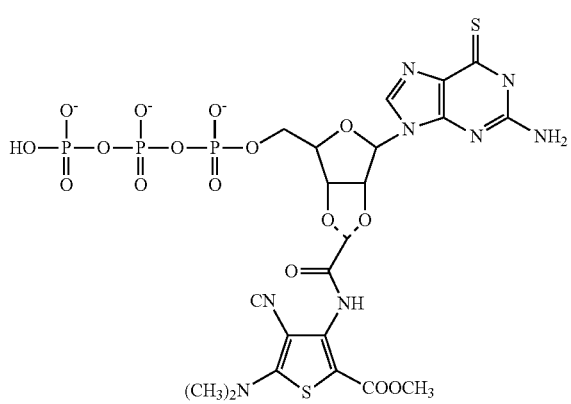

06D-33

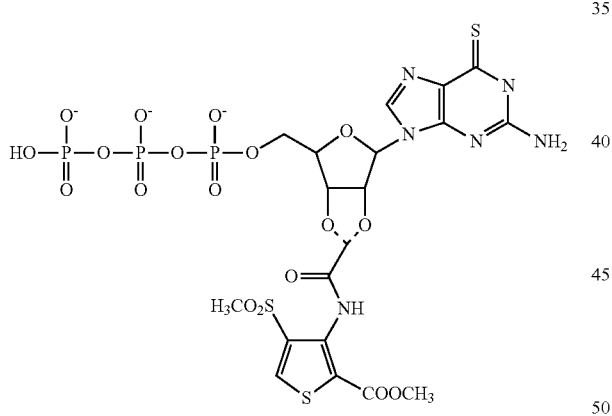

Compounds according to the present invention, can be advantageously used in medical field; therefore another object of the present invention are pharmaceutical composition comprising at least one of the compounds of the above mentioned formula (I) as active principle and one or more pharmaceutically acceptable co-adjuvants or excipients, that are known to those skilled in the art and currently in use in the pharmaceutical technology.

It is an object of the invention to provide for compounds for the preparation of an immunosuppressive drug. Its uses and therapeutical and medical uses thereof. for It is an object of the present invention to provide the compounds and compositions of the invention, and their uses, in the following methods of treatment, and/or therapy; the prevention of rejection of organ transplants (e.g. kidney, heart, lung, pancreas, liver transplantation) and of post-transplant nephropathy and in the treatment of pathologies in which immune system is involved, such as, for instance, inflammatory chronic intestinal diseases, such as Crohn's disease, ulcerous rectocolitis, indeterminate colitis, or auto-immune enteropathy, active chronic hepatitis, rheumatoid arthritis, Still's disease, systemic lupus erythematous, acquired haemolytic anaemia, idiopathic thrombocytopenia, polyarthritis nodosa, vasculitis, polyangitis, polymyositis, myasthenia gravis, sarcoidosis, lipoid nephritis, multiple sclerosis, dermatomyositis, pemphigus vulgaris, primary biliary cirrhosis, primary sclerosing cholangitis, recurrent multiform erythema, chronic actinic dermatitis, gangrenous hypoderm, ptyriasis rubra, Wegener's granulomatosis, cutaneous vasculitis, atopic dermatitis, psoriasis, pimply pemphigoid and, in general, in the immunosuppressive treatment in addition to radiotherapy, corticosteroids and other cytotoxic agents. In addition, the compounds according to the present invention can be advantageously used for the preparation of a medicament for the treatment of cancer.

The present invention further relates to the use of labelled compounds of formula (I), particularly with $R_3$ or $R_4$ selected from

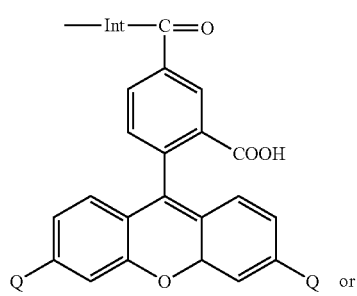 or

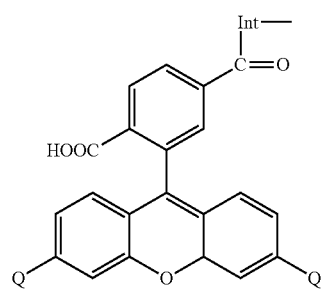

wherein Q is selected from —OH (FAM) or —N(CH$_3$)$_2$ (TAMRA) as probes for the evaluation of the binding properties of the compounds of formula (I) by the RacI/Vav system.

According to a further aspect, the present invention refers to a process for the preparation of compounds of formula (I), (Ia) and (II), wherein the introduction of the —NH—R group at the 2 position of guanosine ring comprises the following steps:

a) protection of the NH moiety of tri-O-acetyl-inosine;

b) oxidative guanosine ring-opening and O-deprotection;

c) guanosine ring-closing and introduction of a SH group at the 2 position of the guanosine ring through the use of CS$_2$;

d) replacing the SH group at the 2 position with an amino-linker by using an excess of an aliphatic diamine. The process may further comprise an additional step e) of protection of ribose OH groups and of the primary amine group by acetylation, and, moreover, an additional step f) of thiolation of C=O groups through the use of Lawesson's reagent.

The present invention will be now described, for illustrative but not limitative purposes, according to its preferred embodiments, with particular reference to the Figures of the enclosed drawings.

DESCRIPTION OF DRAWINGS

FIG. 6: Results of biological activity of compounds compiled in FIG. 5.

FIG. 7: list of further compounds of the invention, as well as providing key to some of the shorthand used in identifying some of the molecules. It will be noted that some compounds have different enantiomeric forms, and the representations in FIG. 7 may show an alternative enantiomeric form than that discussed in the text.

EXAMPLE 1

Figure 1:
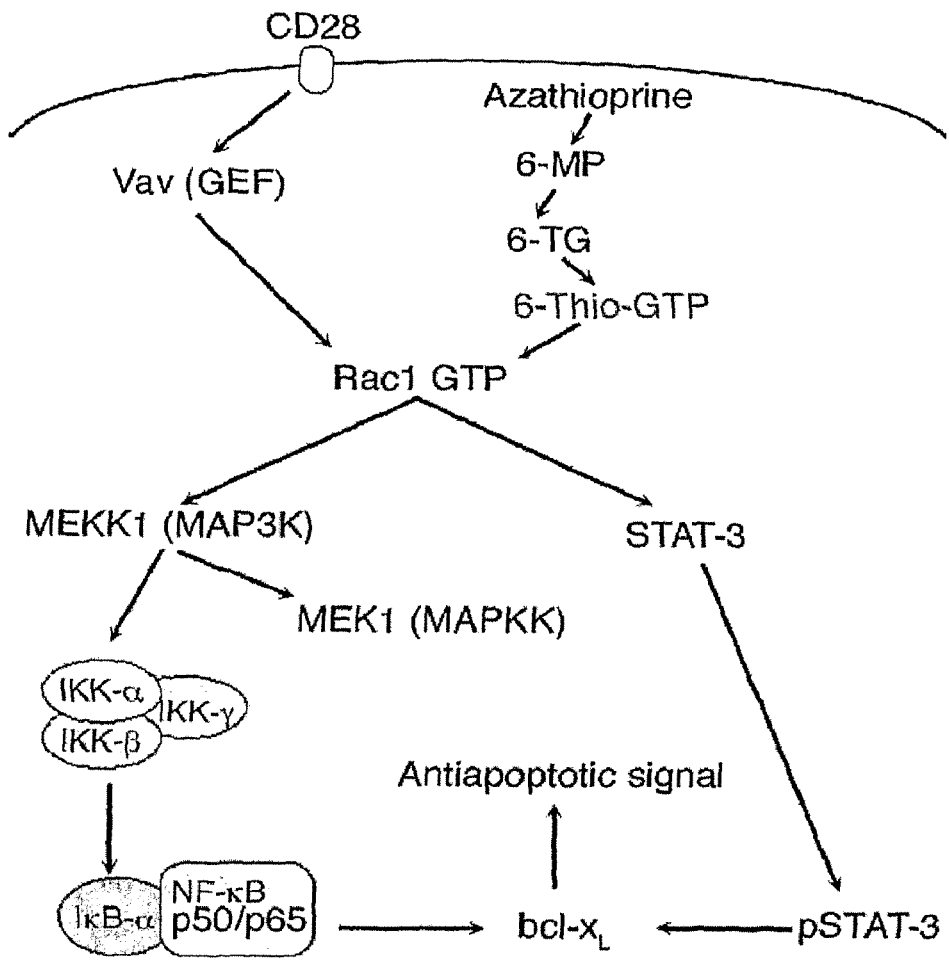
FIG. 1 shows the scheme of the mechanism of action of the apoptosis inhibition and of the action of azathioprine.

Process for the Preparation of 2-substituted-6-thio-guanosine Nucleotides

Preparation of 2',3',5'-Tri-O-acetyl-1-[(2-methoxyethoxy)methyl] inosine (Kohyoma et al., 2003)

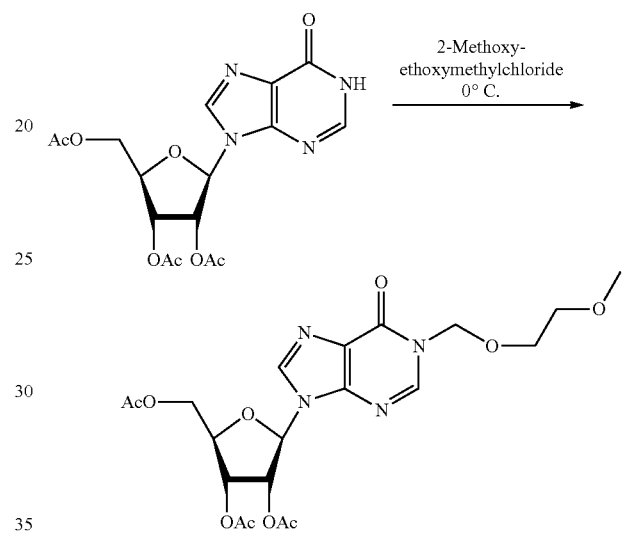

Inosine-2',3',5'-triacetate (4 g, 10.2 mmol) was dissolved in 100 ml dichloromethane and the solution was treated with 1.4 ml (12.2 mmol) 2-methoxyethoxymethylchloride at 0° C. in the presence of diisopropylethylamine as a supportive base. After 1 hour the reaction was quenched with water. The solution was stirred for 30 min and chloroform was added afterwards.

The aqueous layer was extracted with chloroform and the combined and washed organic layers were concentrated to dryness. The reaction yielded 3.93 g (8.2 mmol, 80%) of 2',3',5'-Tri-O-acetyl-1-[(2-methoxyethoxy)methyl] inosine after chromatographic purification (silica gel, EtOAc-MeOH, 50:1).

Preparation of 5-Amino-1-O-ribofuranosylimidazole-4-carboxamide (Kohyoma et al., 2003)

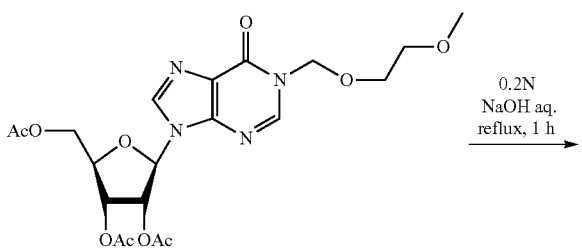

-continued

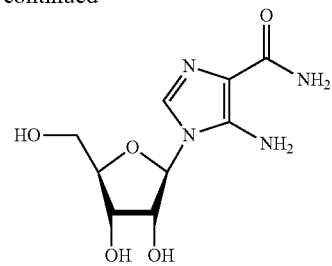

Aqueous ammonia solution (28%, 20 ml) was added to a solution of 2',3',5'-Tri-O-acetyl-1-[(2-methoxyethoxy)methyl] inosine (3.5 g, 7.3 mmol) in 50 ml methanol. The reaction mixture was stirred for 1 hour at room temperature and concentrated, yielding the deprotected nucleoside (2.44 g, 6.9 mmol, 95%). This product was used in the next step without further purification.

The nucleoside (2.44 g, 6.9 mmol) was refluxed with 50 ml aqueous sodium hydroxide (0.2 M) for 1 hour, cooled to room temperature, neutralized with HCl (6 M) and evaporated to dryness. The residue was dissolved in ethanol, filtered from insoluble material and concentrated to dryness. Purification of the crude product by column chromatography (silica gel, $CHCl_3$:MeOH, 3:1) gave 1.32 g (5.11 mmol, 70%) of 5-Amino-1-β-ribofuranosylimidazole-4-carboxamide.

Preparation of 2-Mercaptoinosine (Imai et al., 1971)

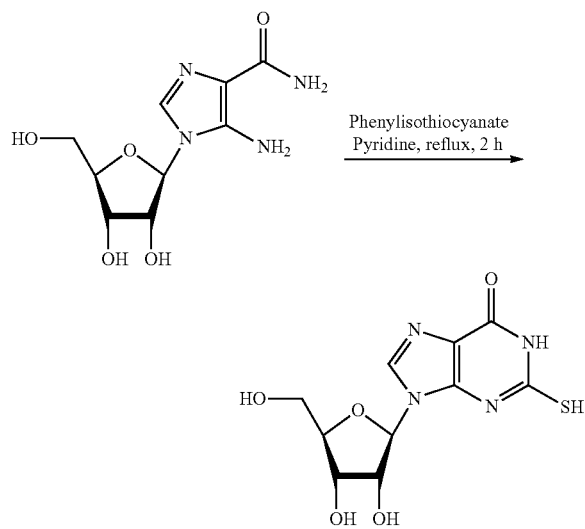

The 5-Amino-1-β-ribofuranosylimidazole-4-carboxamide (1.3 g, 5 mmol) was dissolved in pyridine and 18 ml (15 mmol) phenyl-isothiocyanate were added slowly. The reaction mixture was refluxed for 2 hours under argon atmosphere. The solution was cooled to room temperature, the precipitate collected by filtration and washed with diethyl ether. The obtained pyridinium salt of the product was dissolved in aqueous sodium hydroxide (15%, 40 ml). The solution was heated 30 minutes at 60° C. and concentrated under vacuum. Methanol was then added and the solution was kept in the refrigerator overnight. After 20 hours the precipitated colourless prisms were collected by filtration to give 1.2 g (80%) 2-Mercaptoinosine.

According to an alternative method of preparation, compound-Amino-1-β-ribofuranosylimidazole-4-carboxamide (1.3 g, 5 mmol) was added to a solution of sodium hydroxide (1 g, 25 mmol) in 20 ml of methanol at 30° C. Carbon disulfide (1.9 g, 25 mmol) was added, and the solution was heated in an autoclave at 180° C. for 3 hours. The mixture was cooled to room temperature, the precipitate was filtered off, washed with cold methanol and recrystallized from water to yield 1.1 g (3.8 mmol, 75%) 2-Mercaptoinosine.

Preparation of N-2-(6"-aminohexyl)-Guanosine

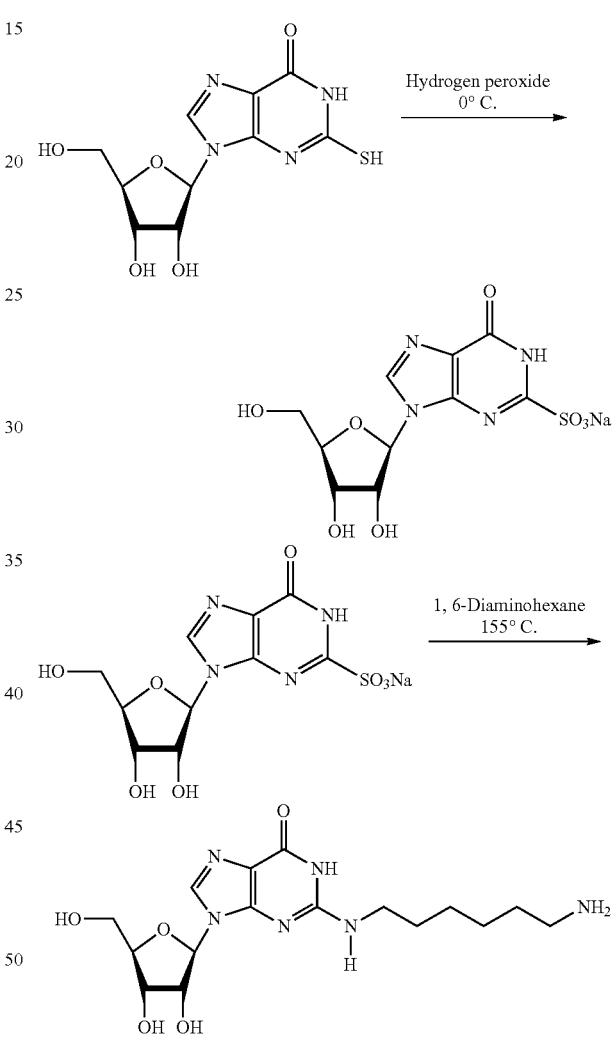

2-Mercaptoinosine (1 g, 3 mmol) was dissolved in 100 ml water and cooled to 0° C. A clear solution was obtained after ultrasonic irradiation. Hydrogen peroxide (1 ml, 9 mmol) was added within 20 min under vigorous stirring. After 1 hour of stirring at 0° C., HPLC chromatography indicated that the starting compound has been completely oxidized to the sodium salt of Inosine-2-sulfonic acid. Without further purification, the resulting solution was treated with an excess of 1,6-diaminohexane (20 g, 200 mmol). The mixture was refluxed for 2.5 hours at 155° C. The excess of 1,6-diaminohexane was removed by vacuum distillation to give an orange residue. N-2-(6"-Aminohexyl)-guanosine (0.85 g, 2.2 mmol, 50%) was obtained after purification of the crude product by column chromatography (silica gel RP-18, linear gradient from 100% water to 100% methanol). Preparation of 2',3',5'-triacetyl-N-2-(6"-acetamide-hexyl)-guanosine (Ostermann et al., 1999)

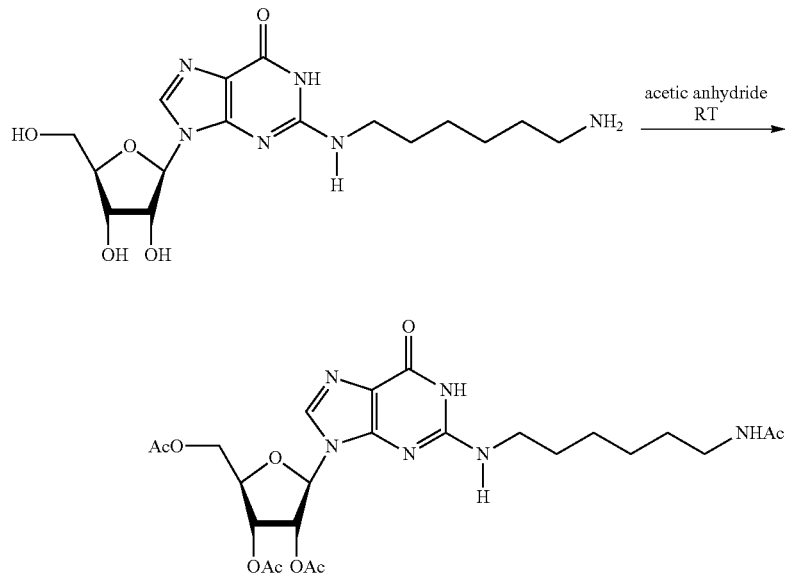

A solution of nucleoside (220 mg, 0.575 mmol) in 20 ml dry pyridine was stirred with 1 ml (10 mmol) acetic anhydride at room temperature for 15 hours under argon atmosphere. The solvent was removed under vacuum and the residue dissolved in a mixture of $CHCl_3$ (10 ml) and $CH_3OH$ (2 ml). This solution was loaded on silica gel and eluted with $CHCl_3$/$CH_3OH$ (5:1) to give 284.7 mg (0.52 mmol, 90%) of fully protected nucleoside.

Preparation of 2',3',5'-triacetyl-N-2-(6"-thioacetamido-hexyl)-6-thioguanosine

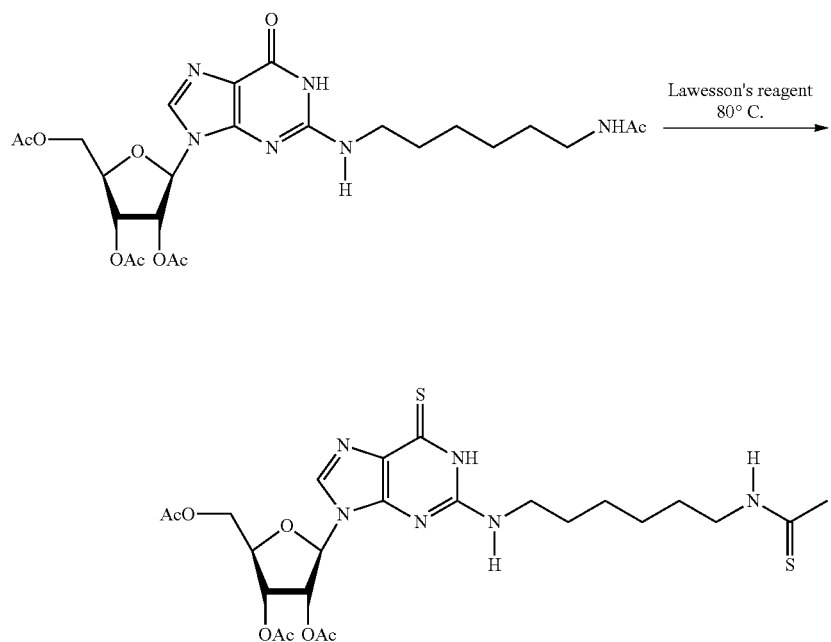

Dioxane (200 ml) was added to the fully protected nucleoside (5.03 g, 9.13 mmol). After addition of 8 g (19.8 mmol) of Lawesson's reagent the suspension was vigorously stirred for 2 hours at 80° C. The initially opaque reaction mixture became clear after 10 minutes. The solution was cooled at room temperature and the solvent was evaporated by vacuum distillation. Purification of the raw product by column chromatography (silica gel, CHCl$_3$), resulted in 2',3',5'-triacetyl-N-2-(6"-thioacetamido-hexyl)-6-thioguanosine (2.92 g, 5.02 mmol) in 55% yield.

EXAMPLE 2

Process for the Preparation of Analogous of ribose-modified 6-thio-guanosine-triphosphate Preparation of 6-Thio-Guanosine-Triphosphate (Ludwig, 1981)

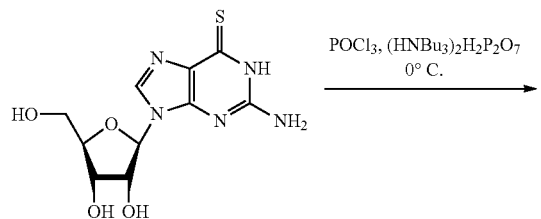

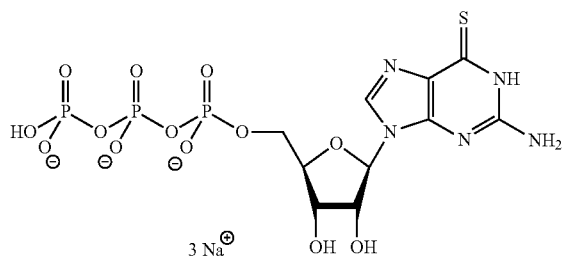

Under argon atmosphere, 6-thio-guanosine (1 g, 3.34 mmol) was dissolved in 6 ml trimethylphosphate. The solution was cooled to 0° C. and 1.3 ml of Lutidine were added. After 10 minutes, 0.4 ml (4.4 mmol) phosphorous oxychloride was carefully added to the solution. After 1 hour the excess of POCl$_3$ was removed under vacuum within ten minutes.

The solution of the initially formed intermediate dichlorophosphate was then treated with a solution of tri-n-butyl ammonium pyrophosphate (17 ml, 100 mM) in dimethylformamide. After 2 minutes, the reaction was quenched by adding 100 ml of 0.25 M triethylammonium bicarbonate buffer. Purification by ion exchange chromatography gave 6-Thio-Guanosine-Triphosphate (0.5 g, 1 mmol, 30%).

Preparation of 2'/3'-EDA-6-Thio-Guanosine-triphosphate

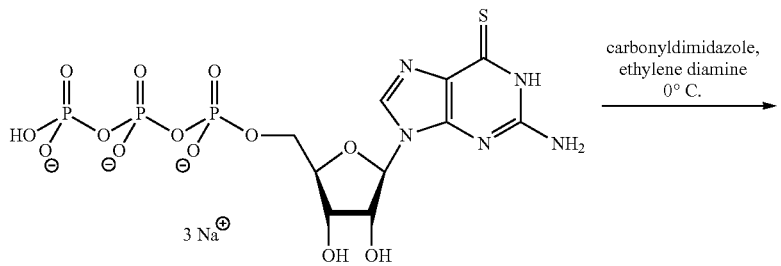

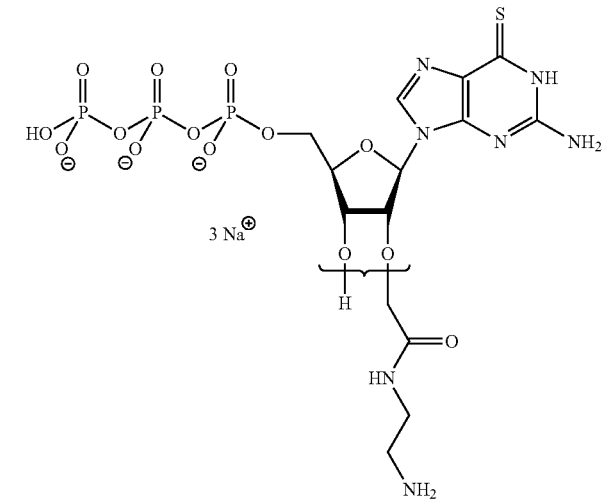

The dry tributylammonium salt of compound (0.5 mmol) was treated with 500 mg carbonyldiimidazole in 25 ml dimethylformamide. The resulting mixture was stirred for 6 hours at 0° C., brought to room temperature and 0.2 ml methanol and subsequently 0.3 ml ethylene diamine were added.

The resulting precipitate was centrifuged down and dissolved in water. The solution was adjusted to pH 2, in order to decompose the resulting intermediate phosphoramidate at the triphosphate moiety. After 18 hours, pH was adjusted to 7.5 and the solvent was subsequently removed under reduced pressure. Purification of the crude product by ion exchange chromatography gave 116 mg (0.4 mmol, 80%) 2'/3'-EDA-6-Thio-Guanosine-triphosphate.

Preparation of TAMRA-2'/3'-EDA-6-Thio-Guanosine-Triphosphate

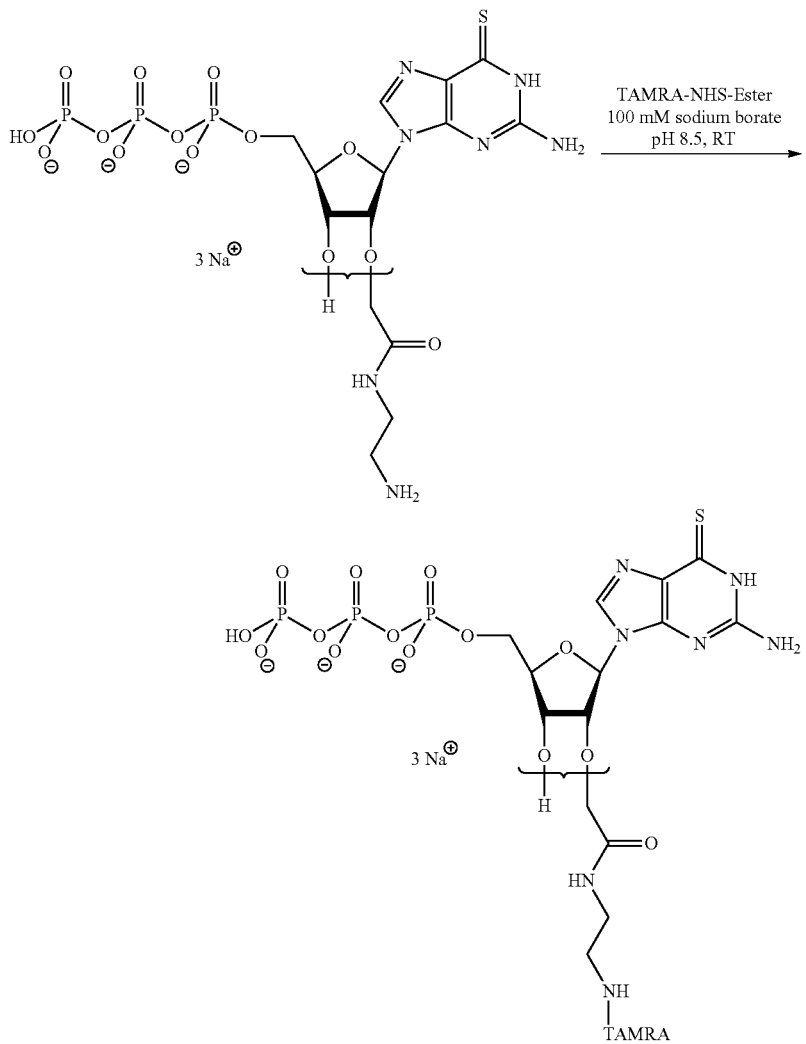

The N-hydroxy-succinimide ester of TAMRA (1 mg, 2 µmol) was dissolved in 200 µl of dry dimethylformamide and added to a solution of 1 mg (3 µmol) of 2'/3'-EDA-6-Thio-Guanosine-Triphosphate in 500 µl of 100 mM sodium borate buffer (pH 8.5) at room temperature. After 2 hours, the reaction mixture was quenched with methanol. The TAMRA labelled product was obtained in 70% yield (2.4 mg, 1.4 µmol) after workup of the reaction mixture by reversed phase HPLC.

EXAMPLE 3

Synthesis of 2-Substituted 6-Thio-Guanosine nucleotides

Preparation of N-2-(6"-Thioacetamido-hexyl)-6-Thioguanosine (10)

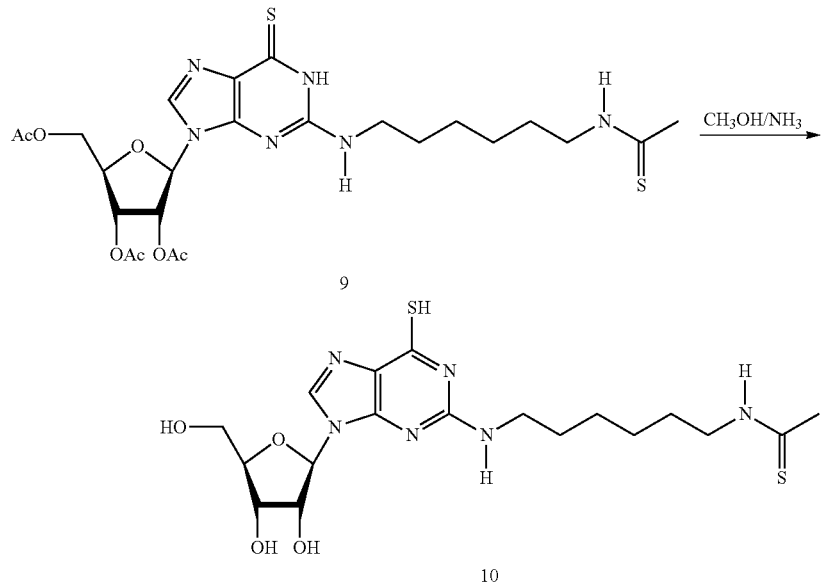

A, 7 M solution of ammonia in methanol (70 ml) was added to the fully protected nucleoside 9 (1.15 g, 1.97 mmol). The solution was stirred at room temperature for 20 hours. The solvent was removed by distillation to give an off white residue. The crude N-2-(6"-thioacetamido-hexyl)-6-Thioguanosine (10) (0.85 g, 1.8 mmol, 95%) was used without further purification.

Preparation of N-2-(6"-Aminohexyl)-6-Thioguanosine (11)

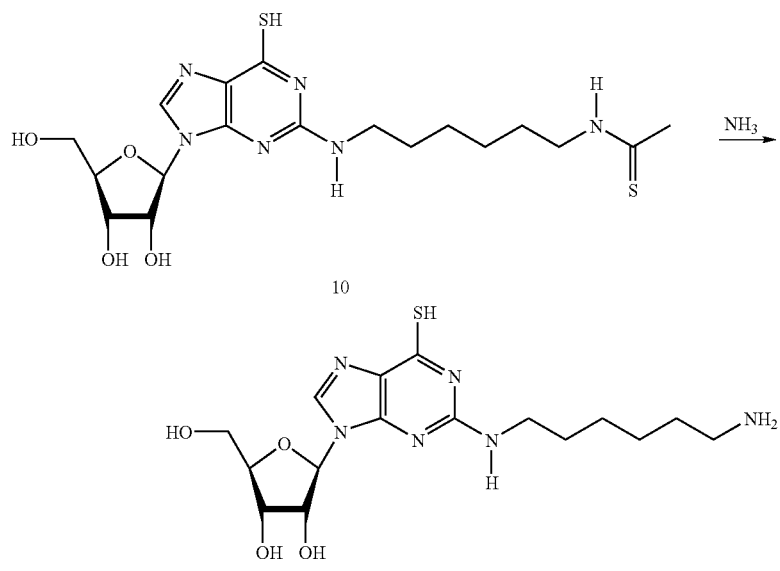

A solution of nucleoside 10 (0.1 g, 0.22 mmol) in 5 ml NH$_3$/H$_2$O (30%) was stirred for 90 minutes at 80° C. The solvent was removed in vacuo and the residue was dissolved in water (2 ml). N-2-(6"-Aminohexyl)-6-Thioguanosine (11) (0.80 g, 2.0 mmol, 91%) was obtained after purification of the crude product by column chromatography (silica gel RP-18, linear gradient from 100% water to 100% methanol).

Preparation of N-2-(6"-Guanidino-hexyl)-6-Thioguanosine (12)

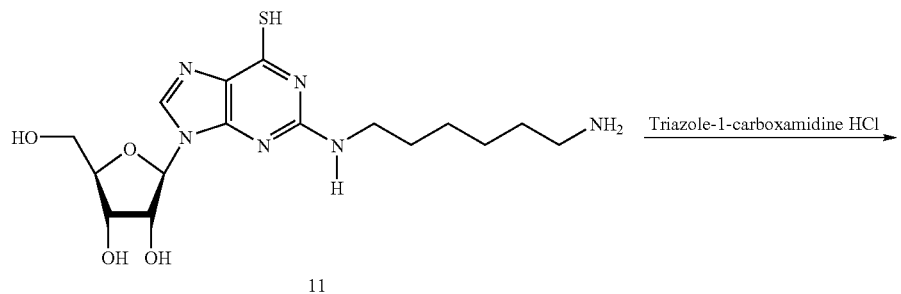

11

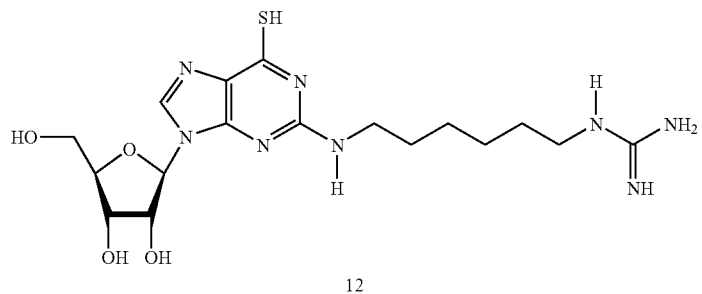

12

N-2-(6"-Aminohexyl)-6-Thioguanosine (11) (0.091 g, 0.23 mmol) was dissolved in 1 ml DMF and the resulting solution was treated with 0.34 g (0.23 mmol) Triazole-1-carboxamidine hydrochloride at room temperature in the presence of 39 μl (0.23 mmol) N-Ethyl-diisopropylamine acting, as a supportive base. After 2 hours, the reaction mixture was evaporated to dryness. Purification of the crude product by reversed phase chromatography (silica gel RP 18, linear gradient from 100% H$_2$O to 100% ACN) gave 0.92 g (0.21 mmol, 90%) of N-2-(6"-Guanidino-hexyl)-6-Thioguanosine (12).

Preparation of N-2-(6"-Aminohexyl)-6-Thioguanosine-5'-monophosphate (13)

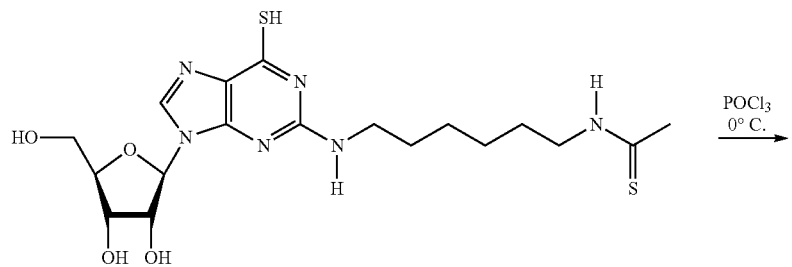

9

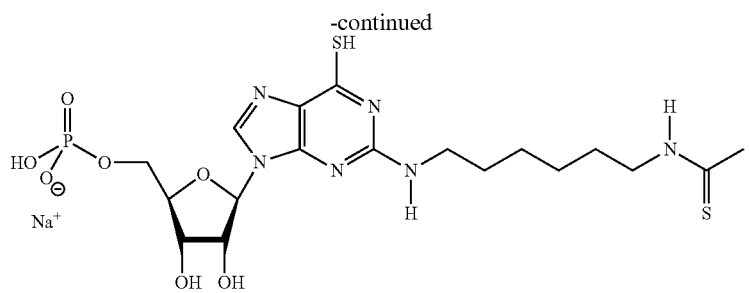

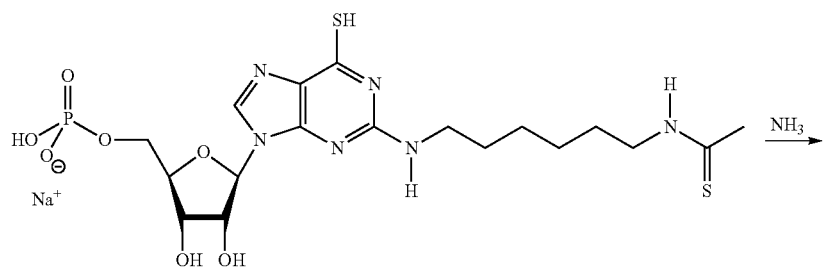

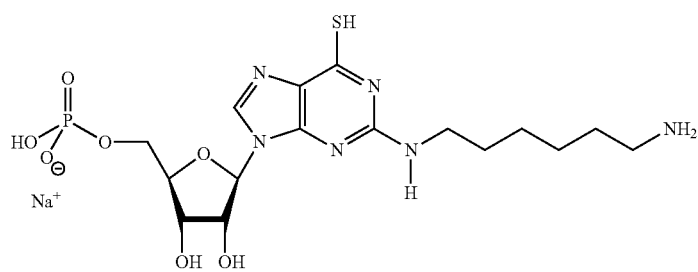

13

Under argon atmosphere, nucleoside 9 (0.3 g, 0.6 mmol) was dissolved in 3 ml trimethylphosphate. The solution was cooled to 0° C. and treated with 0.3 ml of Lutidine.

After 10 minutes, 0.15 ml (1.1 mmol) phosphorous oxychloride was carefully added. After 1 hour, the excess of $POCl_3$ was removed in vacuo within ten minutes.

The solution was quenched by adding 100 ml of 0.25 M (pH 7.5) triethylammonium bicarbonate buffer. Purification by ion exchange chromatography gave N-2-(6"-thioacetamido-hexyl)-6-Thioguanosine-5'-monophosphate. The product was dissolved in 5 ml $NH_3/H_2O$ (30%) and stirred for 90 minutes at 80° C. The solvent was subsequently removed in vacuo. N-2-(6"-Aminohexyl)-6-Thioguanosine-5'-monophosphate (13) (0.17 g, 0.36 mmol, 60%) was obtained after purification of the crude product by ion exchange chromatography.

Preparation of N-2-(6"-Guanidino-hexyl)-6-Thioguanosine-5'-monophosphate (14)

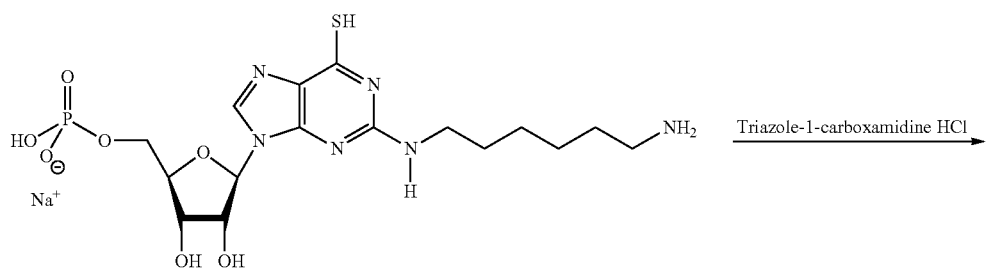

13

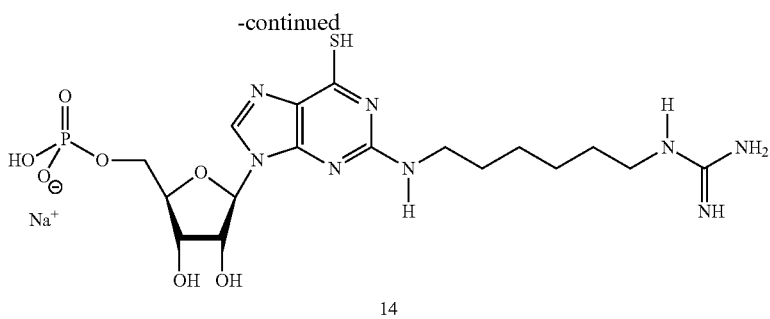

14

N-2-(6''-Aminohexyl)-6-Thioguanosine-5'-monophosphate (13) (0.053 g, 0.11 mmol) was dissolved in a mixture of 0.8 ml water and 0.5 ml DMF. The solution was subsequently treated with 0.16 g (0.11 mmol) Triazole-1-carboxamidine hydrochloride at room temperature in the presence of 18 µl (0.11 mmol) N-Ethyl-diisopropylamine, acting as a supportive base. After 16 hours, the reaction mixture was concentrated to dryness. Purification of the crude product by reversed phase chromatography (silica gel RP 18, linear gradient from 100% H₂O to 100% ACN) gave 0.037 g (0.072 mmol, 65%) of N-2-(6''-Guanidino-hexyl)-6-Thioguanosine-5'-monophosphate (14).

EXAMPLE 4

Synthesis of Ribose-Modified 6-Thio-GTP Analogs

Preparation of Aspartate-2'/3'-EDA-6-Thio-Guanosine-Triphosphate (4)

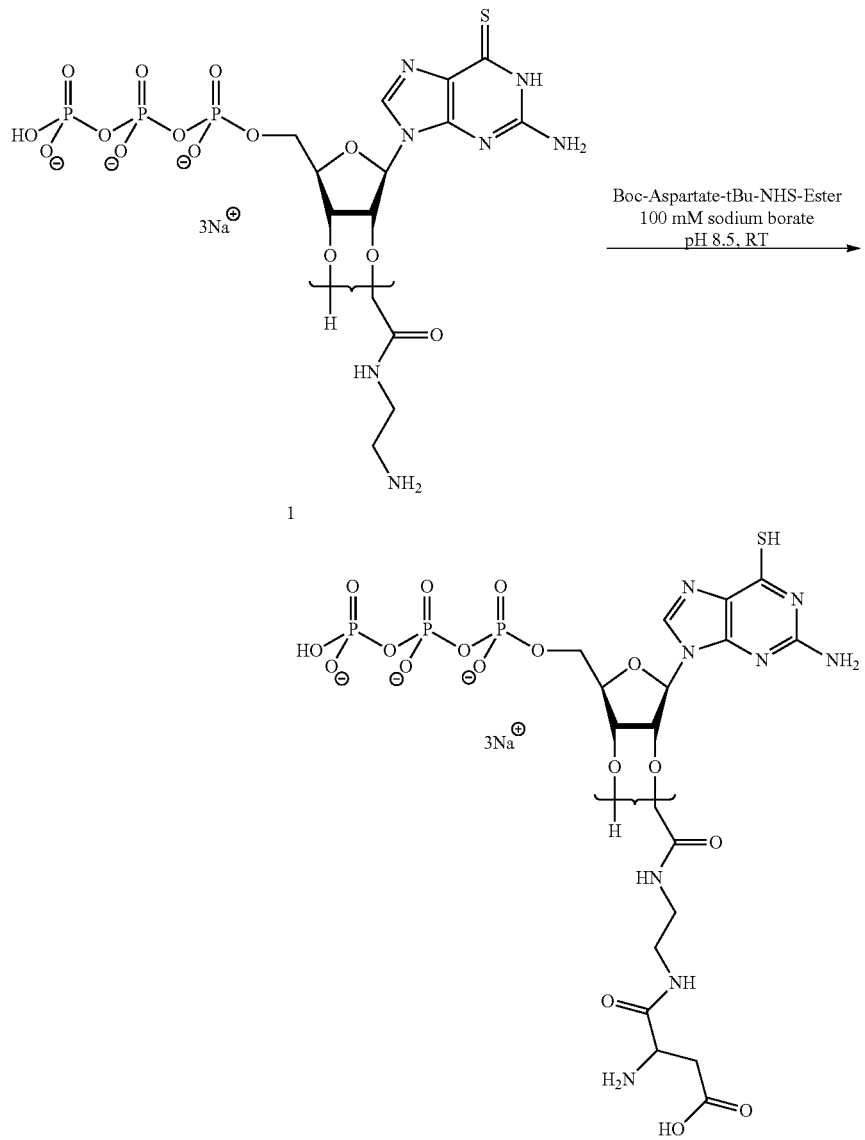

The N-hydroxy-succinimide ester of Boc/tBu protected Aspartate (2.8 mg, 7 µmol) was dissolved in 200 µl of dry DMF and added to a solution of 1 (5 mg, 7 µmol) in 500 µl of 100 mM sodium borate buffer (pH 8.5) at room temperature. After 16 hours, the reaction mixture was quenched with methanol. The Aspartate derivative 4 was obtained in 70% yield (3.6 mg, 4.9 µmol) after workup of the reaction mixture by reversed phase HPLC.

Preparation of Glutamate-2'/3'-EDA-6-Thio-Guanosine-Triphosphate (5)

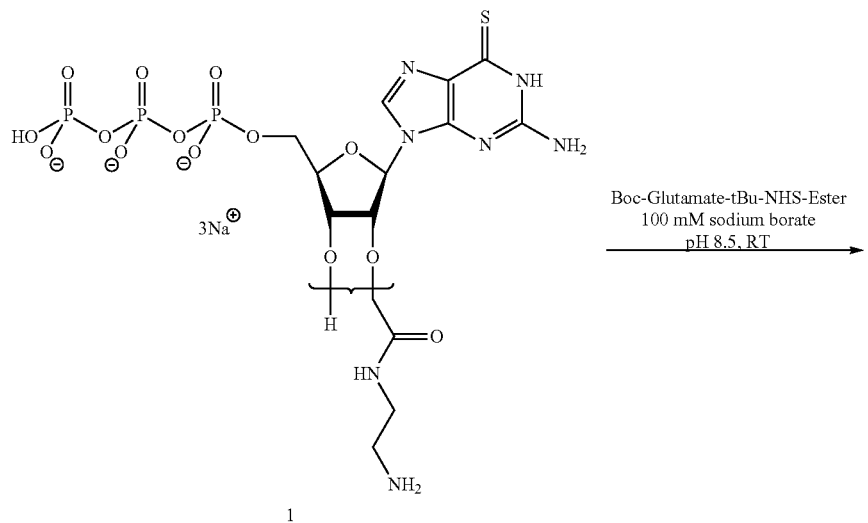

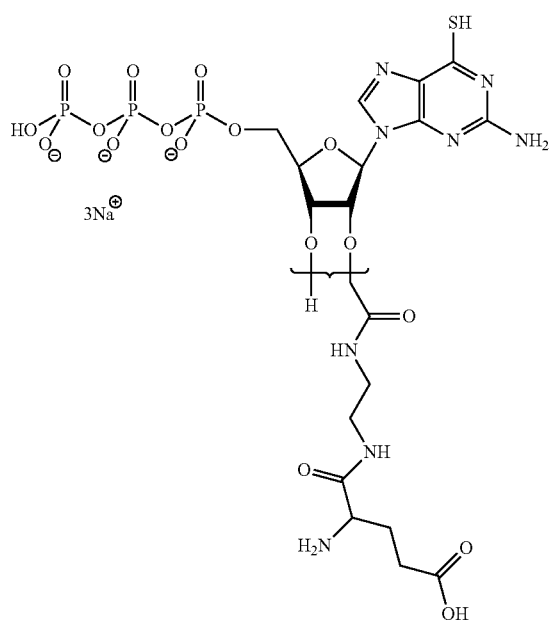

The N-hydroxy-succinimide ester of Boc/tBu-protected Glutamate (2.9 mg, 7 μmol) was dissolved in 200 μl of dry DMF and added to a solution of 1 (5 mg, 7 μmol) in 500 μl of 100 mM sodium borate buffer (pH 8.5) at room temperature. After 16 hours, the reaction mixture was quenched with methanol. The Glutamate labeled product 5 was obtained in 70% yield (3.7 mg, 4.9 μmol) after workup of the reaction mixture by reversed phase HPLC.

Preparation of Threonine-2'/3'-EDA-6-Thio-Guanosine-Triphosphate (6)

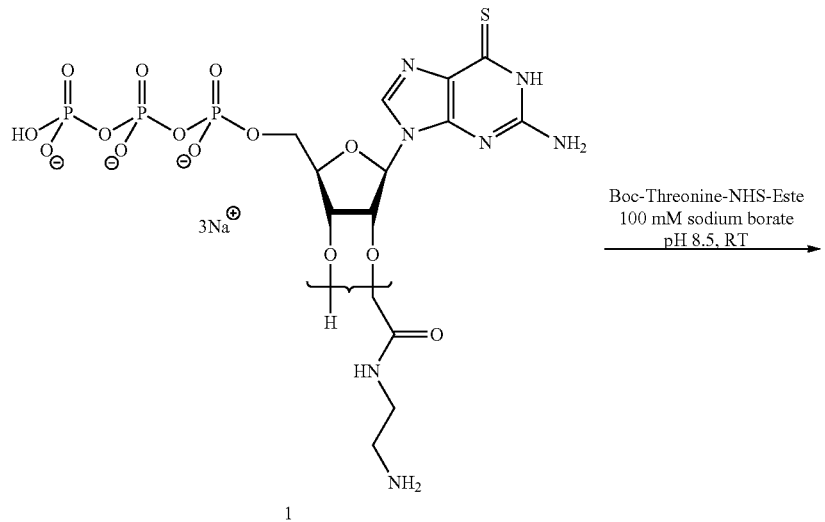

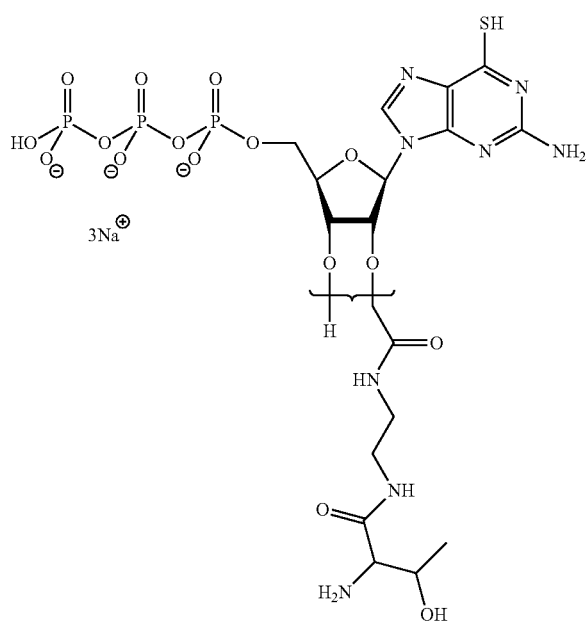

The N-hydroxy-succinimide ester of Boc-protected Threonine (2.3 mg, 7 μmol) was dissolved in 200 μl of dry DMF and added to a solution of 1 (5 mg, 7 μmol) in 500 μl of 100 mM sodium borate buffer (pH 8.5) at room temperature. After 16 hours, the reaction mixture was quenched with methanol. The Threonine derivative 6 was obtained in 70% yield (3.4 mg, 4.9 μmol) after workup of the reaction mixture by reversed phase HPLC.

EXAMPLE 5

Analysis of the Ability of 5 New Synthesized 6-Thio-GTP-Derivatives to Induce Apoptosis in Human CD4+ T Lymphocytes Used Substances:
  Azathioprine
  6-Mercaptopurine
  V1=BMB20=EDA-6-Thio-GTP
  V2=TWI 35/1=N-2-(6"-Aminohexyl)-guanosine
  V3=TWI 71/2=2',3',5',o-Triacetyl-N-2-(Acetyl-6"-aminohexyl)-guanosine
  V4=TWI 107/7=2',3',5'-Triacetyl-N-2-(6"-thioacetamidehexyl)-6-Thioguanosine
  V5=BMB=TAMRA-EDA-6-Thio-GTP V3 and V4 were not soluble in water, therefore V3 was reconstituted with ethanol and V4 was reconstituted with methanol.

Protocol:
Human peripheral blood mononuclear cells (PBMC) from 4 buffycoats were isolated using Ficoll-Hypaque gradients. PBMC were further purified using CD4 monoclonal antibodies attached to immunomagnetic microbeads according to the protocol provided by the manufacturer (Miltenyi Biotec). T lymphocytes were stimulated in complete RPMI-1640 medium (RPMI-1640+10% FCS+100 U/ml Penicillin/Streptomycin+3 mM L-Glutamin) for 3, 4 or 5 days with coated antibodies to CD3 (0.04 μg/ml) and soluble CD28 antibodies (PharMingen; 1 □g/ml) plus IL-2 (R & D Systems, Wiesbaden, Germany; 40 U/ml). Azathioprine, 6-Mercaptopurine, V1, V2, V3, V4 or V5 were added to the T cell cultures at day 0 at a final concentration of 5 μM. To determine induction of apoptosis in these T lymphocytes, cells were analyzed by FACS. For FACS analysis, apoptotic cells were detected by staining with annexin V and propidium iodide using the Annexin V FITC Apoptosis Detection Kit I (PharMingen). In brief, T cells were washed twice in PBS, and the pellet was resuspended in annexin V binding buffer (PharMingen) at a concentration of $10^6$ cells per milliliter. Annexin V FITC and propidium iodide were added (5 μl of each per $10^5$ cells), Samples were gently mixed and incubated for 15 minutes at room temperature in the dark before FACS analysis.

Results:
  Annexin-positive, propidium iodide-negative cells (black bars) present the rate of early apoptotic cells. Annexin-positive, propidium iodide-positive cells (white bars) present late apoptotic or necrotic cells.
  Induction of apoptosis=(Rate of apoptotic cells after indicated treatment)–(Rate of apoptosis of untreated cells)
  V1, V2 and V3 were tested in 4 independent experiments. V4 and V5 were tested in 2 independent experiments.

CONCLUSION

Figure 2:
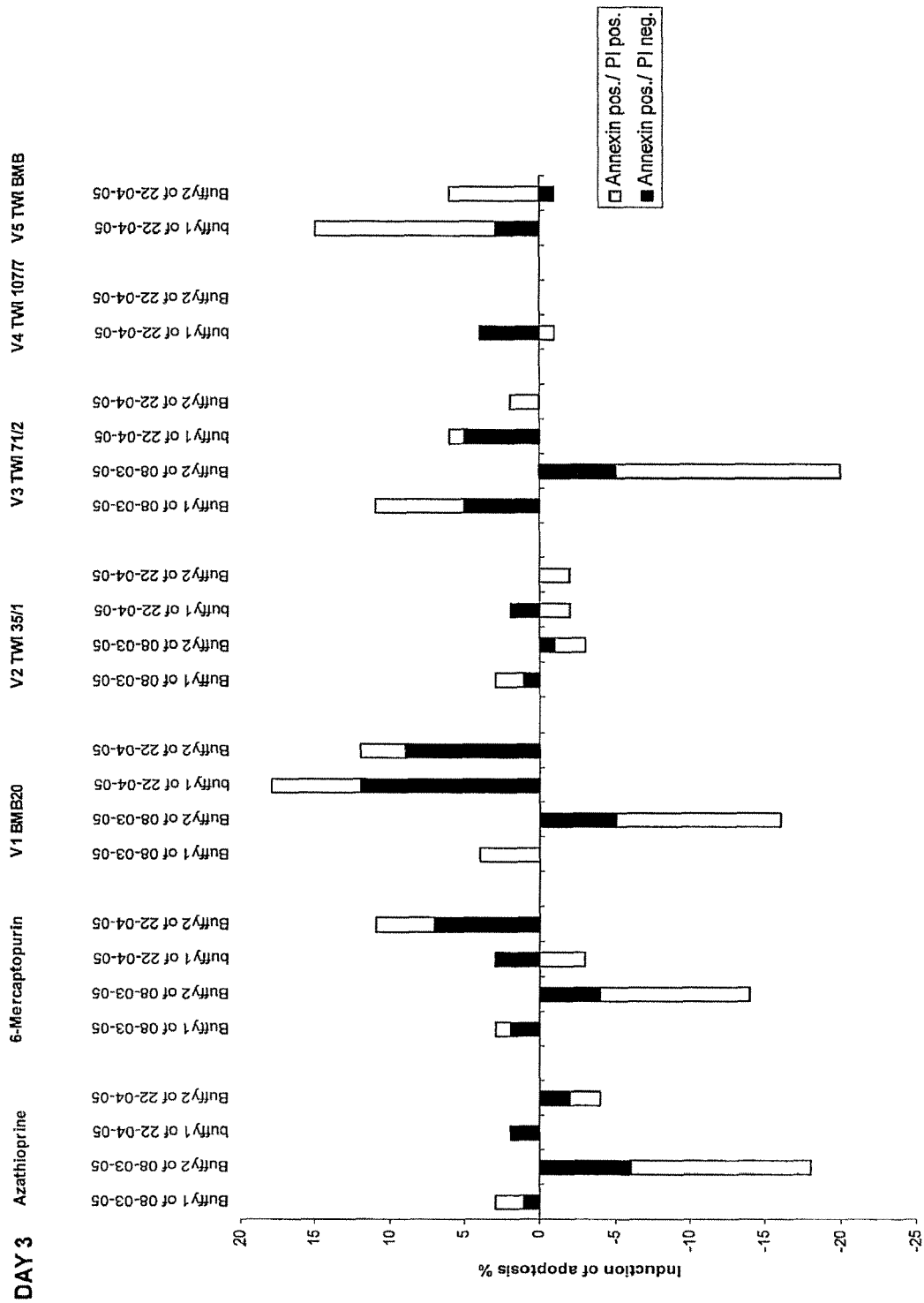
FIG. 2 shows the apoptosis induction in human CD4+ T Lymphocytes by V1=BMB20=EDA-6-Thio-GTP, V2=TWI 35/1=N-2-(6"-Aminohexyl)-guanosine, V3=TWI 71/2=2',3',5',o-Triacetyl-N-2-(Acetyl-6"-aminohexyl)-guanosine, V4=TWI 107/7=2',3',5'-Triacetyl-N-2-(6"-thioacetamide-hexyl)-6-Thioguanosine, V5=BMB=TAMRA-EDA-6-Thio-GTP after 3 days.
Figure 3:
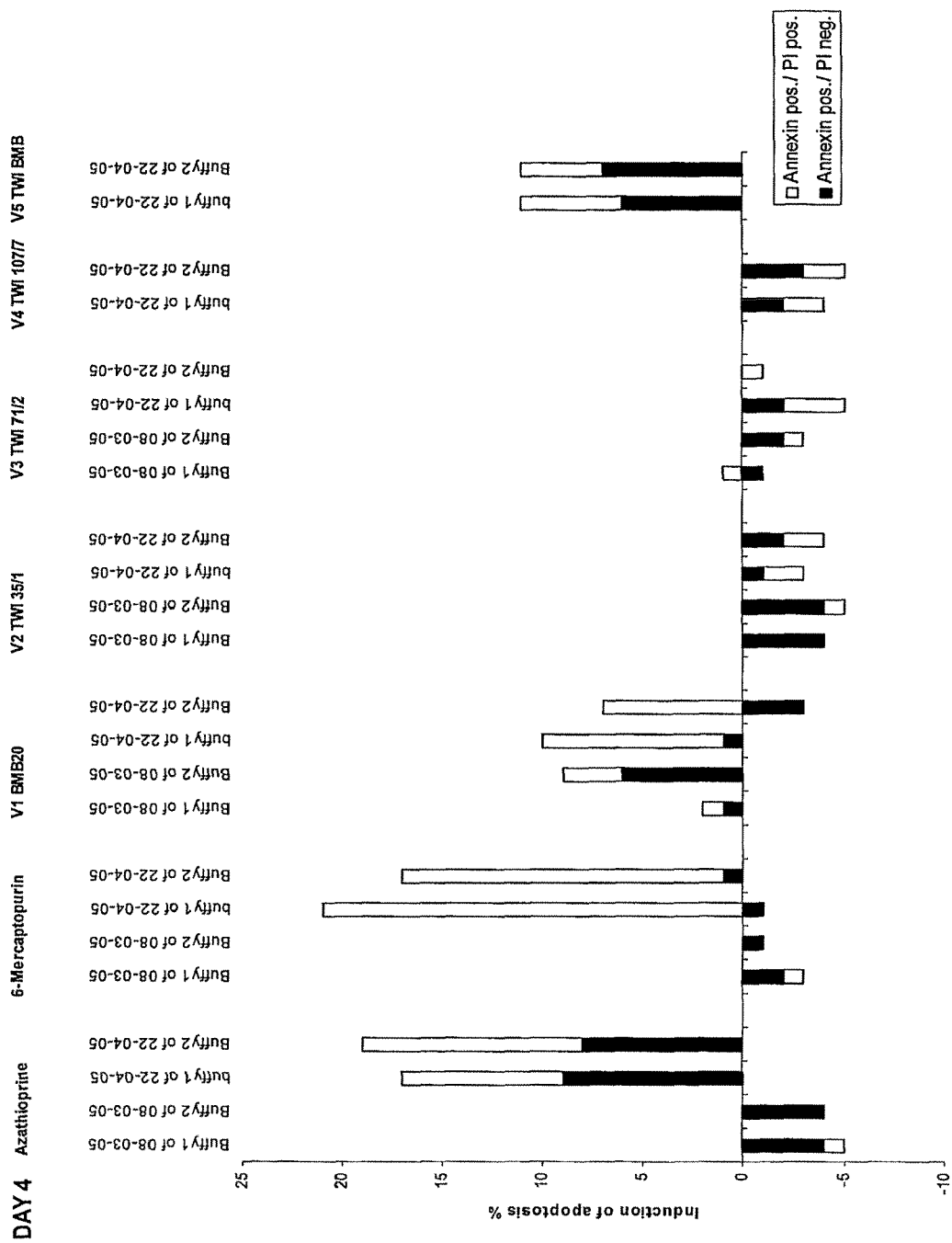
FIG. 3 shows the apoptosis induction in human CD4+ T Lymphocytes by V1=BMB20=EDA-6-Thio-GTP, V2=TWI 35/1=N-2-(6"-Aminohexyl)-guanosine, V3=TWI 71/2=2',3',5',o-Triacetyl-N-2-(Acetyl-6"-aminohexyl)-guanosine, V4=TWI 107/7=2',3',5'-Triacetyl-N-2-(6"-thioacetamide-hexyl)-6-Thioguanosine, V5=BMB=TAMRA-EDA-6-Thio-GTP after 4 days.
Figure 4:
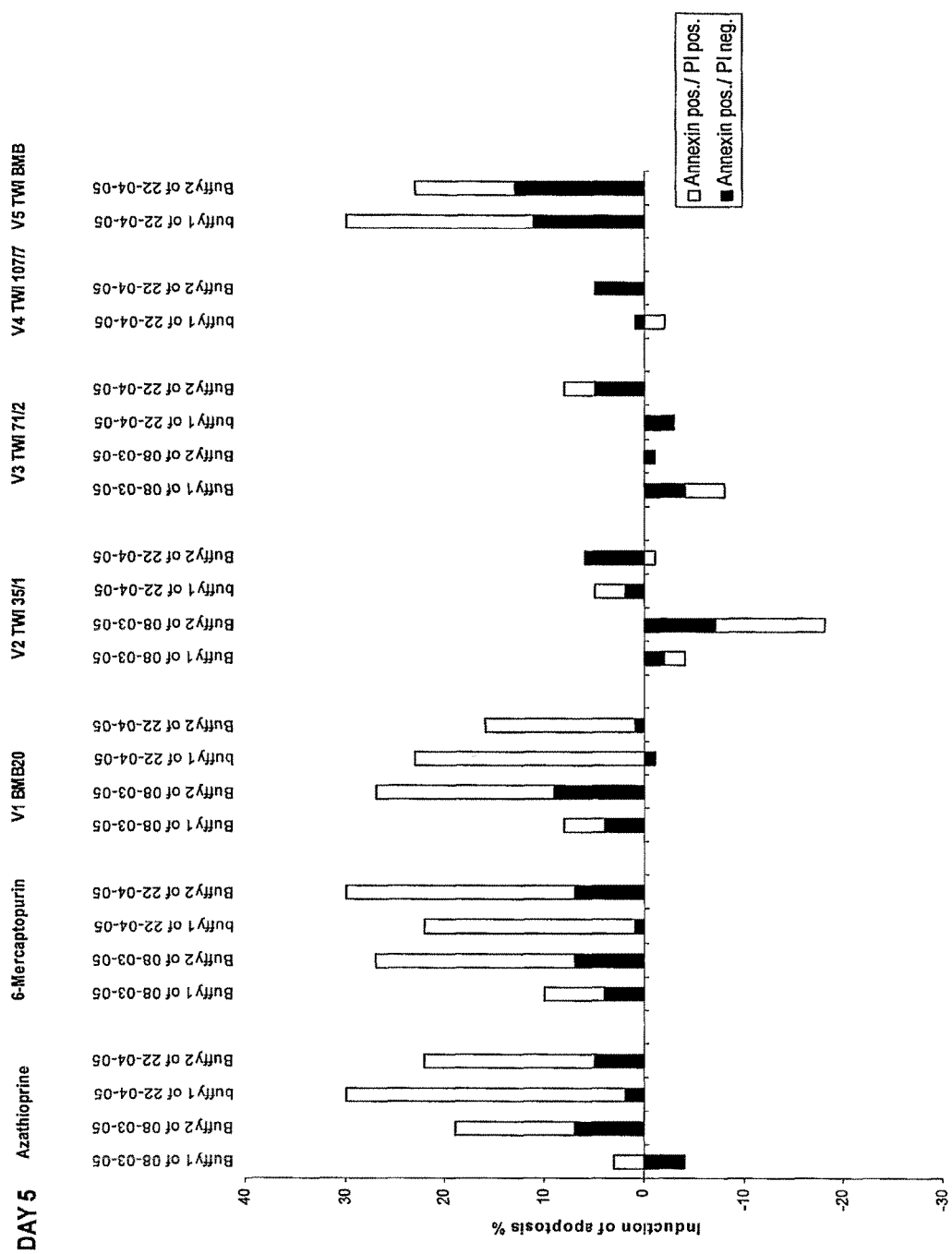
FIG. 4 shows the apoptosis induction in human CD4+ T Lymphocytes by V1=BMB20=EDA-6-Thio-GTP, V2=TWI 35/1=N-2-(6"-Aminohexyl)-guanosine, V3=TWI 71/2=2',3',5',o-Triacetyl-N-2-(Acetyl-6"-aminohexyl)-guanosine, V4=TWI 107/7=2',3',5'-Triacetyl-N-2-(6"-thioacetamide-hexyl)-6-Thioguanosine, V5=BMB=TAMRA-EDA-6-Thio-GTP after 5 days.

Our first results showed, that V1 and V5 were able to induce apoptosis in CD3/CD28 costimulated T Lymphocytes. V2, V3 and V4 were not able to induce apoptosis. Comparing V1 and V5 mediated induction of apoptosis with azathioprine or 6-mercaptopurine mediated induction of apoptosis, V1 and even V5 mediated effects seemed to be more pronounced and appeared earlier (FIGS. 2-4).

EXAMPLE 5

Preparation of 2'/3'-Methylenoaminocarbamate derivatives of 6-Thio-Guanosine-triphosphate

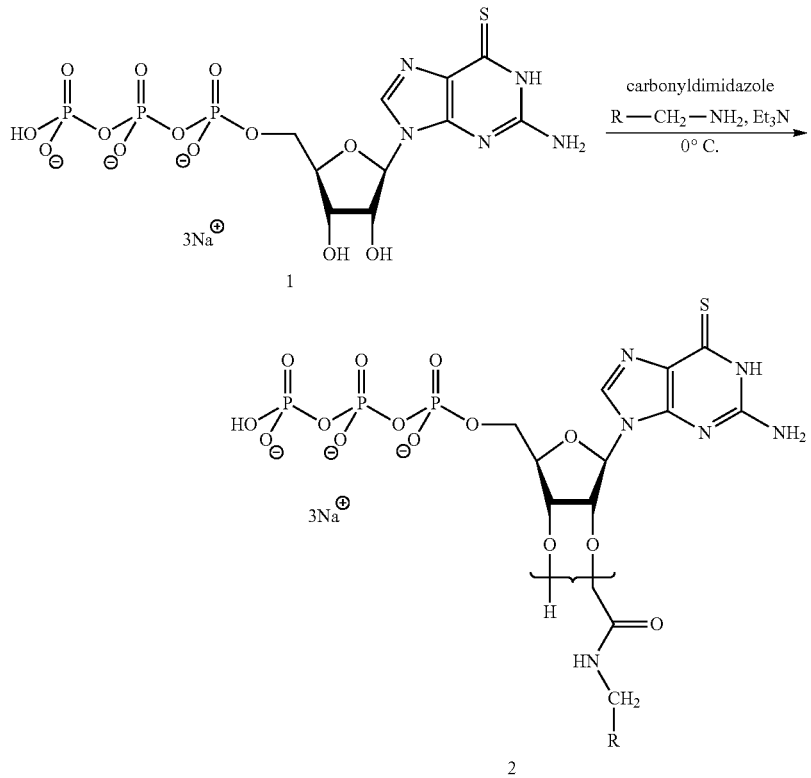

The dry tributylammonium salt of 6-Thio-GTP 1 (0.2 mmol) was treated with 200 mg carbonyl-diimidazole in 4 ml dimethylformamide. The resulting mixture was stirred for 6 hours at 0° C., brought to room temperature and, subsequently, 80 μl of methanol were added. After 10 minutes, 2 mmol of the appropriate methyleno-amine and 2 ml of triethylamine were also added to the reaction mixture. The solution was stirred overnight at room temperature and the solvent was then removed under reduced pressure. The residue was taken up in 30 ml water and the mixture was adjusted to pH 1, in order to decompose the resulting intermediate phosphoramidate at the triphosphate moiety. After 20 minutes, the solution was adjusted to pH 7.5, the precipitate filtered off and the solvent was removed in vacuo. The resulting crude product was purified by ion exchange chromatography and subsequently by reversed phase HPLC.

EXAMPLE 6

2'/3'-Methylenoaminocarbamate-6-Thio-Guanosine-triphosphate derivative 2a

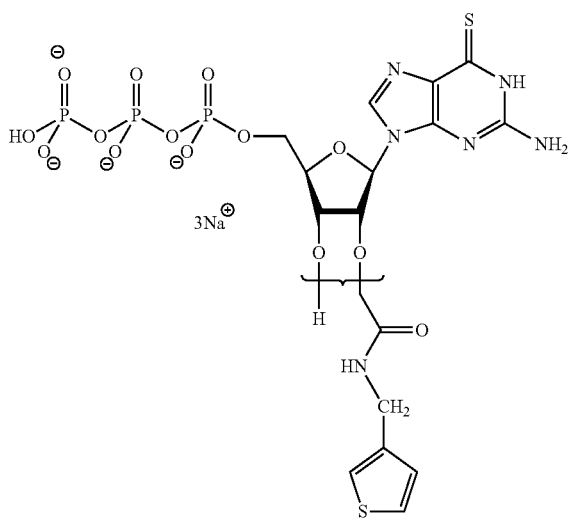

2a

Reaction of 3-thienyl-methylamine (226 mg, 2 mmol) with 1 according to the general procedure yielded 2a (0.58 mmol, 29%) after purification by ion exchange chromatography and subsequent reversed phase HPLC.

2'/3'-Methylenoaminocarbamate-6-Thio-Guanosine-triphosphate Derivative 2b

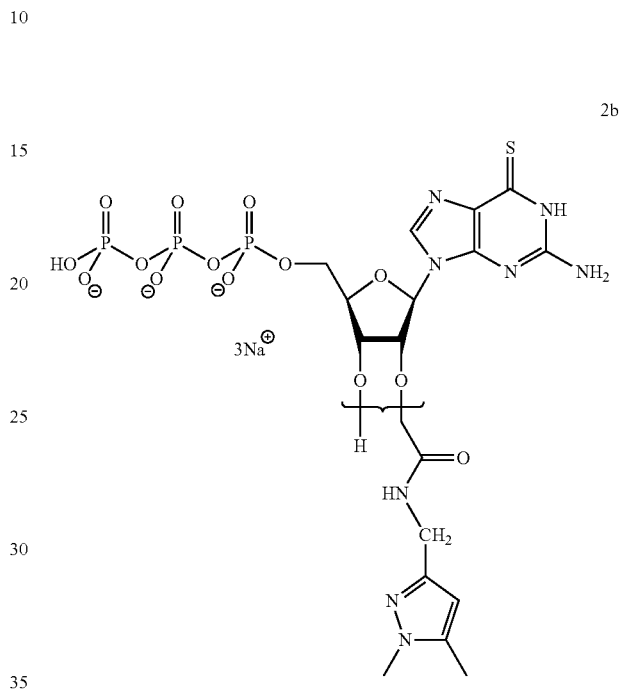

2b

Reaction of (1,5-Dimethyl-1H-pyrazol-3-yl)methylamine (250 mg, 2 mmol) with 1 according to the general procedure yielded 2b (0.66 mmol, 33%) after purification by ion exchange chromatography and subsequent reversed phase HPLC.

EXAMPLE 7

Preparation of 2'/3'-Carbamate Derivatives of 6-Thio-Guanosine-triphosphate

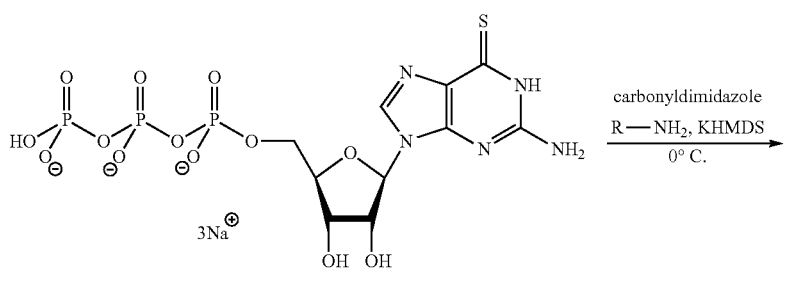

1

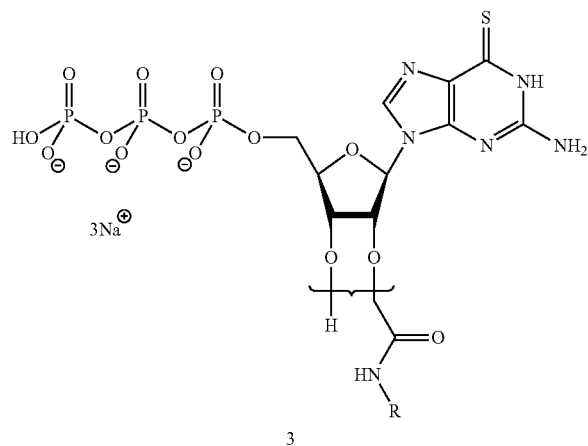

3

The dry tributylammonium salt of compound 1 (0.2 mmol) was treated with 200 mg carbonyl-diimidazole in 4 ml dimethylformamide. The resulting mixture was stirred for 6 hours at 0° C., brought to room temperature and, subsequently, 80 µl methanol were added. After 10 minutes, 2 mmol of the appropriate amine and 2 ml of 1 M potassium hexamethyldisilazide (KHMDS) in THF were carefully added to the solution. The solution was stirred at room temperature for 1 hour and the solvent was then removed under reduced pressure. The residue was taken up in 30 ml water and the mixture was adjusted to pH 1, in order to decompose the resulting intermediate phosphoramidate at the triphosphate moiety. After 20 minutes, the solution was adjusted to pH 7.5, the precipitate filtered off and the solvent was removed in vacuo. The resulting crude product was purified by ion exchange chromatography and subsequently by reversed phase HPLC.

EXAMPLE 8

Figure 5:
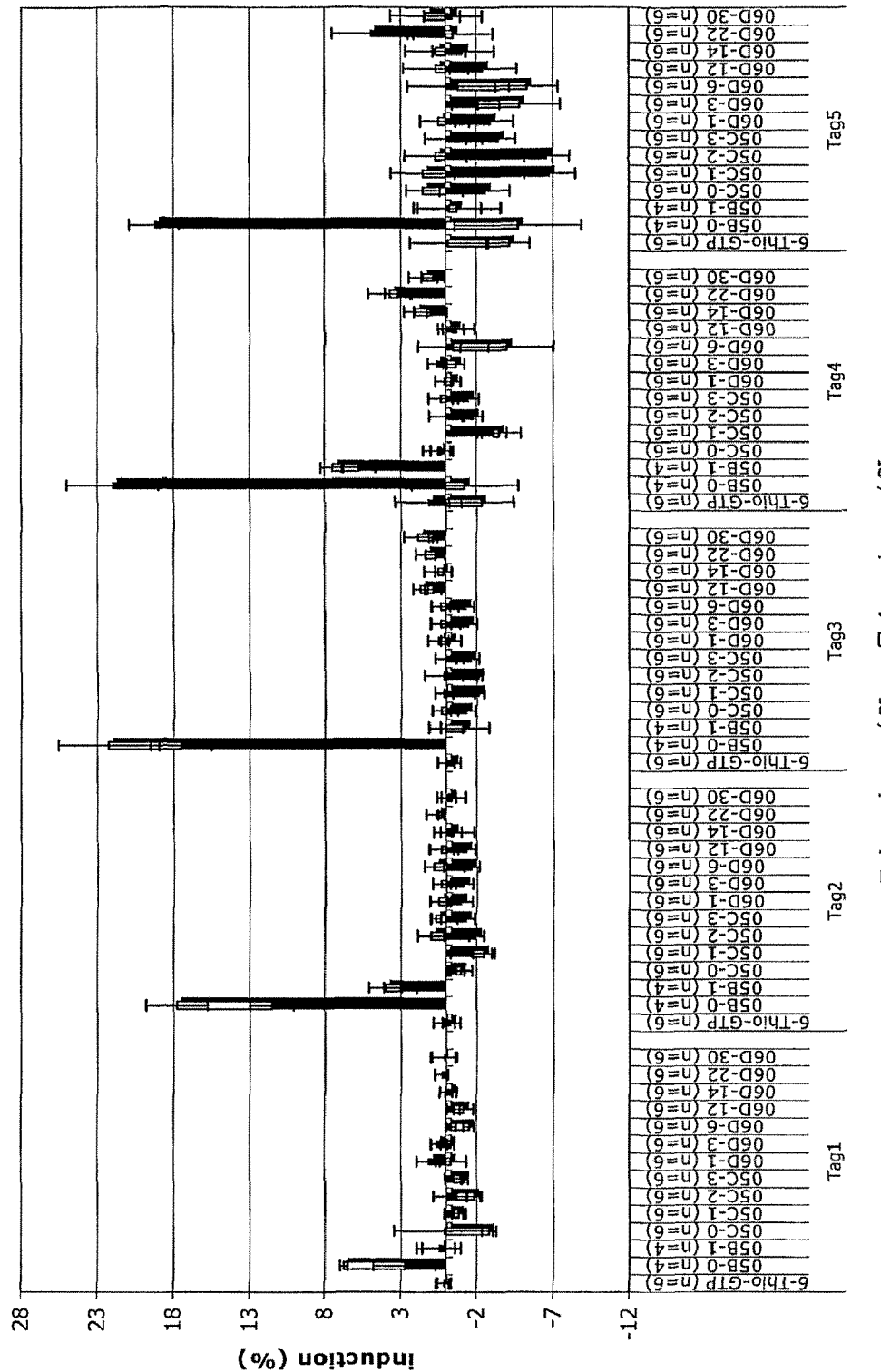
FIG. 5: Induction of apoptosis. Buffy stands for "buffy coat" which is the fraction of blood obtainable by centrifugation and containing leukocytes and platelets. In this case buffy coats were used to isolate monocytes for the experiments. "Buffy 1 vom 08/03/05" means "Buffy coat 1 of Mar. 8, 2005". V1 and V3 have been tested 4 times in four independent experiments, while V2 and V5 were tested twice in two separate experiments. For instance: V1 was tested twice on Aug. 3, 2005 (where Aug. 3, 2004 is written this is in error and should read 08/03/2005) and twice on 22/04/2005

In relation to FIGS. 5 and 6, an overview of at least three experimental data sets on apoptosis is shown below. Here, some of the D compounds were able to induce apoptosis. B0 was the strongest candidate drug for apoptosis induction. Two issues should be considered in these results.

Negative induction of apoptosis means that there were more apoptotic cells in the untreated group than in the treated group. This phenomenon may appear from time to time and may be explained by a kind of statistical variance.

The drug 6-Thio-GTP on average was not able to induce apoptosis in these experiments. Generally 6-Thio-GTP should be a positive control to induce apoptosis in T cells. In these experiments the positive control did not work very well. This might be explained by the fact that the experiments are often preformed with primary T cells, which are freshly isolated from blood of different donors. It is well known, that some people are not sensitive for azathioprine therapy. In this way, T cells of some donors might be resistant against 6-Thio-GTP induced apoptosis. In any case, however, B0 and some of the D compounds were able to induce apoptosis suggesting that they are candidate drugs.

Figure 8:
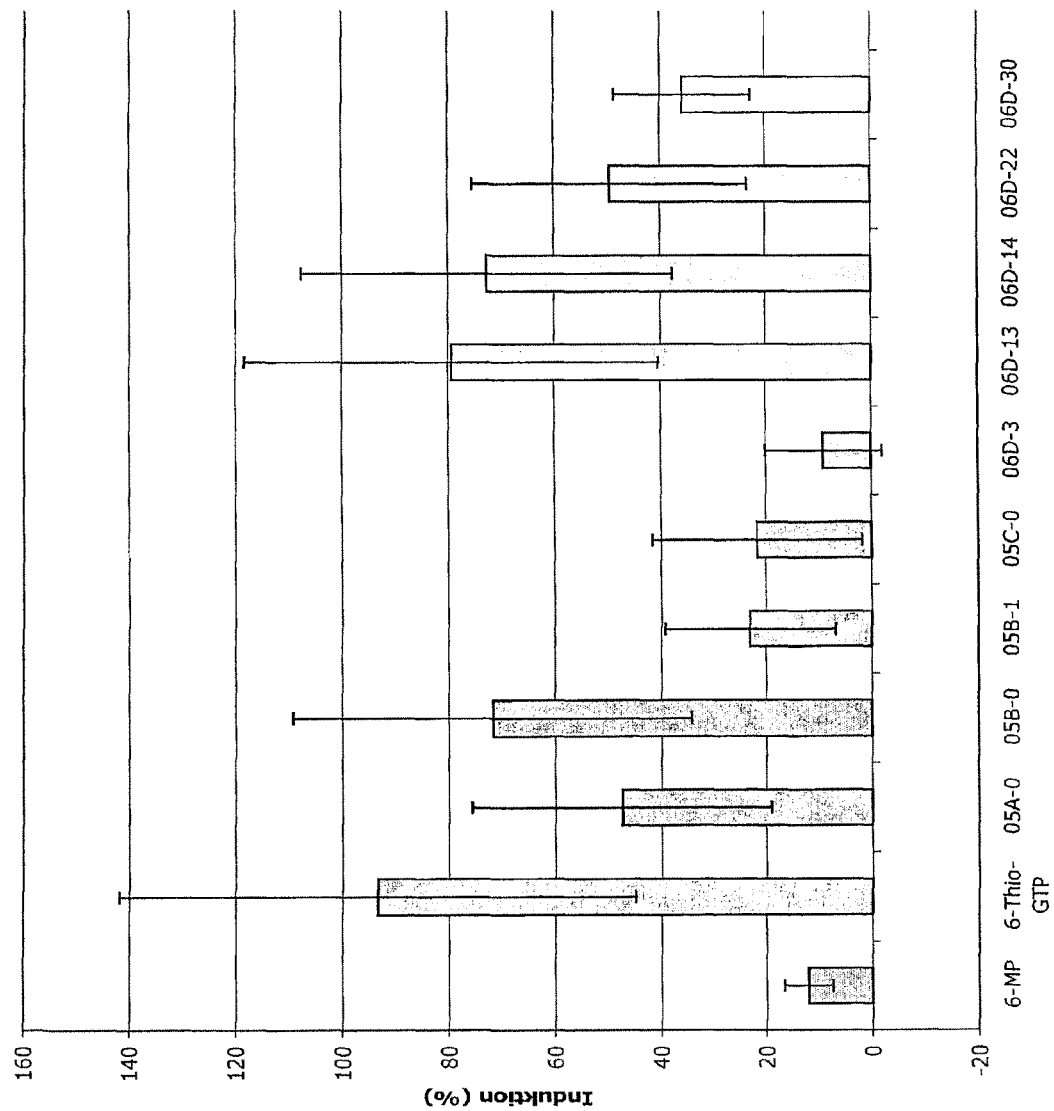
FIG. 8: Caspase-graph: Luminescence value of untreated cells was defined as 100% Caspase activity. Due to their specific luminescence value the caspase activity of treated cells were calculated accordingly. Induction of Caspase activity$_x$[%]=Caspase activity$_x$[%]−Caspase activity$_{untreated}$ [%]. Means±SEM (Standart Error of the Mean=Standard deviation/radical(n)) of three different experiments are presented. Summary of this graph: 6-thio-GTP was able to induce caspase activity (as positive control). 05B-0 was also very effective. 05B-1 was less effective than 05B-0 in agreement with the previous data on AnnexinV/PI-staining. Concerning Group-D derivatives 06D-13, 06D-14 and to a lesser extent 06D-22 were promising.

In addition, an alternative method was performed for screening of group-D derivatives (FIG. 8). It was decided to analyse the activity of caspase-3/7 in T cells, which were treated with group-D derivatives. As compared to AnnexinV/ PI staining this new method might have some advantages:

It is an easier protocol. Therefore there are fewer possibilities for individual errors.

Increased activity of caspase-3 is very specific for apoptosis. Therefore this method is very sensitive for the detection of apoptosis. There is no interfering influence of necrotic cells.

The measurement is done in duplicate. In this way there is an internal control.

The Caspase-Glo 3/7 Assay (Promega™) was used. This assay is based on a caspase dependent luminescent signal. Protocol: $CD4^+$ T cells were isolated from human blood by magnetic beads (Dynal). T lymphocytes were stimulated in complete RPMI-1640 medium (RPMI-1640+10% FCS+100 U/ml Penicillin/Streptomycin+3 mM L-Glutamin) for 3 days with coated antibodies to CD3 (0.04 µg/ml) and soluble CD28 antibodies (PharMingen™; 1 µg/ml) plus IL-2 (R & D Systems™, Wiesbaden, Germany; 40 U/ml) in 96-well plates. Cells were treated with different group-D derivatives or were left untreated. At day three of culture Caspase-3/7 Assay was performed. 25 µl of Caspase-Glo 3/7 reagent was added to each well. Probes were mixed gently for 2 minutes and incubated at room temperature for 30 minutes. Finally 100 µl of each probe were transferred to a white walled 96-well luminometer plate and analysed in a plate-reading luminometer. The added reagent contains a specific substrate of caspase-3 and caspase-7. Cleavage of this substrate by activated caspase-3 results in luciferase reaction. Luminescence is proportional to the amount of caspase activity present (FIG. 8)

EXAMPLE 8

2'/3'-Carbamate-6-Thio-Guanosine-triphosphate derivative 3a

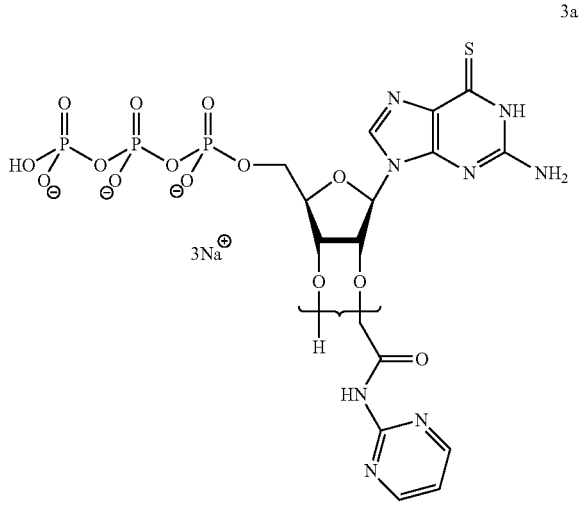

3a

Reaction of 3-aminopyrimidine (190 mg, 2 mmol) with 1 according to the general procedure yielded 3a (0.076 mmol, 3.8%) after purification by ion exchange chromatography and subsequent reversed phase HPLC.

EXAMPLE 9

2'/3'-Carbamate-6-Thio-Guanosine-triphosphate derivative 3b

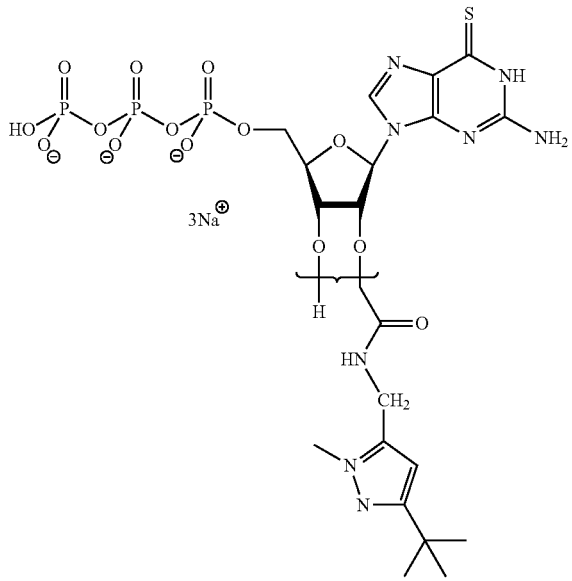

3b

Reaction of 3-(tert.-Butyl)-1-methyl-1H-pyrazol-5-amine (306 mg, 2 mmol) with 1 according to the general procedure yielded 3b (0.11 mmol, 5.5%) after purification by ion exchange chromatography and subsequent reversed phase HPLC.

BIBLIOGRAPHY

Boise L H et al. Receptors that regulate T-cell susceptibility to apoptotic cell death. Ann N Y Acad Sci 1995; 766:70-80.

Tiede I. et al. CD28-dependent Rac1 activation is the molecular target of azathioprine in primary human CD4+ T lymphocytes. J Clin Invest 2003; 111: 1133-1145.

Maltzman J S et al. Azathioprine: old drug, new action. J Clin Invest 2003; 111: 1122-1124.

Boise L H et al. CD28 costimulation can promote T cell survival by enhancing the expression of bcl-$x_L$. Immunity 1995; 3: 87-98.

Khoshnan A. et al. The NF-κB cascade is important in bcl-$x_L$ expression and for the anti-apoptotic effects of CD28 receptor in primary human CD4+ T lymphocytes. J Immunol 2000; 165: 1743-1754.

Noel P J et al. CD28 costimulation prevents cell death during primary T cell activation. J Immunol 1996; 157: 636-642.

Frauwirth K A et al. Activation and inhibition of lymphocytes by costimulation. J Clin Invest 2002; 109: 295-299.

Marinari B et al. Vav cooperates with CD28 to induce NF-κB activation via a pathway involving Rac1 an mitogen-activated kinase 1. Eur J Immunol 2002; 32: 447-456.

Faruqi T R et al. Rac1 mediates STAT-3 activation by autocrine IL-6. PNAS 2001; 98: 9014-9019.

Mudter J and Neurath M F. The role of signal transducers and activators of transcription in T inflammatory bowel diseases. IBD 2003; 9: 332-337.

Lovato P et al. Constitutive STAT-3 activation in intestinal T cells from patients with Crohn's disease. J Biol Chem 2003; 278: 16777-16781.

Van Aelst L et al. Rho GTPases and signaling networks. Genes & Development 1997; 11: 2295-2322.

Kohyoma et al. (2003) A facile synthesis of AICAR from inosine. Synthesis 17:2639.

Imai et al. (1971) Synthesis of compounds related to inosine 5-phosphate and their flavor enhancing activity. IV 2-substituted inosine %'-phosphates. Chem. Pharm. Bull. 19:576.

Ostermann et al (1999), New N-2-labelled fluorescent derivates of guanosine nucleotides and their interaction with GTP-binding proteins. Nucleosides & Nucleotides 18:245.

Ludwig (1981) Acta Biochim. Acad. Sci. Hung. 16:131

The invention claimed is:
1. A compound of the general formula (II):

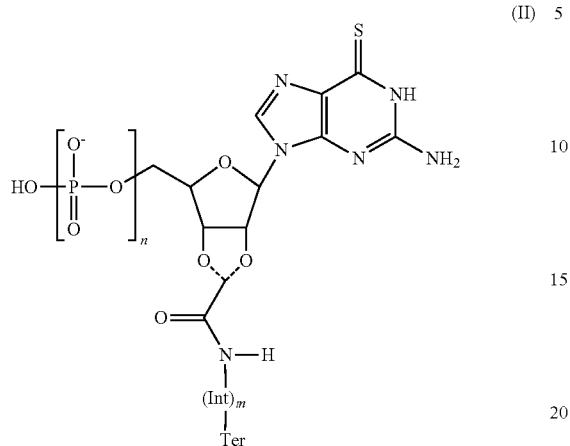

wherein the dashed line indicates that the —O—CO—NH-Int$_m$-Ter moiety is at either the 3' or 2' position and an —OH is at the other; and
wherein n=0, 1, 2 or 3, m is between 0 and 5, Int is selected from the group consisting of

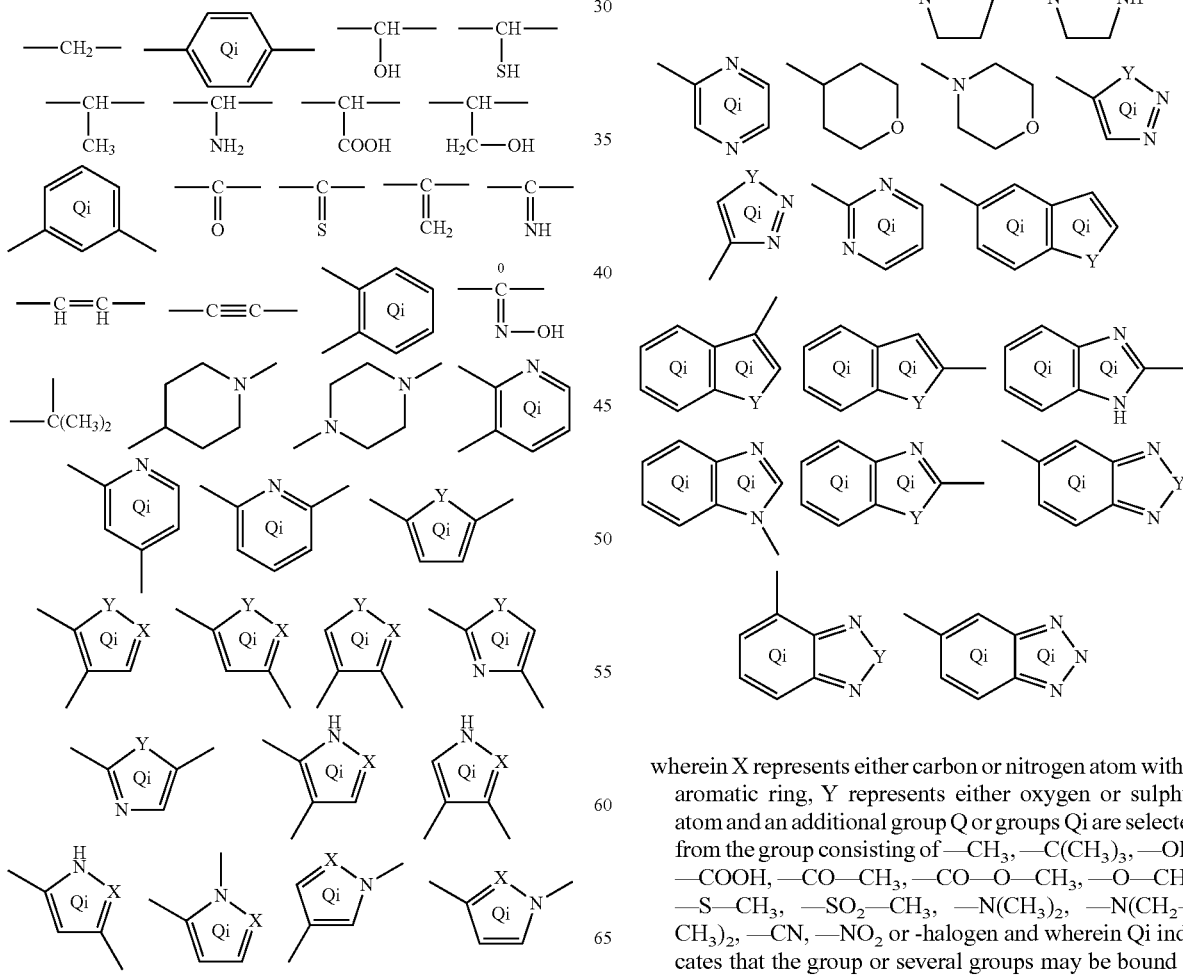

and Ter is selected from group the consisting of

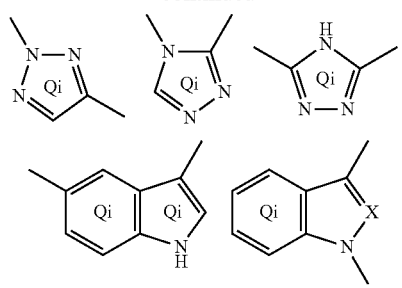

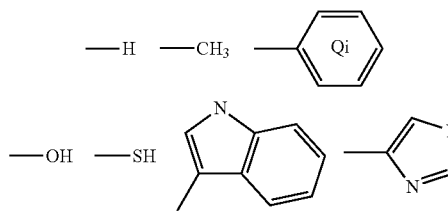

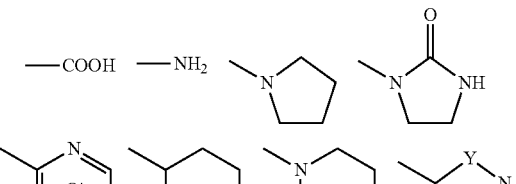

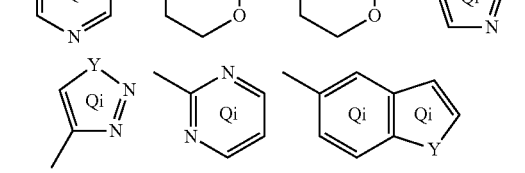

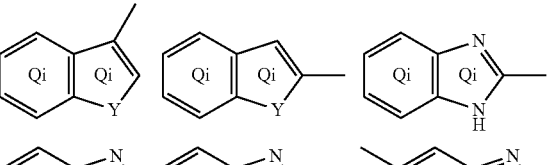

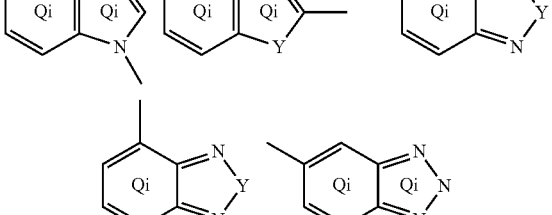

wherein X represents either carbon or nitrogen atom within aromatic ring, Y represents either oxygen or sulphur atom and an additional group Q or groups Qi are selected from the group consisting of —CH$_3$, —C(CH$_3$)$_3$, —OH, —COOH, —CO—CH$_3$, —CO—O—CH$_3$, —O—CH$_3$, —S—CH$_3$, —SO$_2$—CH$_3$, —N(CH$_3$)$_2$, —N(CH$_2$—CH$_3$)$_2$, —CN, —NO$_2$ or -halogen and wherein Qi indicates that the group or several groups may be bound to any unsaturated moiety of the ring.

2. A compound as claimed in claim 1 with the following structure:

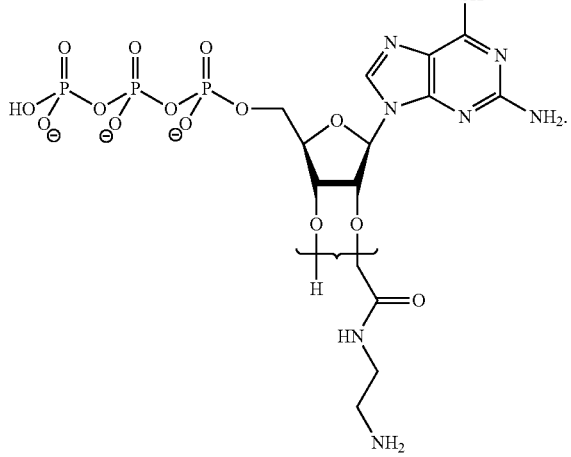

3. A compound as claimed in claim 1 wherein n is 0.
4. A compound as claimed in claim 1 wherein n is 3.
5. A compound as claimed in claim 1 wherein n is 1.
6. A compound as claimed in claim 1 wherein n is 2.
7. The compound of claim 1, wherein Int is —CH$_2$—.
8. The compound of claim 7, wherein Ter is —NH$_2$.

9. A compound represented by:

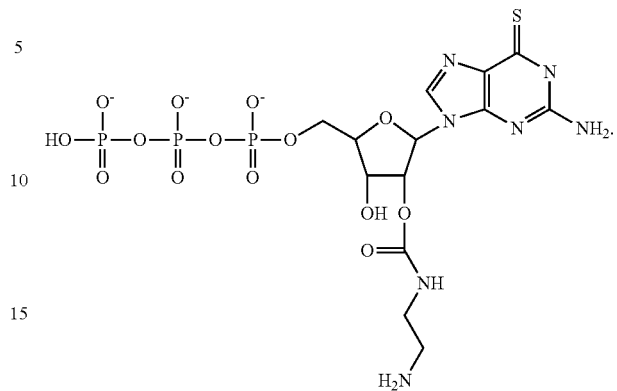

10. A compound represented by:

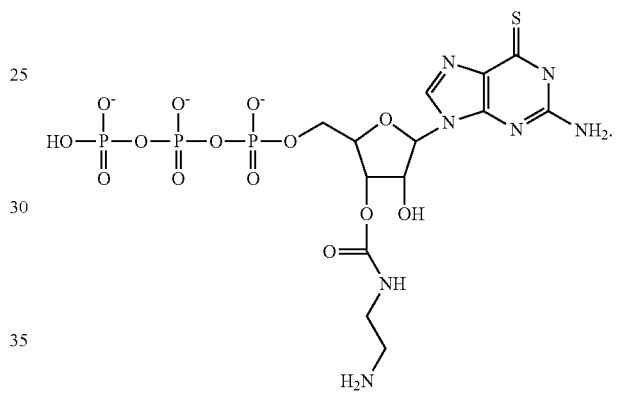

* * * * *